United States Patent
Lim et al.

(10) Patent No.: US 10,744,086 B2
(45) Date of Patent: Aug. 18, 2020

(54) FAST DISSOLVING SOLID DOSAGE FORM

(75) Inventors: Chin Beng Stephen Lim, Willetton (AU); Vivian Bruce Sunderland, Claremont (AU); Yip Hang Eddy Lee, Singapore (SG)

(73) Assignee: iX Biopharma Ltd., Singapore (SG)

( * ) Notice: Subject to any disclaimer, the term of this patent is extended or adjusted under 35 U.S.C. 154(b) by 0 days.

(21) Appl. No.: 13/504,309

(22) PCT Filed: Oct. 26, 2010

(86) PCT No.: PCT/SG2010/000409
§ 371 (c)(1),
(2), (4) Date: Apr. 26, 2012

(87) PCT Pub. No.: WO2011/053251
PCT Pub. Date: May 5, 2011

(65) Prior Publication Data
US 2012/0219628 A1 Aug. 30, 2012

(30) Foreign Application Priority Data
Oct. 30, 2009 (SG) .................. 200907221-6

(51) Int. Cl.
| *A61K 9/20* | (2006.01) |
| *A61K 47/26* | (2006.01) |
| *A61K 47/38* | (2006.01) |
| *A61K 9/22* | (2006.01) |
| *A61K 9/19* | (2006.01) |
| *A61K 9/00* | (2006.01) |
| *A61K 31/00* | (2006.01) |
| *A61K 31/4468* | (2006.01) |
| *A61K 31/5517* | (2006.01) |
| *A61K 31/135* | (2006.01) |
| *A61K 31/137* | (2006.01) |
| *A61K 31/439* | (2006.01) |
| *A61K 31/519* | (2006.01) |

(52) U.S. Cl.
CPC .......... *A61K 9/0056* (2013.01); *A61K 9/2018* (2013.01); *A61K 9/2095* (2013.01); *A61K 31/00* (2013.01); *A61K 31/135* (2013.01); *A61K 31/137* (2013.01); *A61K 31/439* (2013.01); *A61K 31/4468* (2013.01); *A61K 31/519* (2013.01); *A61K 31/5517* (2013.01)

(58) Field of Classification Search
CPC .......... A61K 9/20; A61K 47/26; A61K 47/38; A61K 9/22; A61K 9/19
See application file for complete search history.

(56) References Cited

U.S. PATENT DOCUMENTS

| 3,767,807 | A | | 10/1973 | Blonde et al. | |
|---|---|---|---|---|---|
| 5,558,880 | A | * | 9/1996 | Gole et al. | 424/484 |
| 6,200,604 | B1 | | 3/2001 | Pather et al. | |
| 6,221,392 | B1 | * | 4/2001 | Khankari et al. | 424/464 |
| 6,316,027 | B1 | | 11/2001 | Johnson et al. | |
| 6,509,040 | B1 | * | 1/2003 | Murray et al. | 424/489 |
| 6,974,590 | B2 | | 12/2005 | Pather et al. | |
| 7,357,891 | B2 | | 4/2008 | Yang et al. | |
| 7,425,292 | B2 | | 9/2008 | Yang et al. | |
| 2003/0224090 | A1 | * | 12/2003 | Pearce et al. | 426/89 |
| 2003/0236183 | A1 | | 12/2003 | De Bruijn et al. | |
| 2004/0033258 | A1 | | 2/2004 | Koike et al. | |
| 2004/0156895 | A1 | | 8/2004 | Pruitt et al. | |
| 2005/0118217 | A1 | * | 6/2005 | Barnhart | A61K 9/006 424/401 |
| 2005/0196438 | A1 | | 9/2005 | Wang et al. | |
| 2005/0208110 | A1 | * | 9/2005 | Singh et al. | 424/443 |
| 2006/0251716 | A1 | | 11/2006 | Norman et al. | |
| 2007/0092553 | A1 | | 4/2007 | Tengler et al. | |
| 2007/0265207 | A1 | * | 11/2007 | Fein | 514/15 |
| 2009/0047350 | A1 | | 2/2009 | Bangalore | |

FOREIGN PATENT DOCUMENTS

| AU | 764346 B2 | 8/2003 |
|---|---|---|
| AU | 764473 B2 | 8/2003 |
| AU | 2004242477 A1 | 1/2005 |
| AU | 2002348432 B2 | 8/2007 |
| AU | 2007203233 A1 | 8/2007 |
| AU | 2002362772 B2 | 9/2007 |
| AU | 2002332118 B2 | 6/2008 |
| AU | 2004208644 B2 | 7/2009 |
| AU | 2010219449 A1 | 9/2011 |
| AU | 2010244194 A1 | 11/2011 |
| EP | 1621186 A1 | 2/2006 |
| EP | 1923074 A1 | 5/2008 |
| JP | 48-68726 B2 | 9/1973 |
| JP | 7-508019 | 7/1995 |
| JP | 2001-278812 A | 10/2001 |

(Continued)

OTHER PUBLICATIONS

Thesaurus.com. Comprise. Date retrieved: Jun. 23, 2014.*
Merriam-Webster.com. Dissolve. Date retrieved: Jun. 23, 2014.*
Definition of Dissolve. Merriam-Webster (Online Webpage). Date retrieved: Aug. 12, 2015. <http://www.merriam-webster.com/dictionary/dissolve>.*
Erickson, Megan. Starch. Central Washington University. Slides 3 and 6, (2013).*
Teknova. Common Biological Buffers. p. 1, (2012).*
Ahmed, I.S., Nafadi, M.M., Formulation of a Fast-Dissolving Ketoprofen Tablet Using Freeze-Drying in Blisters Technique, Drug Development and Industrial Pharmacy, 32:437-442, 2006.

(Continued)

*Primary Examiner* — Tracy Liu
(74) *Attorney, Agent, or Firm* — Fish & Richardson P.C.

(57) ABSTRACT

There is provided a fast dissolving solid dosage form adapted for the release of a biologically active material in the oral cavity wherein the dosage form comprises at least one biologically active material, and at least one matrix forming agent, wherein the dosage form substantially dissolves in the oral cavity. A method of producing the same and a kit comprising the same are also provided.

29 Claims, 52 Drawing Sheets

(56) References Cited

FOREIGN PATENT DOCUMENTS

| | | |
|---|---|---|
| JP | 2002-179558 A | 6/2002 |
| JP | 2003-506480 A | 2/2003 |
| JP | 2006-519187 A | 8/2006 |
| JP | 2008-273989 A | 11/2008 |
| WO | WO-1991/009591 A1 | 7/1991 |
| WO | WO-1993/023017 | 11/1993 |
| WO | WO-1994/014422 A1 | 7/1994 |
| WO | 95/20377 A1 | 8/1995 |
| WO | WO-1997/006786 A1 | 2/1997 |
| WO | WO-1998/031368 A1 | 7/1998 |
| WO | WO-1998/036738 A1 | 8/1998 |
| WO | WO-1999/002140 A1 | 1/1999 |
| WO | WO-1999/009989 A1 | 3/1999 |
| WO | WO-1999/038496 A1 | 8/1999 |
| WO | WO-2000/016750 A1 | 3/2000 |
| WO | WO-2000/016751 A1 | 3/2000 |
| WO | WO-2000/044351 A1 | 8/2000 |
| WO | WO-2000/051539 A1 | 9/2000 |
| WO | WO-2000/061117 A1 | 10/2000 |
| WO | WO 2001/012161 | 2/2001 |
| WO | WO 2001037814 A1 * | 5/2001 |
| WO | WO-2003/030882 A1 | 4/2003 |
| WO | WO-2004/043439 A1 | 5/2004 |
| WO | WO-2004/066986 A1 | 8/2004 |
| WO | WO-2004/067004 A1 | 8/2004 |
| WO | WO 2004/075875 | 9/2004 |
| WO | WO 2005105048 A1 * | 11/2005 ........... A61K 9/2013 |
| WO | WO-2006/031209 A1 | 3/2006 |
| WO | WO-2006/039264 A1 | 4/2006 |
| WO | WO-2006/085101 A2 | 8/2006 |
| WO | WO-2006/103418 A1 | 10/2006 |
| WO | WO-2007/028247 A1 | 3/2007 |
| WO | WO-2007/030754 A2 | 3/2007 |
| WO | WO 2007034287 A2 * | 3/2007 ........... A61K 9/0056 |
| WO | WO-2007/067494 A1 | 6/2007 |
| WO | WO-2007/075422 A2 | 7/2007 |
| WO | WO-2007/143676 A2 | 12/2007 |
| WO | WO-2008/039737 A2 | 4/2008 |
| WO | WO-2008/068471 A1 | 6/2008 |
| WO | WO-2008/100375 A2 | 8/2008 |
| WO | WO-2010/005400 A1 | 1/2010 |

OTHER PUBLICATIONS

Jacob, S., et al., Novel Co-Processed Excipients of Mannitol and Microcrystalline Cellulose for Preparing Fast Dissolving Tablets of Glipizide, Indian Journal of Pharmaceutical Sciences, Sep.-Oct. 2007, pp. 633-639.

International Search Report for International Application No. PCT/SG2010/000409, dated Jan. 21, 2011.

* cited by examiner

FAST DISSOLVING SOLID DOSAGE FORM

FIELD OF THE INVENTION

This invention relates to dosage forms adapted for administration to a subject. Preferably, the dosage forms have rapid dissolution rates.

BACKGROUND

Tablets are a common dosage form to deliver an agent to human beings via oral administration. Drug delivery via the oral cavity mucosa, for example the sublingual mucosa, allows a rapidly dissolving drug to be absorbed by simple diffusion, directly into the systemic circulation via the jugular vein, bypassing the gastrointestinal tract and the hepatic first-pass effect. The sublingual route usually produces a fast and reliable onset of action, and is more suitable for fast dissolving dosage forms.

There is an unmet need in the medical field for dosage forms, which have a rapid dissolution rate in the oral cavity. The previous attempts to overcome the problems associated with solid dosages forms include effervescent tablets, films, chewable tablets, disintegrants and wicking agents. These dosage forms are particularly useful for patients who have difficulty in swallowing e.g. children and elderly people. There are several technologies used for preparing such dosage forms, including freeze-drying, spray-drying, tablet molding and tablet compression.

Freeze drying processes have been used to prepare fast dissolving solid dosage forms. Depending on the manufacturing process, the product obtained is characterised by a highly porous microstructure of the supporting matrix (i.e. mannitol, glycine, lactose, gelatins etc.) in which the active agent is homogeneously dispersed. This technology produces a product which rapidly dissolves in water or in the oral cavity; however, the poor physical integrity of its physical structure severely limits further manufacturing operations such as forming blister packs. Moreover, the freeze drying technology in manufacturing such dosage forms is the high production costs because of the lengthy duration of each freeze drying cycle (normally from 24 to 48 hours). The complexity of the industrial plants is another important factor which prejudices the large scale use of this technology for the development of rapidly dissolving tablets. In addition, the thermal shocks, as a direct consequence of each freeze drying cycle, might physically modify the physical-chemical properties of the outer membrane of microencapsulated particles.

In the freeze-drying processes, gelatin and other gelatin-related materials have been used to formulate agents in fast dissolving dosage forms. Gelatin is carrier or structure-forming agent, and it is commonly used in preparing fast dissolving forms for a wide range of drugs. Gelatin provides strength to the dosage form, thus preventing cracking and break-up of the dosage form. This is especially a problem when the dosage form is being removed from the blister package. Gelatin is advantageous in fast dissolving drug from the dosage form because once the dosage form is placed in the oral cavity it provides rapid dissolution of the dosage form.

Gelatin is a protein which is obtained by the partial hydrolysis of animal collagenous tissue, such as skins, tendons, ligaments and bone. However, one significant problem with mammalian-derived gelatin is that it has a bland taste. This results in the fast dissolving dosage form requiring the use of sweeteners and flavours to hide and mask the taste of the gelatin component. A further problem with conventional mammalian derived gelatin is that it requires the use of heat to affect the gelatin solution. This additional step adds time and cost to the process of manufacture.

An additional problem with the use of gelatin-based material as fast dissolving dosage form matrices is that the gelatin can increase in viscosity of the solution with time. This can lead to processing difficulties. Moreover, the gelatin can lead to homogeneity and sedimentation problems associated with the gelatin solution during the holding period. Other disadvantages of gelatin formulations include being prone to bacterial growth and some individuals dislike the fact it is from animal origin.

Other agents which have been used to replace gelatin in fast dissolving dosage forms are starch and modified starches. One problem with starch is that it has a particulate feel for the patient when in the mouth and can lead to dissatisfaction for the patient. Many modified starches also result in this problem. Furthermore, they are expensive.

Therefore, there is a need in the art for a fast dissolving dosage form which delivers an agent to a patient via oral administration, wherein the dosage form rapidly dissolves in the oral cavity of the patient, and wherein the dosage form does not use substantial amounts of mammalian gelatin or starch or modified starch material.

SUMMARY

According to one aspect of the present invention there is provided a fast dissolving solid dosage form adapted for the release of a biologically active material in the oral cavity wherein the dosage form comprises: (i) at least one biologically active material, and (ii) at least one matrix forming agent, wherein the dosage form substantially dissolves in the oral cavity.

According to another aspect of the present invention there is provided a method to produce the fast dissolving solid dosage form of the present invention comprising the steps of combining at least one matrix forming agent with a biologically active material to form a homogeneous mixture and then freeze drying the mixture to prepare the solid dosage form of the present invention.

According to a further aspect of the present invention there is provided a kit comprising the fast dissolving solid dosage form wherein the dosage form comprises: (i) at least one biologically active material, and (ii) at least one matrix forming agent, wherein the dosage form substantially dissolves in the oral cavity, and instructions for its use.

DETAILED DESCRIPTION

Figure 1:
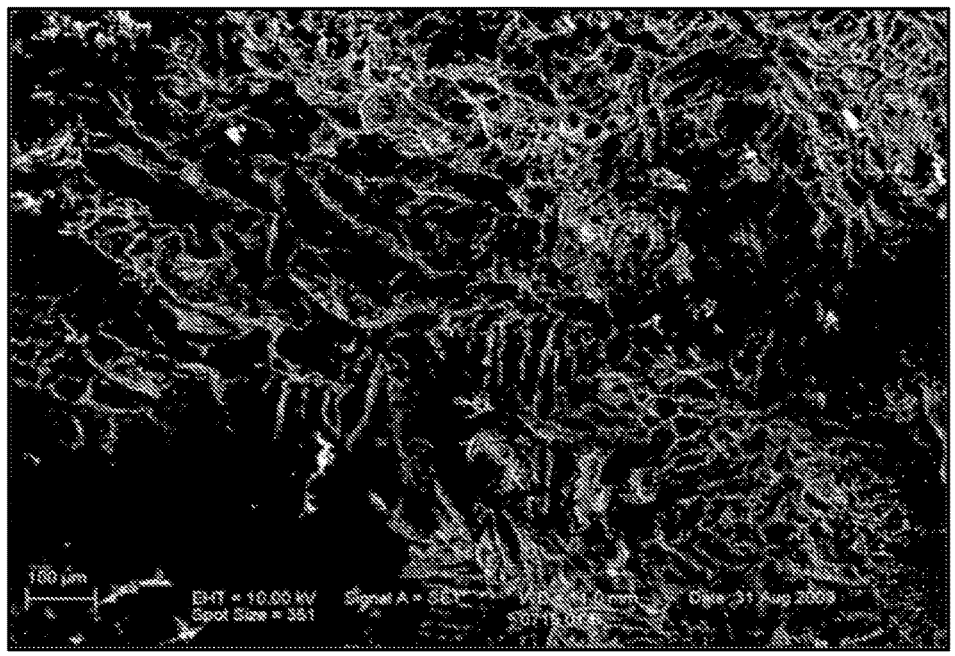
FIG. 1 Scanning electron micrographs of the surface of wafers from batch numbers 071501B and 071502B.
Figure 1:
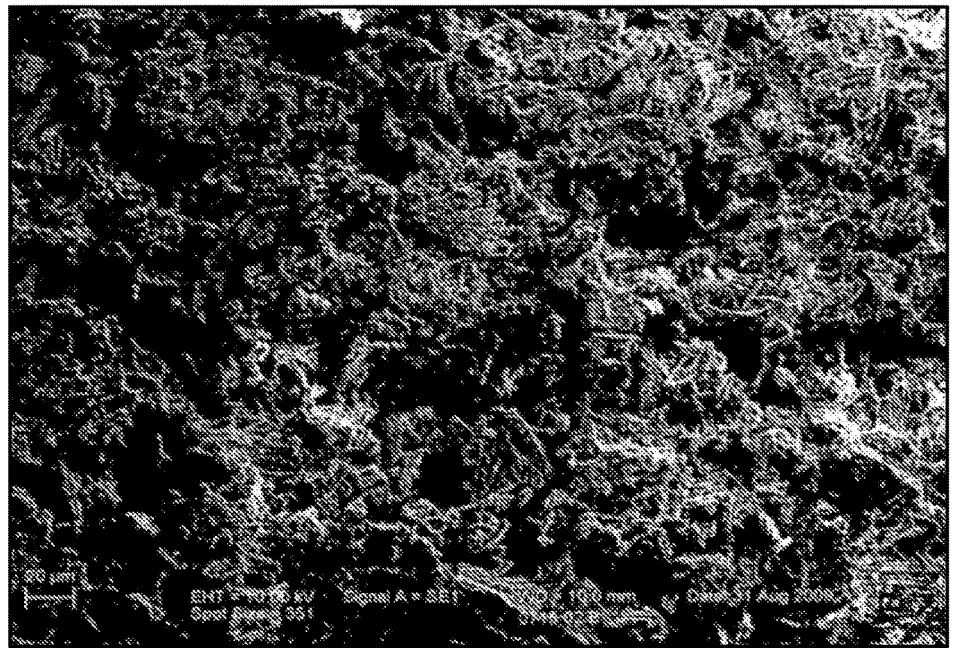
Figure 2:
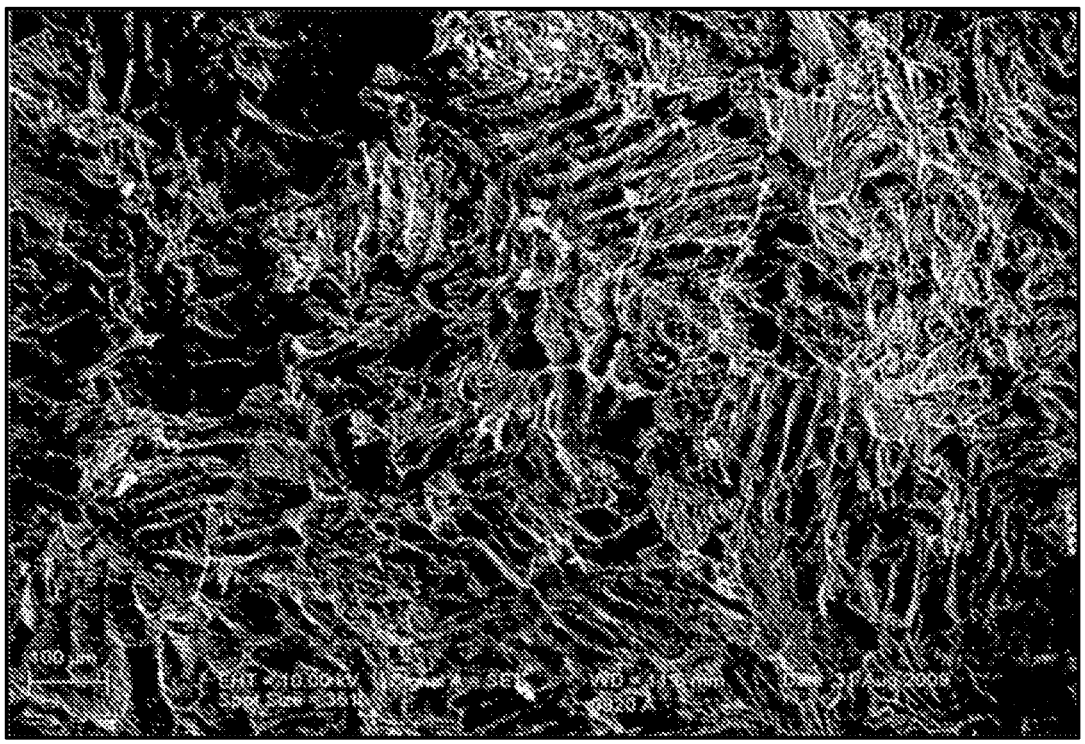
FIG. 2 Scanning electron micrographs of the surface of wafers from batch numbers 0820A and 0820B.
Figure 2:
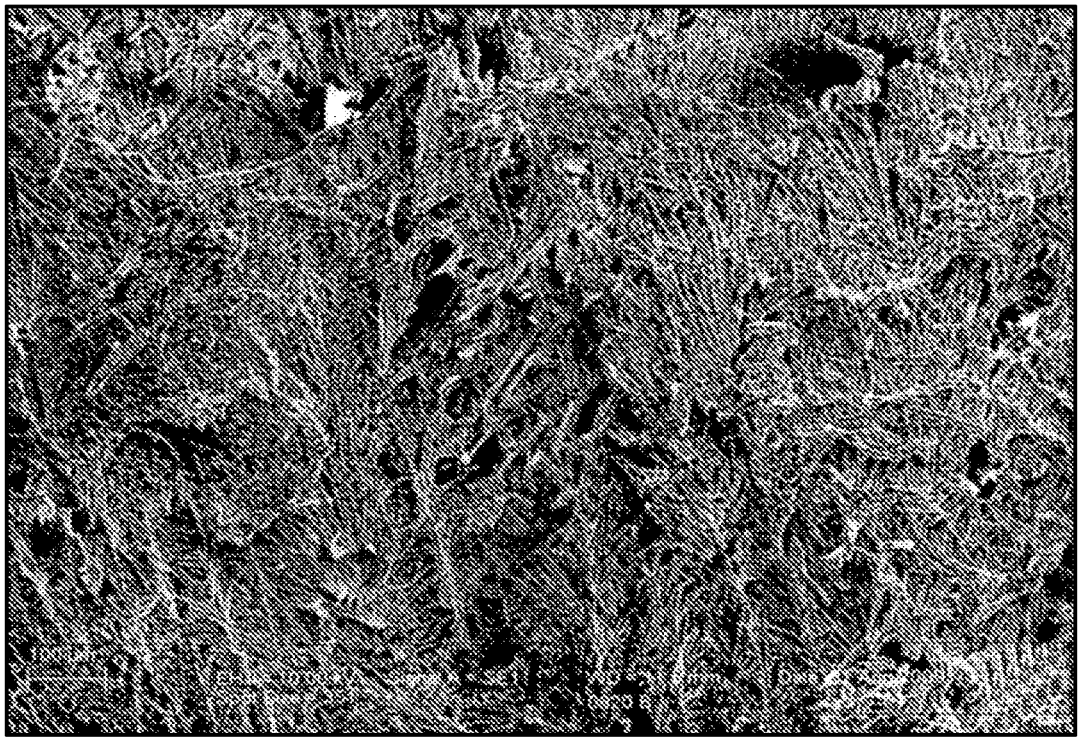
Figure 3:
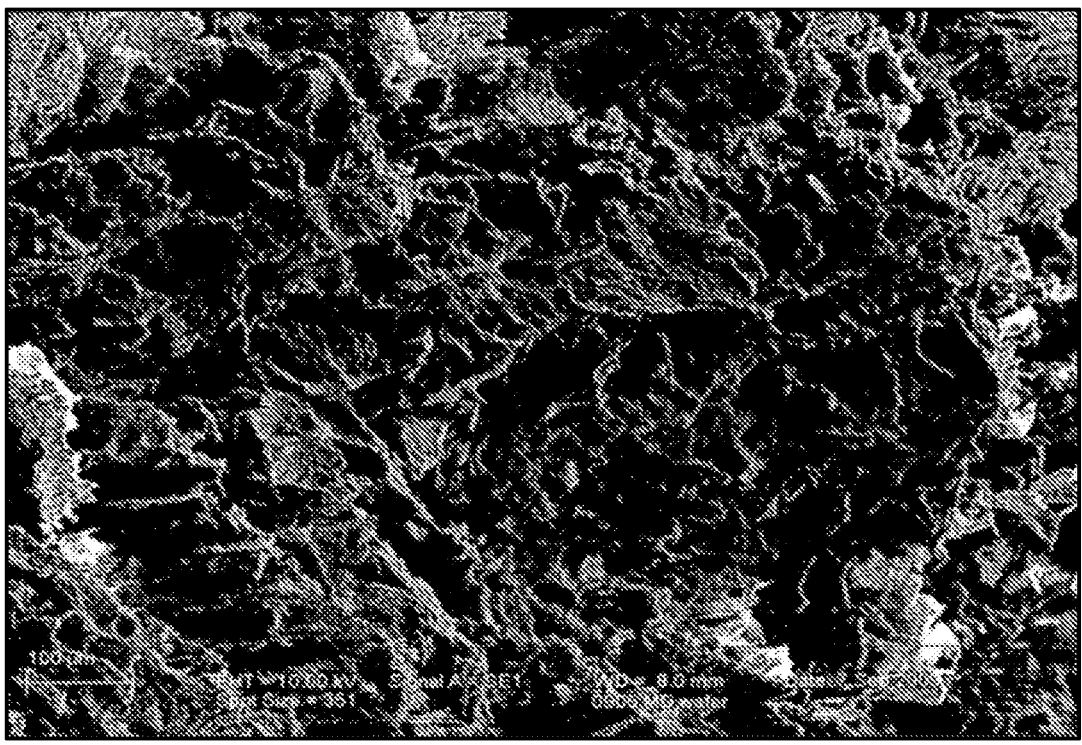
FIG. 3 Scanning electron micrograph of the surface of wafer from batch number 0905MD.
Figure 4:
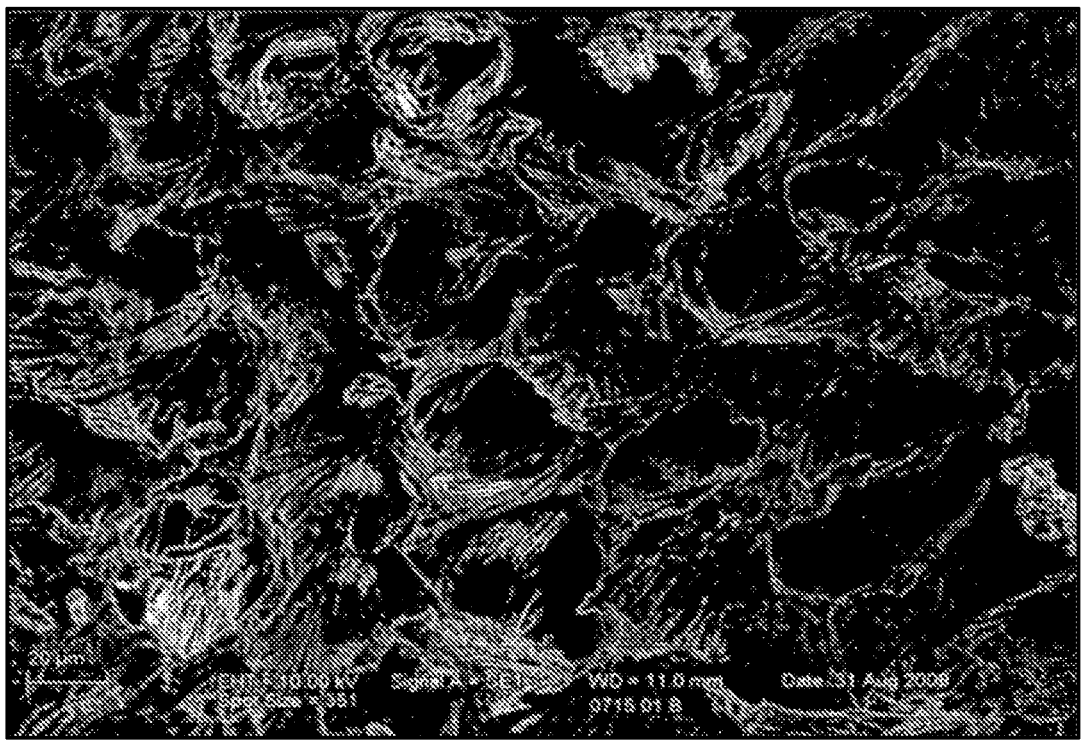
FIG. 4 Scanning electron micrographs of the cross section of wafers from batch numbers 071501B and 071502B.
Figure 4:
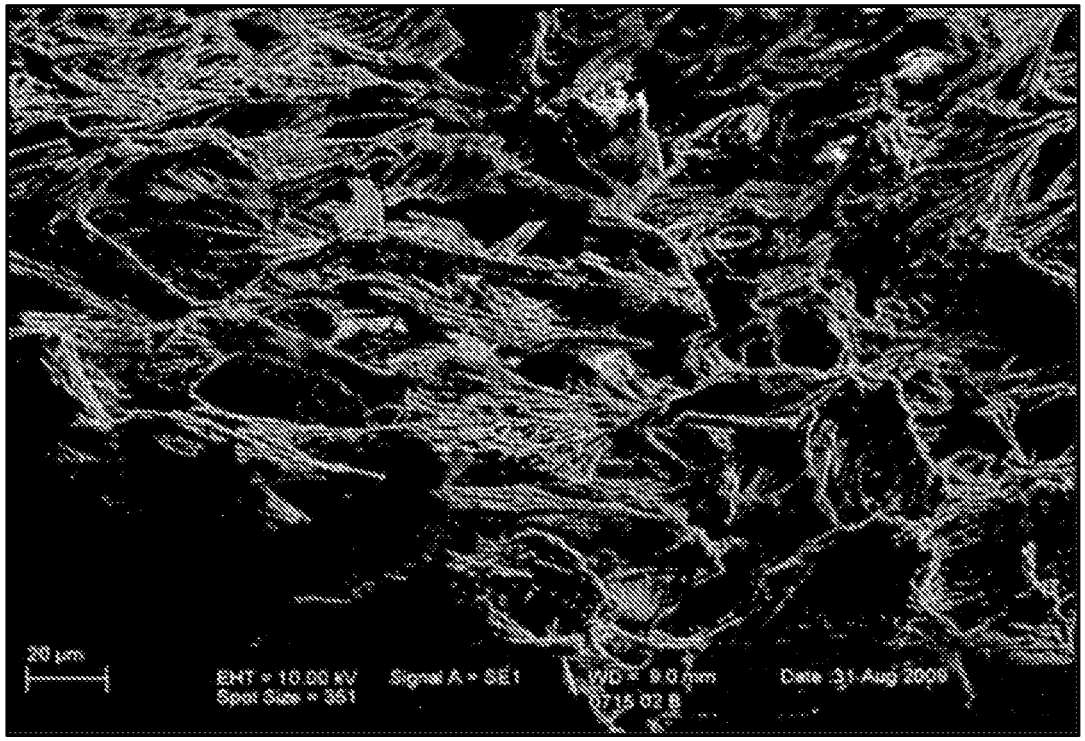
Figure 5:
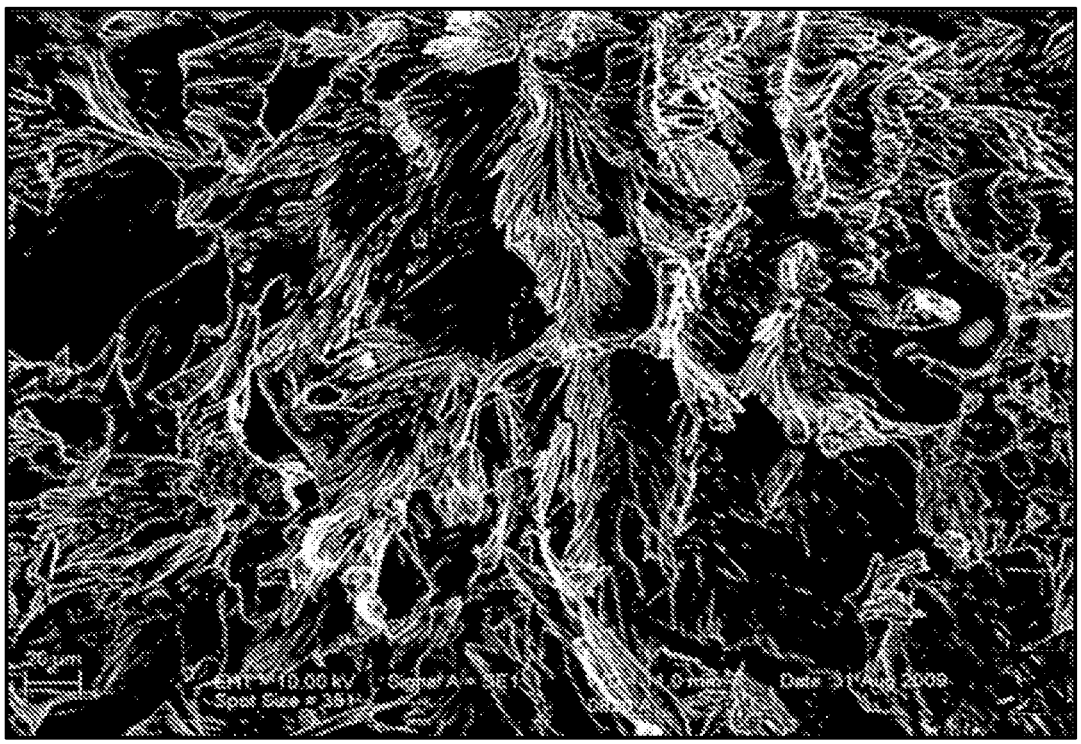
FIG. 5 Scanning electron micrographs of the cross section of wafers from batch numbers 0820A and 0820B.
Figure 5:
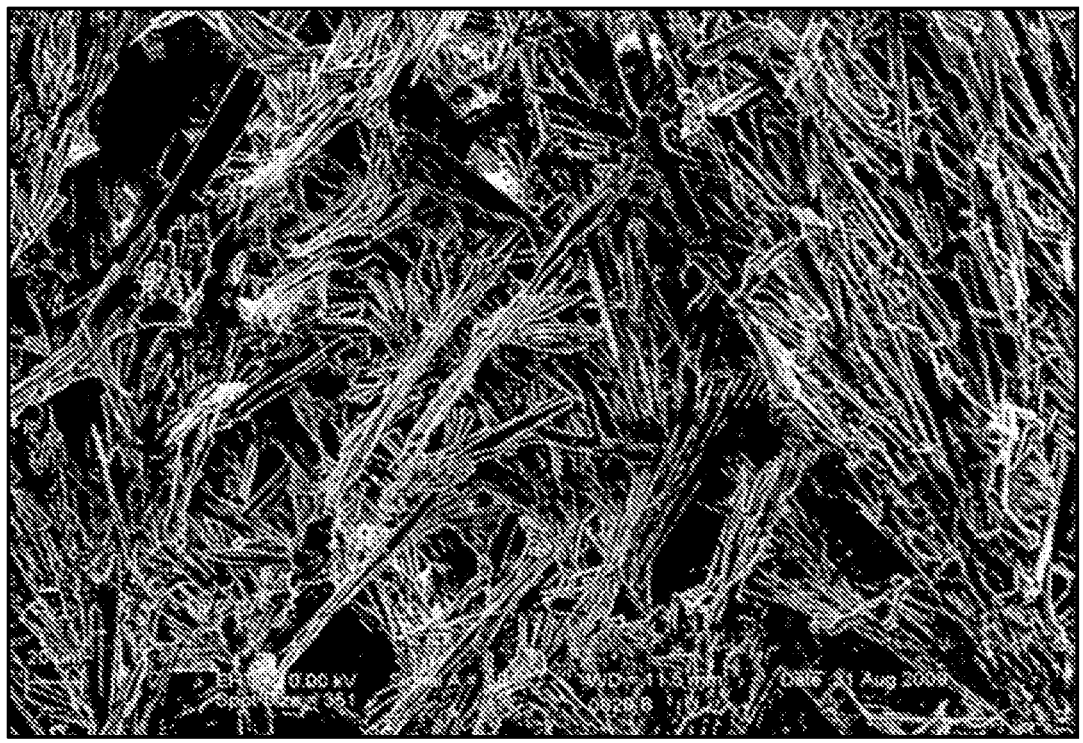
Figure 6:
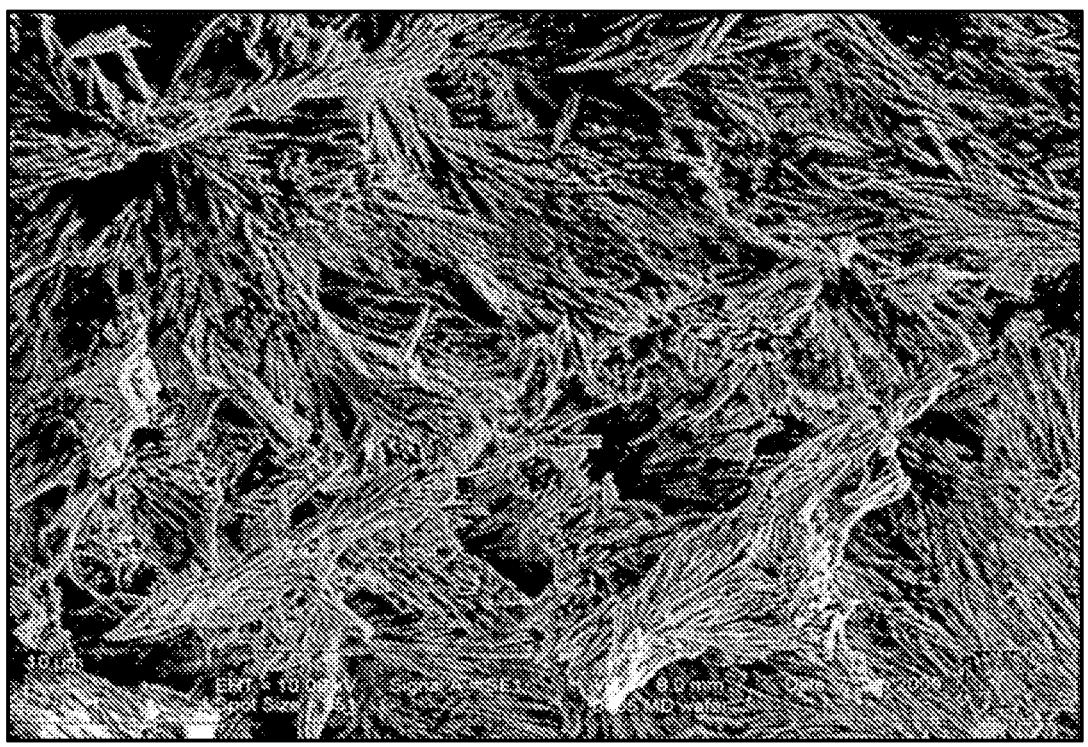
FIG. 6 Scanning electron micrograph of the cross section of wafer from batch number 0905MD.

Those skilled in the art will appreciate that the invention described herein is susceptible to variations and modifications other than those specifically described. It is to be understood that the invention includes all such variations and modifications. The invention also includes all of the steps, features, compositions and materials referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The invention described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this invention relates.

Throughout this specification, unless the context requires otherwise, the word "comprise" or variations, such as "comprises" or "comprising" will be understood to imply the inclusion of a stated integer, or group of integers, however not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

The term "inhibit" is defined to include its generally accepted meaning which includes prohibiting, preventing, restraining, and lowering, stopping, or reversing progression or severity, and such action on a resultant symptom. As such the present invention includes both medical therapeutic and prophylactic administration, as appropriate.

The term "biologically active material" is defined to mean a biologically active compound or a substance which comprises a biologically active compound. In this definition, a compound is generally taken to mean a distinct chemical entity where a chemical formula or formulas can be used to describe the substance. Such compounds would generally, however not necessarily be identified in the literature by a unique classification system such as a CAS number. Some compounds may have a more complex and have a mixed chemical structure. For such compounds they may only have an empirical formula or be qualitatively indentified. A compound would generally be a pure material, although it would be expected that up to 10%, 20%, 30%, 40%, 50%, 60%, 70%, 80%, 90% of the substance could be other impurities and the like. Examples of biologically active compounds are, however not limited to, fungicides, pesticides, herbicides, seed treatments, cosmeceuticals, cosmetics, complementary medicines, natural products, vitamins, nutrients, neutraceuticals, pharmaceutical actives, biologics, amino acids, proteins, peptides, nucleotides, nucleic acids, additives, foods and food ingredients and analogs, homologs and first order derivatives thereof. A substance that contains a biological active compound is any substance which has as one of its components a biological active compound. Examples of substances containing biologically active compounds are, however not limited to, pharmaceutical formulations and products, cosmetic formulations and products, industrial formulations and products, agricultural formulations and products, foods, seeds, cocoa and cocoa solids, coffee, herbs, spices, other plant materials, minerals, animal products, shells and other skeletal material.

Any of the terms, "biological(ly) active", "active", "active material" shall have the same meaning as biologically active material.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for oral administration.\

According to one aspect of the present invention, there is provided a fast dissolving solid dosage form adapted for the release of a biologically active material in the oral cavity wherein the dosage form comprises: (i) at least one biologically active material, and (ii) at least one matrix forming agent, wherein the dosage form substantially dissolves in the oral cavity.

The biologically active material includes active compounds, and compounds for veterinary and human use, such as however not limited to, pharmaceutical actives, neutraceuticals, cosmeceuticals, cosmetics, complementary medicines, natural products, foods, vitamins, nutrients, biologics, amino acids, proteins, peptides, nucleotides, and nucleic acids. In a preferred form the biologically active material is adapted for oral administration.

In a preferred embodiment of the invention, the biologically active material is an organic compound. In a highly preferred embodiment of the invention, the biologically active material is an organic, therapeutically active compound for human use. In another embodiment of the present invention, the biologically active material is an inorganic compound. When the biological active material is a drug, it can be of a neutral species, basic or acidic as well as salts of an acid or base. This invention is not limited to any drug specific class, application type, chemical type or function grouping.

The biologically active material is ordinarily an agent for which one of skill in the art desires improved fast dissolution for oral administration. The biologically active material may be a conventional active agent or drug.

Examples of biologically active materials suitable for use in the invention include actives, biologics, amino acids, proteins, peptides, nucleotides, nucleic acids, and analogs, homologs and first order derivatives thereof. The biologically active material can be selected from a variety of known classes of drugs, including, however not limited to: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-Parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's The Extra Pharmacopoeia, 31st Edition (The Pharmaceutical Press, London, 1996), specifically incorporated by reference. Another source of active agents is the Physicians Desk Reference ($60^{th}$ Ed., 2005), familiar to those of skill in the art. The active agents are commercially available and/or can be prepared by techniques known in the art.

Additionally, examples of suitable drugs include, however are not limited to those listed below:

Analgesics and anti-inflammatory agents: aloxiprin, auranofm, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlodipine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl.

Anti-malarials: amodiaquine, chloroquine, chlorproguanil HCl, halofantrine HCl, mefloquine HCl, proguanil HCl, pyrimethamine, quinine sulphate.

Anti-migraine agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine HCl, hyoscine butyl bromide, hyoscyamine, mepenzolate bromide, orphenadrine, oxyphencyclimine HCl, tropicamide.

Anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole.

Anti-thyroid agents: carbimazole, propylthiouracil.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

Beta-Blockers: acebutolol, alprenolol, atenolol, labetalol, metoprolol, nadolol, oxprenolol, pindolol, propranolol.

Cardiac Inotropic agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Anti-Parkinson agents: bromocriptine mesylate, lysuride maleate.

Gastro-intestinal agents: bisacodyl, cimetidine, cisapride, diphenoxylate HCl, domperidone, famotidine, loperamide, mesalazine, nizatidine, omeprazole, ondansetron HCl, ranitidine HCl, sulphasalazine.

Histamine $H_1$-Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Lipid regulating agents: bezafibrate, clofibrate, fenofibrate, gemfibrozil, probucol.

Local anaesthetics: Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamin A, vitamin B2, vitamin D, vitamin E, vitamin K.

Opioid analgesics: codeine, dextropropyoxyphene, diamorphine, dihydrocodeine, meptazinol, methadone, morphine, nalbuphine, pentazocine, medazolam, fentanyl.

Oral vaccines: Vaccines designed to prevent or reduce the symptoms of diseases of which the following is a representative however not exclusive list: Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Travellers' Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhagic Fever, Caries, Chagas Disease, Urinary Tract Infection caused by *E. coli*, Pneumoccocal Disease, Mumps, and Chikungunya.

Vaccines to prevent or reduce the symptoms of other disease syndromes of which the following is a representative, however not exclusive list of causative organisms: *Vibrio* species, *Salmonella* species, *Bordetella* species, *Haemophilus* species, *Toxoplasmosis gondii*, *Cytomegalovirus*, *Chlamydia* species, *Streptococcal* species, Norwalk Virus, *Escherischia coli*, *Helicobacter pylori*, *Rotavirus*, *Neisseria gonorrhae*, *Neisseria meningiditis*, Adenovirus, Epstein Barr Virus, Japanese Encephalitis Virus, *Pneumocystis carini*, Herpes simplex, *Clostridia* species, Respiratory Syncytial Virus, *Klebsiella* species, *Shigella* species, *Pseudomonas aeruginosa*, *Parvovirus*, *Campylobacter* species, *Rickettsia* species, *Varicella zoster*, *Yersinia* species, Ross River Virus, J. C. Virus, *Rhodococcus equi*, *Moraxella catarrhalis*, *Borrelia burgdorferi* and *Pasteurella haemolytica*. Further specific examples include opioids such as fentanyl or midazolam.

Vaccines directed to non-infections immuno-modulated disease conditions such as topical and systematic allergic conditions such as Hayfever, Asthma, Rheumatoid Arthritis and Carcinomas.

Vaccines for veterinary use include those directed to Coccidiosis, Newcastle Disease, Enzootic pneumonia, Feline leukaemia, Atrophic rhinitis, Erysipelas, Foot and Mouth disease, Swine, pneumonia, and other disease conditions and other infections and auto-immune disease conditions affecting companion and farm animals.

Proteins, peptides and recombinant drugs: insulin (hexameric/dimeric/monomeric forms), glucagon, growth hormone (somatotropin), polypeptides or their derivatives, (preferably with a molecular weight from 1000 to 300,000), calcitonins and synthetic modifications thereof, enkephalins, interferons (especially Alpha-2 interferon for treatment of common colds), LHRH and analogues (nafarelin, buserelin, zolidex),GHRH (growth hormone releasing hormone), secretin, bradykin antagonists, GRF (growth releasing factor), THF, TRH (thyrotropin releasing hormone), ACTH analogues, IGF (insulin like growth factors), CGRP (calcitonin gene related peptide), atrial natriurectic peptide, vasopressin and analogues (DDAVP, lypressin), factorVIII, G-CSF (granulocyte-colony stimulating factor), EPO (erythropoitin).

Sex hormones: clomiphene citrate, danazol, ethinyloestradiol, medroxyprogesterone acetate, mestranol, methyltestosterone, norethisterone, norgestrel, oestradiol, conjugated oestrogens, progesterone, stanozolol, stiboestrol, testosterone, tibolone.

Spermicides: nonoxynol 9.

Stimulants: amphetamine, dexamphetamine, dexfenfluramine, fenfluramine, mazindol, pemoline.

Notwithstanding the general applicability of the method of the invention, more specific examples of biologically active materials include, however are not limited to: haloperidol (dopamine antagonist), DL isoproterenol hydrochloride (β-adrenergic agonist), terfenadine (H1-antagonist), propranolol hydrochloride (β-adrenergic antagonist), desipramine hydrochloride (antidepressant), sildenafil citrate, tadalafil and vardenafil. Minor analgesics (cyclooxygenase inhibitors), fenamic acids, Piroxicam, Cox-2 inhibitors, and Naproxen, and others, may all benefit from being prepared.

Further examples include, however are not limited to: alfaxalone, acetyl digoxin, acyclovir analogs, alprostadil, aminofostin, anipamil, antithrombin III, atenolol, azidothymidine, beclobrate, beclomethasone, belomycin, benzocaine and derivatives, beta carotene, beta endorphin, beta interferon, bezafibrate, binovum, biperiden, bromazepam, bromocryptine, bucindolol, buflomedil, bupivacaine, busulfan, cadralazine, camptothesin, canthaxanthin, captopril, carbamazepine, carboprost, cefalexin, cefalotin, cefamandole, cefazedone, cefluoroxime, cefinenoxime, cefoperazone, cefotaxime, cefoxitin, cefsulodin, ceftizoxime, chlorambucil, chromoglycinic acid, ciclonicate, ciglitazone, clonidine, cortexolone, corticosterone, cortisol, cortisone, cyclophosphamide, cyclosporin A and other cyclosporins, cytarabine, desocryptin, desogestrel, dexamethasone esters such as the acetate, dezocine, diazepam, diclofenac, dideoxyadenosine, dideoxyinosine, digitoxin, digoxin, dihydroergotamine, dihydroergotoxin, diltiazem, dopamine antagonists, doxorubicin, econazole, endralazine, enkephalin, enalapril, epoprostenol, estradiol, estramustine, etofibrate, etoposide, factor ix, factor viii, felbamate, fenbendazole, fenofibrate, fexofenedine, flunarizin, flurbiprofen, 5-fluorouracil, flurazepam, fosfomycin, fosmidomycin, furosemide, gallopamil, gamma interferon, gentamicin, gepefrine, gliclazide, glipizide, griseofulvin, haptoglobulin, hepatitis B vaccine, hydralazine, hydrochlorothiazide, hydrocortisone, ibuprofen, ibuproxam, indinavir, indomethacin, iodinated aromatic x-ray contrast agents such as iodamide, ipratropium bromide, ketoconazole, ketoprofen, ketotifen, ketotifen fumarate, K-strophanthin, labetalol, lactobacillus vaccine, lidocaine, lidoflazin, lisuride, lisuride hydrogen maleate, lorazepam, lovastatin, mefenamic acid, melphalan, memantin, mesulergin, metergoline, methotrexate, methyl digoxin, methylprednisolone, metronidazole, metisoprenol, metipranolol, metkephamide, metolazone, metoprolol, metoprolol tartrate, miconazole, miconazole nitrate, minoxidil, misonidazol, molsidomin, nadolol, nafiverine, nafazatrom, naproxen, natural insulins, nesapidil, nicardipine, nicorandil, nifedipine, niludipin, nimodipine, nitrazepam, nitrendipine, nitrocamptothesin, 9-nitrocamptothesin, olanzapine, oxazepam, oxprenolol, oxytetracycline, penicillins such as penicillin G benethamine, penecillin O, phenylbutazone, picotamide, pindolol, piposulfan, piretanide, piribedil, piroxicam, pirprofen, plasminogenici activator, prednisolone, prednisone, pregnenolone, procarbacin, procaterol, progesterone, proinsulin, propafenone, propanolol, propentofyllin, propofol, propranolol, raloxifene, rifapentin, simvastatin, semi-synthetic insulins, sobrerol, somastotine and its derivatives, somatropin, stilamine, sulfinalol hydrochloride, sulfinpyrazone, suloctidil, suprofen, sulproston, synthetic insulins, talinolol, taxol, taxotere, testosterone, testosterone propionate, testosterone undecanoate, tetracane HI, tiaramide HCl, tolmetin, tranilast, triquilar, tromantadine HCl, urokinase, valium, verapamil, vidarabine, vidarabine phosphate sodium salt, vinblastine, vinburin, vincamine, vincristine, vindesine, vinpocetine, vitamin A, vitamin E succinate, and X-ray contrast agents.

In addition, it is also expected that new chemical entities (NCE) and other actives for which the methods of the invention are suitable, and will be created or become commercially available in the future.

The precise quantity of biologically active material will depend on the material, such as a drug, selected. However, the active material is generally present in an amount from 0.02 to 95%, preferably 0.02 to 20% or preferably 0.1 to 75%, by dry weight of the composition of the dosage form.

The fast dissolving solid dosage form of the present invention also comprises at least one matrix forming agent. In the freeze-dried systems of the prior art, gelatin is the most commonly used carrier or structure forming agent due to its wall-forming ability. Gelatin is a water soluble polymer, and as such, when mixed with active pharmaceutical ingredients in water; the increasing viscosity of the solution over time may cause a decreasing solubility of poorly soluble drugs in the mixture, and lead to a suspension of the drug in gelatin matrix. This can cause phase separation to occur; and the drug in amorphous or crystalline forms may not be homogenously dispersed in the matrix, which will eventually affect the dissolution and absorption of the final product.

Applicant has found that other polymer materials suitable for forming a matrix may be selected for specific application in the field of drug delivery, especially for site-specific drug delivery system such as in the oral cavity. Matrix forming agents of the present invention may be selected from the group consisting of: non-mammalian gelatin, dextrin, soy protein, wheat protein, psyllium seed protein, acacia gum, guar gum, agar gum, xanthin gum, polysaccharides; alginates; sodium carboxymethylcellulose; carrageenans; dextrans; pectins; sugars; amino acids; starch; modified starches; carboxymethylcellylose; hydroxypropylmethylcellulose; hydroxypropyl cellulose and methyl cellulose inorganic salts; synthetic polymers; amylopectin, polypeptide/protein or poly-saccharide complexes.

Examples of at least one matrix forming agent that are carbohydrates include mannitol, dextrose, lactose, galactose and trehalose and cyclodexrin. Examples of matrix forming agents that are inorganic salts may be selected from the group consisting of: sodium phosphate, sodium chloride and aluminium silicates. The at least one matrix forming agent may also be an amino acid. Examples of suitable amino acids include glycine, L-alanine, L-aspartic acid, L-glutamic acid, L-hydroxyproline, L-isoleucine, L-leucine and L-phenylalanine.

In a highly preferred embodiment, at least one matrix forming agent is sodium carboxymethylcellulose. When at least one matrix forming agent is sodium carboxymethyl cellulose, the polymer is present in a concentration of from about 0.1% to about 19% by dry weight of the solid dosage form. In a preferred embodiment the sodium carboxymethylcellulose is present in an amount of about 0.1% to about 15% by dry weight of the dosage form. In a highly preferred embodiment of the present invention, the sodium carboxymethyl cellulose is present in an amount of about 0.1% to about 1.0% by dry weight of the solid dosage form.

In another embodiment of the present invention, the fast dissolving dosage form comprises amylopectin as at least one matrix forming agent. Amylopectin is capable of increasing the release of the biologically active agent by promoting formulation disintegration. Amylopectin may be present in the dosage form at a concentration about 2% up to no great than 20% by dry weight of the solid dosage form.

In a highly preferred form of the present invention, amylopectin is present in an amount of about 2% to about 17% dry weight of the dosage form.

To achieve a rapid dissolution of drugs, diluents, may be added as at least one matrix forming material. Diluents include microcrystalline cellulose (e.g., Avicel PH 101® and Avicel PH 102®), lactose, starch and sorbitol. These diluents may be present in the dosage form either alone or as a mixture in different ratios, and may be about 1% to about 80%, preferably about 2% to about 50%, either individually or cumulatively.

In one embodiment of the present invention, the fast dissolving dosage form comprises microcrystalline cellulose as the at least one matrix forming agent. Microcrystalline cellulose may act as a filler and binder in the dosage form of the present invention. Microcrystalline cellulose has the ability to compact with minimum compression pressures, and results in a hard, stable and fast dissolving dosage form. Due to its large surface area and high internal porosity, microcrystalline cellulose is able to absorb and retain large amounts of water, which is desirable in the dosage form of the invention. When the solid dosage form of the present invention comprises microcrystalline cellulose, it is present in an amount of about 1% to about 10%, and preferably from about 1% to about 8% by dry weight of the dosage form.

The effectiveness of the fast dissolving dosage form of the present invention relies on the drug dissolving in a small volume of fluid, such as in the oral cavity, prior to absorption into the systemic circulation. Therefore, the rate of dissolution of the dosage form is important. In a preferred embodiment of the present invention, the dosage form comprises a super-disintegrant as at least one matrix forming material.

In a highly preferred embodiment, the fast dissolving dosage form of the present invention comprises glycine. Glycine is an amino acid with excellent wetting properties and is suitable for the fast dissolving formulation. Low amounts of glycine may be used in the formulation of the present invention to control the dissolution rate of the dosage form. Furthermore, glycine may also be used as an anti-collapsing agent, which maintains the dosage form from shrinking either during the manufacture process or after packing. In one embodiment, the dosage form of the present invention comprises from about 0.5% to about 5% dry weight of the dosage form.

According to another embodiment of the invention, the fast dissolving solid dosage form may include a matrix forming agent such as mannitol. Mannitol is a component that may aid in the crystalline structure and impart hardness of the dosage form. When mannitol is present in the dosage form, it occurs in a concentration of from about 5% to about 80%, and preferably from about 10% to about 60% by dry weight of the dosage form.

In addition, the fast dissolving dosage form of the present invention may include lubricants, such as polyethylene glycol (PEG) 1000, 2000, 4000 and 6000, sodium lauryl sulphate, fats or oils. One advantage of the use of these lubricants is to aid in the removal of the dosage form from the mould. These lubricants may be present in the dosage form either alone or as a mixture in different ratios, and may be between 0.05% to 5%, preferable between 0.1% and 2%, preferable about 1.5%, either individually or cumulatively. In one embodiment, the composition includes between 0.05% to 5% polyethylene glycol 2000, preferably between 0.1% and 2% polyethylene glycol 2000, preferably about 1.5% polyethylene glycol 2000 by dry weight of the dosage form, or as mixtures of the various glycols.

The invention extends, in another aspect thereof, to improve sublingual absorption of weak base compounds, the composition comprising a solid buffer reagent that affords to produce a saliva pH of 7.0 to 7.8 when dissolved in oral cavity. Increasing the pH of the solution of a weak base compound can increase the ratio of unionized to ionized, which will lead to enhanced sublingual absorption. The solid buffer reagent include sodium dihydrogen phosphate dehydrate, sodium hydrogen phosphate, sodium hydrogen carbonate and sodium carbonate, which may be present in the dosage form either alone or as a mixture in different ratios in a concentration of about 0.01% to about 10% by weight of the composition. Preferably, the buffer reagent is sodium carbonate, which may be present in a concentration of about 0.01% to about 10% by weight of the composition, preferably between 0.1% to 1%, most preferably about 0.3%.

When mannitol is present in the dosage form, it occurs in a concentration of from about 5% to about 80%, and preferably from about 10% to about 60% by dry weight of the dosage form.

The composition may, in certain embodiments, include an absorption enhancer. The absorption enhancer may be a polysaccharide and may be positively charged. Preferably, the absorption enhancer is β-cyclodextrin or its derivatives. The β-cyclodextrin or derivative may be present in a concentration of from about 0.01% to about 10% by dry weight of the dosage form, preferably between 0.2% to 2%, and most preferably about 1%.

The fast dissolving solid dosage form of the present invention may comprise flocculating agents to maintain disbursement of the biologically active material evenly dispersed in the matrix during the manufacture process. The flocculating agent may be gums. Preferable, the gum is xanthan gum. The xanthan gum may be present in a concentration of about 0.01% to about 10% by dry weight of the composition, preferably from about 0.2% to 2%, and most preferably about 1%.

To aid dissolution of the biologically active material into the aqueous environment, a surfactant may be added to the solution as a wetting agent. Suitable surfactants include anionic detergents such as sodium lauryl sulfate, dioctyl sodium sulfosuccinate and dioctyl sodium sulfonate. Cationic detergents may be used and include benzalkonium chloride or benzethomium chloride. The list of possible non-ionic detergents includes lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants may be present in the dosage form either alone or as a mixture in different ratios.

Additives which potentially enhance uptake of the compounds are fatty acids such as oleic acid, linoleic acid and linolenic acid.

In order to enhance the aesthetic and taste appeal of the fast dissolving dosage form to the subject, the dosage form may also contain colouring agents, such as FD & C dyes Blue No. 2 and Red No. 40; flavoring agents, such as orange, mint, raspberry and caramel; and/or sweeteners such as aspartame and saccharin.

The fast dissolving solid dosage form of the present invention is suitable for oral administration to a subject. As discussed above, the dosage form comprises at least one biologically active agent or material. The active agent is therefore delivered to the subject via the oral cavity mucosa and into the systemic blood system within a relatively short period of time. In a preferred embodiment, an effective plasma concentration of the biologically active agent is reached within a period of no more than two hours, preferable within 30 minutes, and most preferably within 10 minutes.

Furthermore, an advantage of the present invention is that the fast dissolving solid dosage form completely dissolves within 2 seconds to 60 seconds, preferably 2 seconds to 30 seconds, and most preferably within 2 seconds to 10 seconds after administration of the dosage form. In a highly preferred embodiment of the present invention, there is no residue remaining of the dosage form of the present invention after administration that is detectable by the patient. As such, the subject has no urge to swallow the dosage form.

The subject receiving the fast dissolving dosage form of the present invention may be an animal or human being. When the subject is a human being, it may be an adult or a child, including elderly adults and infants. In particular the subject is a subject that is unable to or has difficulties in swallowing.

The inventors have surprisingly found that the addition of sodium carboxymethylcellulose improves the dissolution rate of the fast dissolving dosage form. When the amount of sodium carboxymethylcellulose is between about 0.1% and 15% by dry weight of the dosage form, the wafer releases the active agent rapidly, without leaving a residue in the oral cavity. In addition, the use of gelatin was avoided by the inventors, and therefore prevents the unwanted residue left in the oral cavity after administration. The addition of lactose and or mannitol was also found to be advantageous in the dosage formulation of the present invention.

Thus, in one embodiment, the present invention provides a rapidly dissolving solid dosage form adapted for the release of a biologically active material in the oral cavity wherein the dosage form comprises: (i) at least one biologically active material and (ii) at least one matrix forming agent, wherein the dosage form substantially dissolves in the oral cavity, wherein the dosage form comprises 0.29% sodium carbonate, 0.59% sodium carboxymethylcellulose, 1.48% PEG 2000, 2.97% glycine, 5.93% microcrystalline cellulose; 14.84% amylopectin, 29.67% lactose and 44.23% mannitol as a dry weight of the solid dosage form, and which does not result in substantial detectable levels of residue left over in the oral cavity of the patient. Applicant also found that PEG 2000 could be replaced with PEG 1000 with the same advantages as the oral dosage form described above.

As discussed above, the medicaments of the present invention may include one or more pharmaceutically acceptable carriers. The use of such media and agents for the manufacture of medicaments is well known in the art. Except insofar as any conventional media or agent is incompatible with the pharmaceutically acceptable material, use thereof in the manufacture of a pharmaceutical composition according to the invention is contemplated.

Pharmaceutical acceptable carriers according to the invention may include one or more of the following examples:
(1) surfactants and polymers, including, however not limited to polyethylene glycol (PEG), polyvinylpyrrolidone, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropylmethyl cellulose phthalate, polyacrylates and polymethacrylates, urea, sugars, polyols, and their polymers, emulsifiers, sugar gum, starch, organic acids and their salts, vinyl pyrrolidone and vinyl acetate; and/or
(2) binding agents such as various celluloses and cross-linked polyvinylpyrrolidone, microcrystalline cellulose; and/or
(3) filling agents such as lactose monohydrate, lactose anhydrous, microcrystalline cellulose and various starches; and/or
(4) lubricating agents such as agents that act on the flowability of the powder to be compressed, including colloidal silicon dioxide, talc, stearic acid, magnesium stearate, calcium stearate, silica gel; and/or
(5) sweeteners such as any natural or artificial sweetener including sucrose, xylitol, sodium saccharin, cyclamate, aspartame, and accsulfame K; and/or
(6) flavouring agents; and/or
(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride; and/or
(8) buffers; and/or
(9) diluents such as pharmaceutically acceptable inert fillers, such as microcrystalline cellulose, lactose, dibasic calcium phosphate, saccharides, and/or mixtures of any of the foregoing; and/or
(10) wetting agents such as corn starch, potato starch, maize starch, and modified starches, croscarmellose sodium, crosspovidone, sodium starch glycolate, and mixtures thereof; and/or
(11) disintegrants; and/or
(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and/or
(13) other pharmaceutically acceptable excipients.

Medicaments of the invention suitable for use in animals and in particular in human beings typically must be sterile and stable under the conditions of manufacture and storage. The medicaments of the invention comprising the biologically active material can be formulated as a solid, a liposome, or other ordered structures suitable to high drug concentration adapted for oral delivery.

Actual dosage strengths of the biologically active material in the medicament of the invention may be varied in accordance with the nature of the biologically active material, as well as the potential increased efficacy due to the advantages of providing and administering the biologically active material. Thus as used herein "therapeutically effective amount" will refer to an amount of biologically active material required to effect a therapeutic response in a subject. Amounts effective for such a use will depend on: the desired therapeutic effect; the potency of the biologically active material; the desired duration of treatment; the stage and severity of the disease being treated; the weight and general state of health of the patient; and the judgment of the prescribing physician.

In another embodiment, the biologically active material may be combined into a medicament with another biologically active material, or even the same biologically active material. In the latter embodiment, a medicament may be achieved which provides for different release characteristics—early release from the biologically active material, and later release from a larger average size biologically active material.

Medicaments of the invention can be orally administered to a subject. Solid dosage forms for oral administration include wafers, capsules, tablets, pills, powders, pellets, films and granules. Further, incorporating any of the normally employed excipients, such as those previously listed, and generally 0.1% to 95% of the biologically active agent, and more preferably at a concentration of 0.1% to 75% will form a pharmaceutically acceptable non-toxic oral administration.

Although the fast dissolving dosage form of the present invention may be administered orally, the oral dosage form of the present invention is also suitable for use with a nebulizer, either jet or ultrasonic, and will typically comprise the dosage form suspended in water. The dosage form of the present invention may also include a buffer and a simple sugar (e.g., for protein stabilization and regulation of osmotic pressure). The nebulizer formulation may also contain a surfactant, to reduce or prevent surface induced aggregation of the compounds caused by atomization of the solution in forming the aerosol.

As described above, the biologically active material can be formulated into a solid dosage form (e.g., for oral, dermal or suppository administration). In this case there may be little or no need to add stabilizing agents since the grinding matrix may effectively act as a solid-state stabilizer.

Therapeutic uses of the medicaments of the invention include pain relief, anti-inflammatory, migraine, asthma, and other disorders that require the active agent to be administered with a high bioavailability. One of the main areas when rapid bioavailability of a biologically active material is required is in the relief of pain. The minor analgesics, such as cyclooxgenase inhibitors (aspirin related drugs) or opioids may be prepared as medicaments according to the present invention.

Treatment of cardiovascular disease may also benefit from biologically active materials according to the invention, such as treatment of angina pectoris and, in particular, molsidomine may benefit from improved bioavailability. Other therapeutic uses of the medicaments of the present invention include treatment of hair loss, sexual dysfunction, or dermal treatment of psoriasis.

According to a further aspect of the present invention, there is provided a method to produce the fast dissolving dosage form of the present invention comprising the steps of combining at least one matrix forming agent with a biologically active material to form a mixture and then freeze drying the mixture to form the solid dosage form. In a preferred embodiment of the present invention, the mixture is measured (by weight or volume) into a preformed plastic or aluminium blister mould (individual dose). The blister mould is placed into a freeze dryer for 24 hours and the resultant solid dosage form (wafer) is then sealed with aluminium or plastics foil to prevent moisture absorption.

In one embodiment of the present invention, the method may require that the pH of the mixture is adjusted to a pH within the range of between 3.0 and 8.0, preferably between 6.4 and 7.8. If required, the pH may be adjusted by using an acid, such as hydrochloric acid, phosphoric acid or citric acid; or a basic compound such as sodium hydroxide, sodium dihydrogen phosphate dehydrate, sodium hydrogen phosphate, sodium hydrogen carbonate and sodium carbonate.

In another embodiment, the method may include the step of using a solvent, such as water. If water is used as a solvent, it is preferable to be removed by freeze drying.

In a further aspect of the present invention, there is provided a kit comprising the fast dissolving oral dosage form wherein the dosage form comprises: (i) at least one biologically active material, and (ii) at least one matrix forming agent, wherein the dosage form substantially dissolves in the oral cavity, and instructions for its use.

The present invention will now be described with reference to the following non-limiting Examples. The description of the Examples is in no way limiting on the preceding paragraphs of this specification, however is provided for exemplification of the methods and compositions of the invention.

EXAMPLES

Example 1

A formulation of the present invention was prepared in accordance with the method and ingredients as set out below in Table 1:

TABLE 1

Compositions of Fast Dissolving Solid Dosage Form Formulation

| Ingredient | Amount (g) | % by weight |
|---|---|---|
| Sodium carbonate BP/USP | 10 | 0.075 |
| Sodium carboxymethylcellulose BP/USP | 20 | 0.149 |
| Polyethylene glycol 2000 BP/USP | 50 | 0.374 |
| Glycine BP/USP | 100 | 0.747 |
| Microcrystalline cellulose BP/USP | 200 | 1.495 |
| Amylopectin BP/USP | 500 | 3.737 |
| Lactose BP/USP | 1000 | 7.474 |
| Mannitol BP/USP | 1500 | 11.211 |
| Purified water BP/USP | 10000 | 74.738 |

Sodium carboxymethylcellulose and amylopectin were added in a portion of purified water by mixing thoroughly with a stirrer. The mixture was then heated to 50° C. for ten minutes to allow dissolving of the polymers. Once the solution cooled down to room temperature, polyethylene glycol 2000, glycine, sodium carbonate, microcrystalline cellulose, lactose and mannitol were added individually, under stirring to obtain a homogenously solution. The viscosity of the solution was measured at 25° C. using a Brookfield Digital Viscometer (Brookfield Engineering Laboratories Inc, MA, USA).

The resulting mixture was transferred by pipette and accurately weighed into pre-formed blister packs, and then transferred into a freezer (−30° C.) for approximately 24 hours. After freezing, the sample was freeze-dried (DYNA-VAC, Australia) for 24 hours. The prepare sample was stored in desiccator over silica gel at a room temperature.

The following additional formulations were prepared by the method as set out above. Essentially Samples 1 to 6 are based on the formulation described above, with the addition of flavour and/or colour agents.

Sample 1. Sample 1 additionally contained a flavour.

| Ingredient | Amount (g) | % by weight |
|---|---|---|
| Sodium carbonate | 1 | 0.08 |
| Sodium carboxymethylcellulose | 2 | 0.15 |
| Polyethylene glycol 2000 | 5 | 0.37 |
| Orange flavor | 10 | 0.74 |
| Glycine | 10 | 0.74 |
| Microcrystalline cellulose | 20 | 1.48 |
| Amylopectin | 50 | 3.71 |
| Lactose | 100 | 7.42 |
| Mannitol | 150 | 11.13 |
| Purified water | 1000 | 74.18 |

Sample 2. Additional contained a flavour and a pH adjuster (citric acid).

| Ingredient | Amount (g) | % by weight |
|---|---|---|
| Sodium carbonate | 1 | 0.07 |
| Sodium carboxymethylcellulose | 2 | 0.15 |
| Citric acid | 5 | 0.37 |
| Polyethylene glycol 2000 | 5 | 0.37 |
| Mint flavor | 10 | 0.74 |
| Glycine | 10 | 0.74 |
| Microcrystalline cellulose | 20 | 1.48 |
| Amylopectin | 50 | 3.70 |
| Lactose | 100 | 7.39 |
| Mannitol | 150 | 11.09 |
| Purified water | 1000 | 73.91 |

Sample 3. Additionally contained flavour and a colouring agent

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Polyethylene glycol 2000 | 5 | 0.37 |
| Grape flavor | 9.9 | 0.74 |
| Glycine | 10 | 0.74 |
| Microcrystalline cellulose | 20 | 1.48 |
| Amylopectin | 50 | 3.71 |
| Lactose | 100 | 7.42 |
| Mannitol | 150 | 11.13 |
| Purified water | 1000 | 74.18 |

Sample 4. Additionally contained flavour, a colouring agent and an absorption enhancer.

| Ingredient | Amount (g) | % by weight |
|---|---|---|
| FD & C blue | 0.1 | 0.01 |
| Sodium carbonate | 1 | 0.07 |
| Sodium carboxymethylcellulose | 2 | 0.15 |
| β-Cyclodextrin | 5 | 0.37 |
| Polyethylene glycol 2000 | 5 | 0.37 |
| Grape flavor | 9.9 | 0.73 |
| Glycine | 10 | 0.74 |
| Microcrystalline cellulose | 20 | 1.48 |
| Amylopectin | 50 | 3.71 |
| Lactose | 100 | 7.42 |
| Mannitol | 145 | 10.76 |
| Deionsed water | 1000 | 74.19 |

Sample 5. Additionally contained a colouring agent and a sweetener

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Aspartame | 5 | 0.37 |
| Polyethylene glycol 2000 | 5 | 0.37 |
| Cherry flavor | 9.9 | 0.73 |
| Glycine | 10 | 0.74 |
| Microcrystalline cellulose | 20 | 1.48 |
| Amylopectin | 50 | 3.71 |
| Lactose | 100 | 7.42 |
| Mannitol | 145 | 10.76 |
| Deionsed water | 1000 | 74.19 |

Sample 6. Additionally contained a colouring agent and a pH adjuster

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Sodium hydrogen carbonate | 5 | 0.37 |
| Polyethylene glycol 2000 | 5 | 0.37 |
| Raspberry flavor | 9.9 | 0.73 |
| Glycine | 10 | 0.74 |
| Microcrystalline cellulose | 20 | 1.48 |
| Amylopectin | 50 | 3.71 |
| Lactose | 100 | 7.42 |
| Mannitol | 145 | 10.76 |
| Deionsed water | 1000 | 74.19 |

Various batches of fast dissolving solid dosage form were then prepared based on the formulation shown in Table 1 and prepared as set out in Example 1 above. The batch number and the ingredients are listed in Table 2.

TABLE 2

Compositions of the Formulations Used for Investigations

| Ingredient | Batch 071501B Amount (g) | Batch 071502B Amount (g) | Batch 0820A Amount (g) | Batch 0820B Amount (g) | Batch 0905MD Amount (g) | Batch 1003FEN Amount (g) |
|---|---|---|---|---|---|---|
| Amylopectin | 1.0 | 1.0 | 1.0 | 0.00 | 1.0 | 0.5 |
| Mannitol | 3.0 | 3.0 | 3.0 | 3.0 | 3.0 | 1.5 |
| Lactose | 2.0 | 2.0 | 2.0 | 2.0 | 2.0 | 1.0 |
| Glycine | 0.2 | 0.2 | 0.5 | 0.3 | 0.2 | 0.1 |
| PEG 2000 | 0.1 | 0.1 | 0.1 | 0.1 | 0.1 | 0.05 |
| Sodium Carboxymethyl cellulose | 0.04 | 0.04 | 0.04 | 0.04 | 0.04 | 0.02 |
| Sodium carbonate | 0 | 0.02 | 0 | 0 | 0.02 | 0.01 |
| Starch | 1.0 | 0 | 0 | 0 | 0 | 0 |

TABLE 2-continued

Compositions of the Formulations Used for Investigations

| Ingredient | Batch 071501B Amount (g) | Batch 071502B Amount (g) | Batch 0820A Amount (g) | Batch 0820B Amount (g) | Batch 0905MD Amount (g) | Batch 1003FEN Amount (g) |
|---|---|---|---|---|---|---|
| Avicel | 0.2 | 0.2 | 0.00 | 0.2 | 0.2 | 0.1 |
| Active pharmaceutical ingredient | 0 | 0 | 0 | 0 | 0.255 midazolam (base) | 0.004 fentanyl citrate (2.5 mg fentanyl base) |
| Purified water | 40 | 40 | 40 | 40 | 40 | 20 |

General Observations

The procedure of Example 1 was repeated, except that polyethylene glycol 1000 was employed instead of polyethylene glycol 2000, to thereby yield a fast dissolving dosage form. Applicant found that there was no significant difference between the use of polyethylene glycol 1000 or polyethylene glycol 2000 (results not shown).

Applicant found the addition of starch resulted in a hard wafer, and was less suitable for the fast dissolving solid dosage form of the present invention.

Uniformity of Weight

The uniformity of the weight of the fast dissolving dosage form (wafer) was tested in accordance with the British Pharmacopoeia (BP) 2009 test. That is, 20 wafers from each of the formulations listed in the above Table 2 were individually weighed, and the average weight and relative standard was calculated. All the prepared wafers from different formulations were within the accepted weight variation from between 0.25 to 2%.

Hardness

The hardness of the dosage formulations listed in Table 2 was also tested. The mechanical strength of tablet is referred to as "hardness". The hardness of the wafer was determined using an Erweka Hardness Tester (Germany). The values of hardness from different formulations ranged from 0.5 to 4.0 kg. It was observed that the hardness of the formulation increased when Avicel was added to the formulation (results not shown).

Friability

The strength of the fast dissolving solid dosage forms (wafers), i.e. their ability to be reduced from a solid substance into smaller pieces was measured. The test was conducted according to BP 2009 method (i.e. friability of uncoated tablets), using the Erweka friability tester (Germany). A sample of 20 wafers was weighed accurately and placed in the apparatus. A rotation time of four minutes at 25 rpm was used. Wafers were removed and reweighed and the percentage weight loss was calculated. It was found that the weight loss of 20 wafters ranged from 8 to 20%. Although this weight loss does not comply with the BP 2009 standard of about 1% weight loss for compressed tablets, there is no such standard for wafers in either the BP or USP monograph.

Moisture Analysis

The moisture content of the wafers was analysed after lyophilisation using the 870 Karl Fisher Titrino Plus (Metrohm Ag, Germany). The results show that the residual moisture content was varied from 1% to 5% for different formulations.

Scanning Electron Microscopic Analysis

Surface morphology and cross-sections of selected wafer formulations were observed using scanning electron microscope (SEM) (Zeiss, EVO 40 XVP, the Oxford Instrument, UK). Cross-section sample were prepared by cutting a thin slice of the wafer using a scalpel. Samples were coated with carbon prior to examination. The accelerating voltage was 10 kV.

The SEM images shown in FIGS. 1 to 6 illustrate the highly porous nature of the wafers on both surface and the inner structure. Clearly, there were morphological differences between different formulations. These differences indicated that the excipients used influence the microstructure of the wafer. In addition, the microstructure might give an explanation about the different hardness, friability, disintegration time, and even the dissolution profiles of wafer prepared from different formulations.

Powder X-Ray Diffraction (XRD)

X-ray diffraction experiments were performed using Bruker D8 Advance (Germany) with detector LynEye. The radiation used was nickel filtered CuKα, which was generated using an acceleration voltage of 40 kV and a cathode current of 40 mA. The samples were scanned over a 2 theta range of 7.5 to 70 degree, and counting time at 1 second per 0.02 degree.

Figure 7:
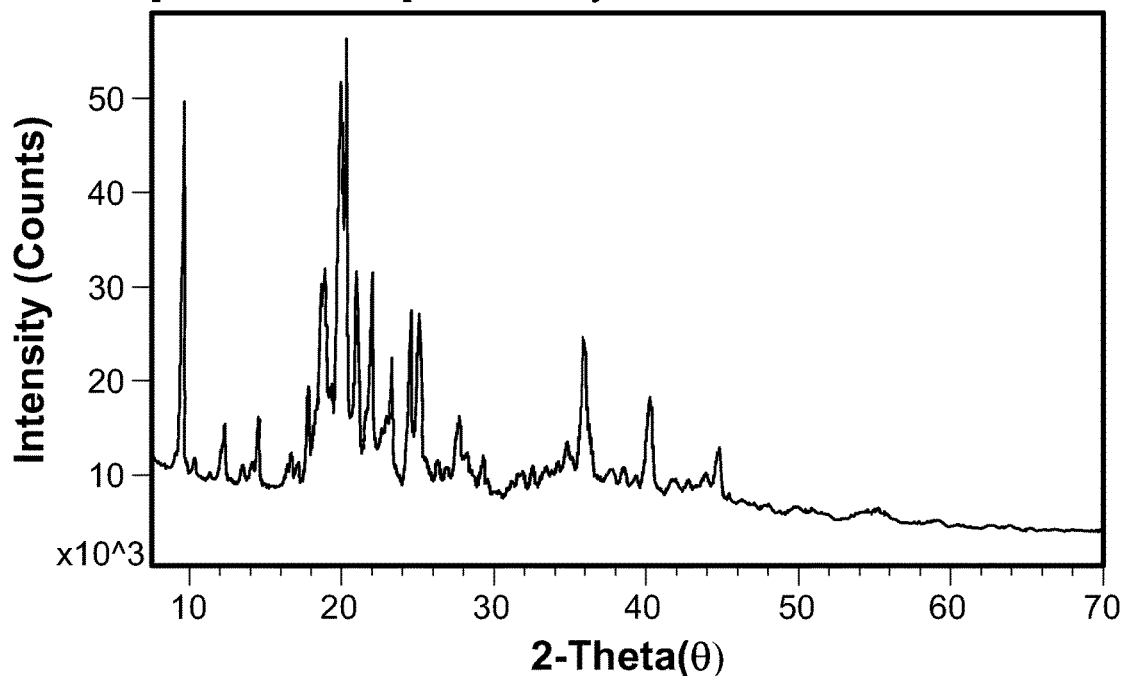
FIG. 7 Powder X-ray diffraction spectra of wafers from batch number 071501A and 071502B.
Figure 7:
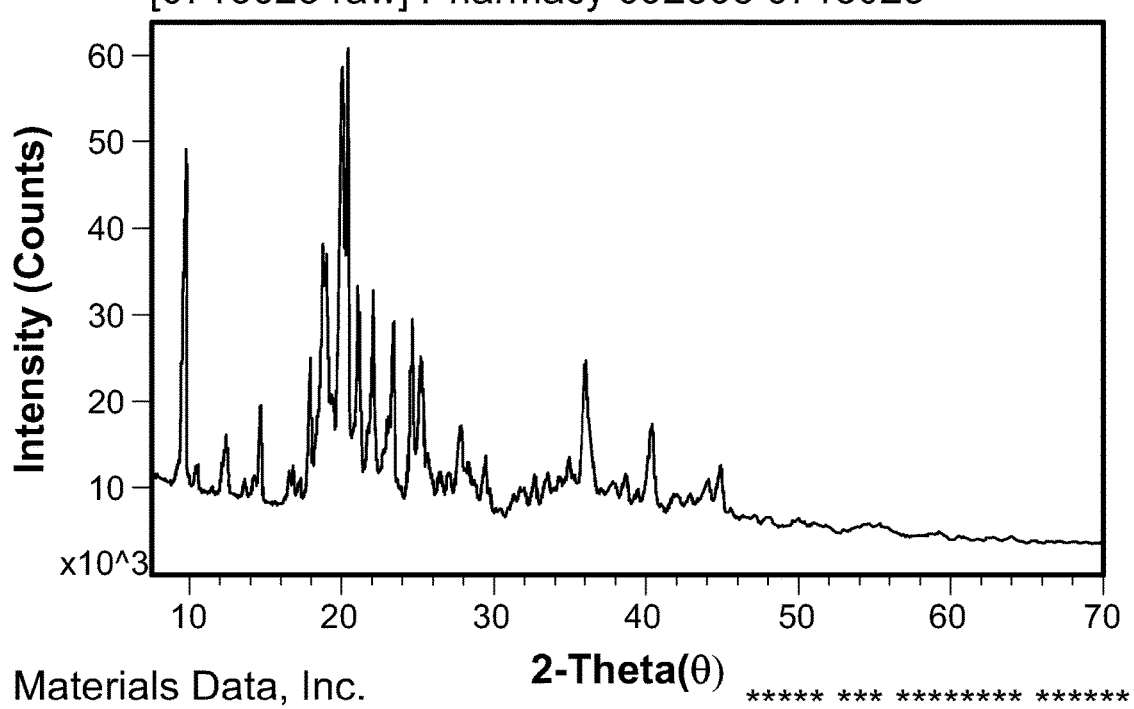
Figure 8:
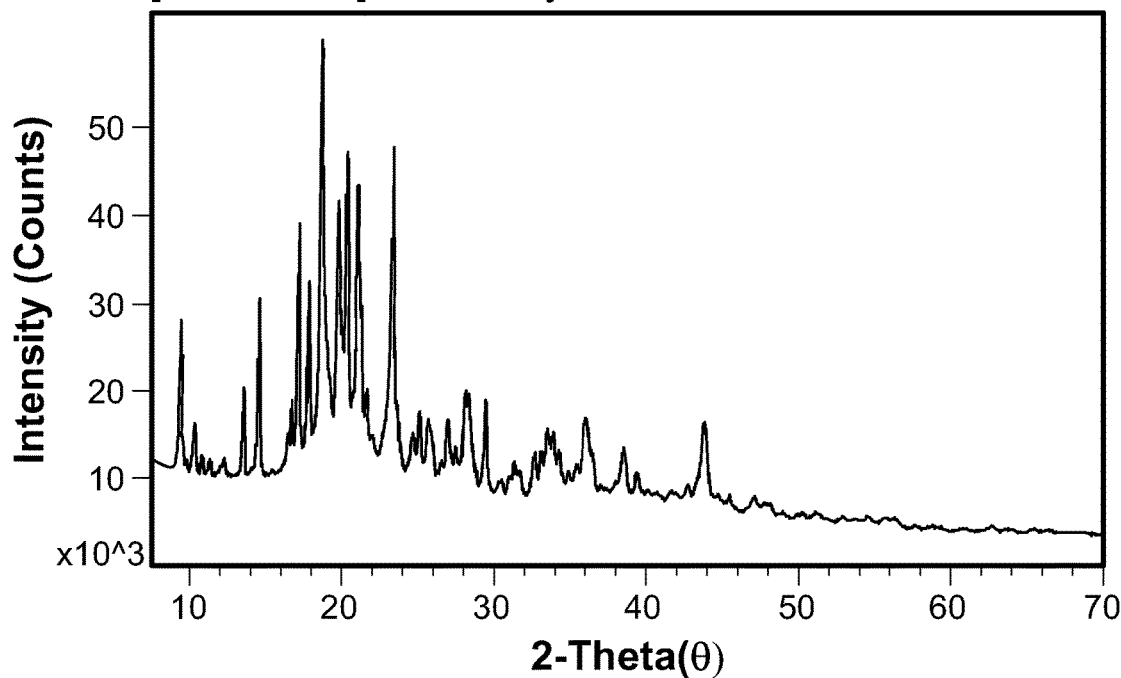
FIG. 8 Powder X-ray diffraction spectra of wafers from batch numbers 0820A and 0820B.
Figure 8:
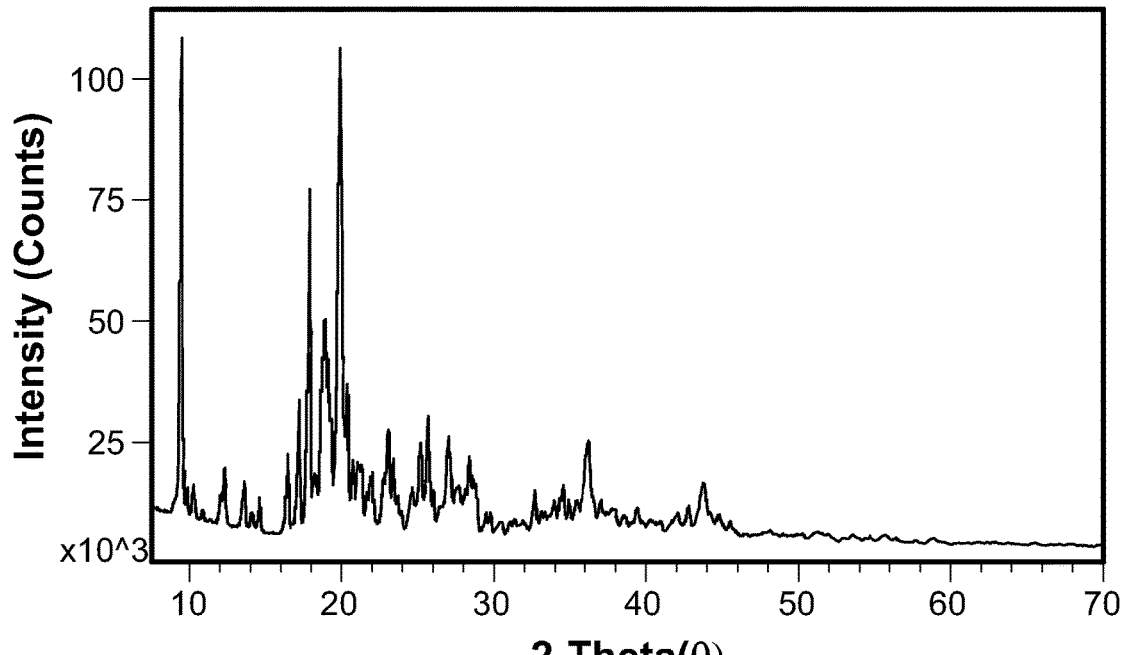
Figure 9:
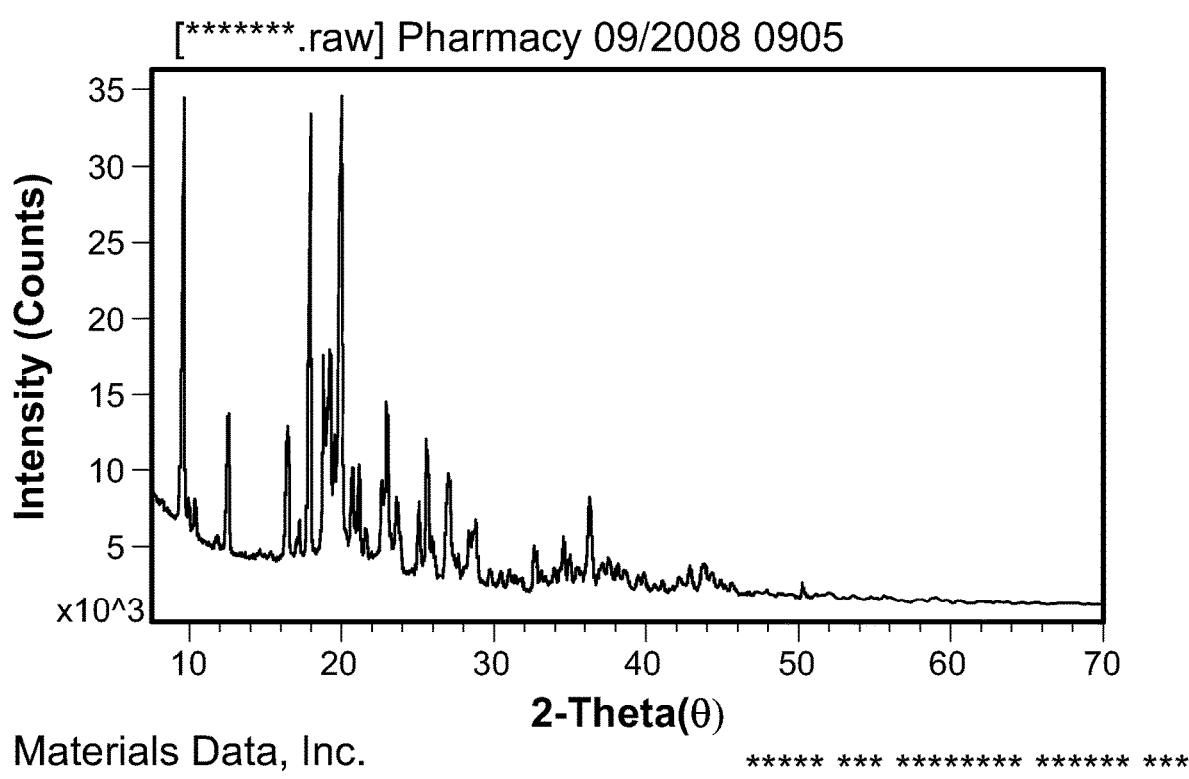
FIG. 9 Powder X-ray diffraction spectrum of wafer from batch number 0905MD.
Figure 10A:
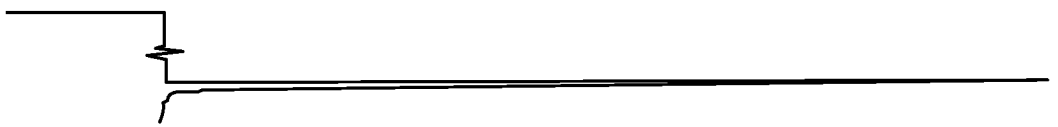
FIG. 10 [A] Typical HPLC chromatograms of standard midazolam sample at 4.05 µg/mL (n=3); [B] Midazolam powder dissolution samples at 1 minute and 5 minutes; [C] Midazolam powder dissolution sample at 10 minutes; [D] Midazolam powder dissolution sample 15 minutes; and [E] standard midazolam sample at 8.1 µg/ml.
Figure 10A:
Figure 10A:
Figure 10B:
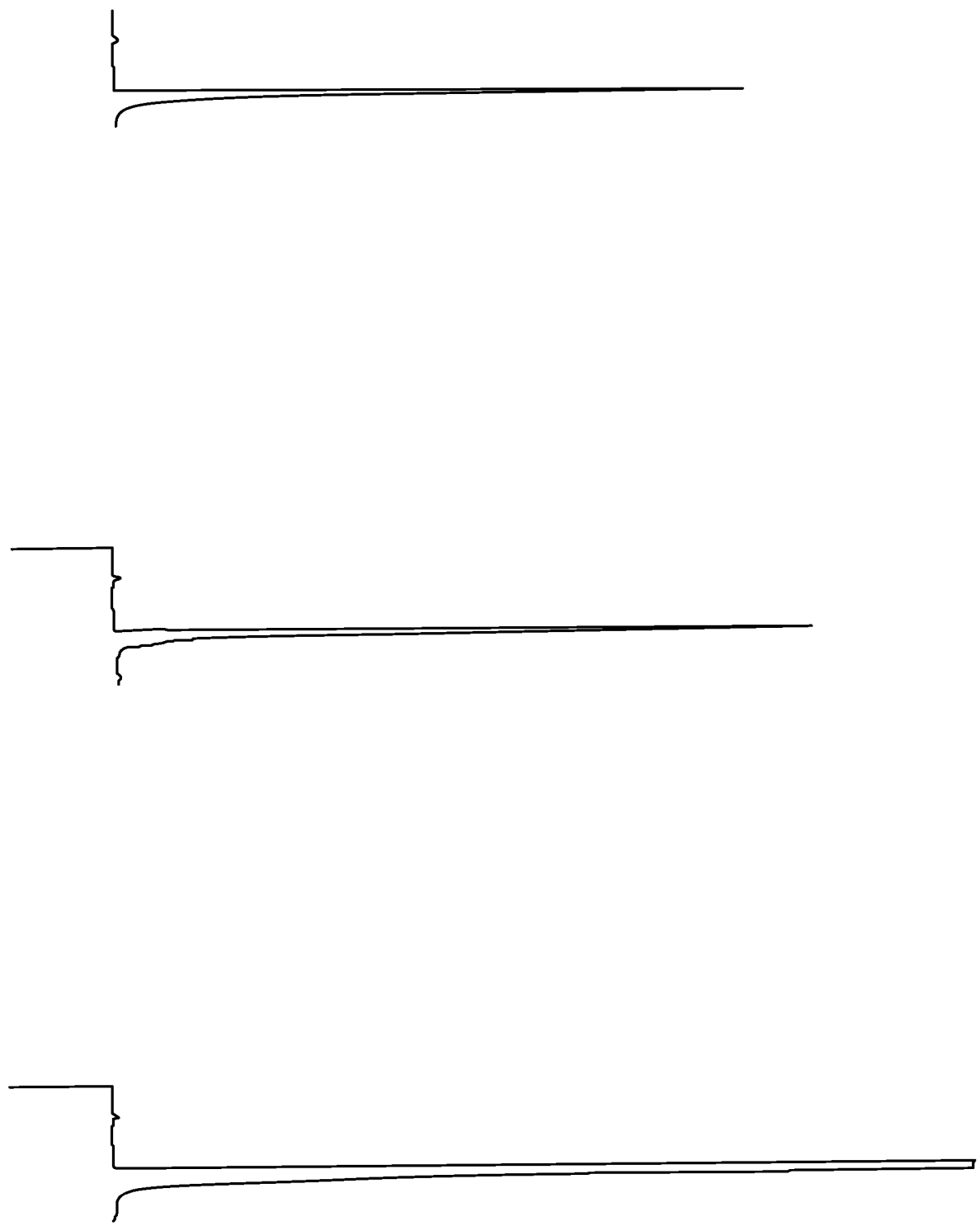
Figure 10C:
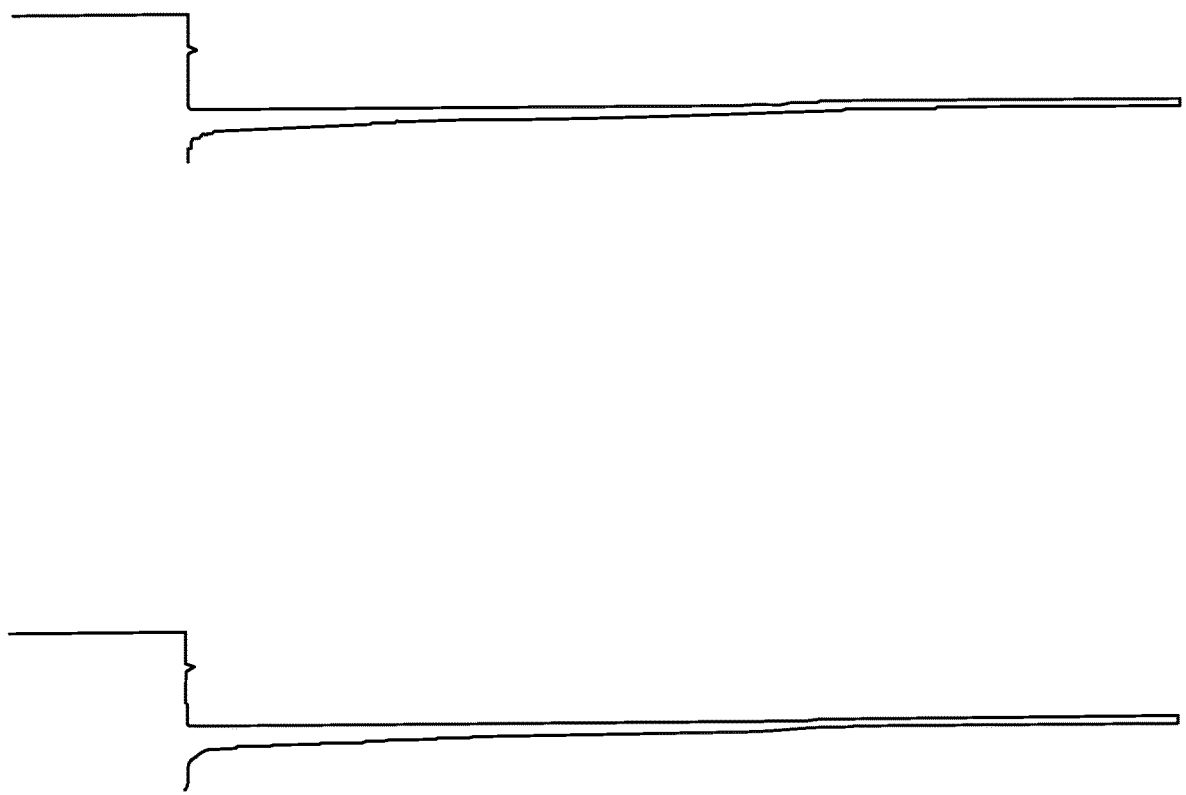
Figure 10D:
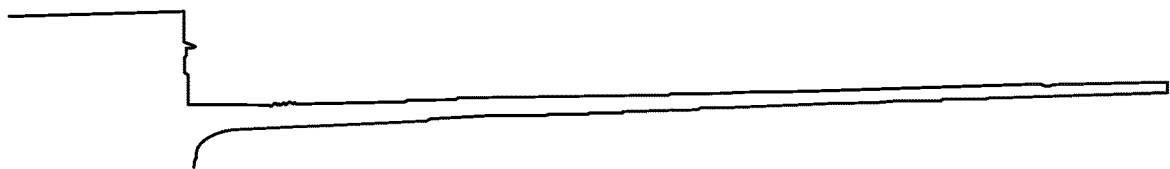
Figure 10D:
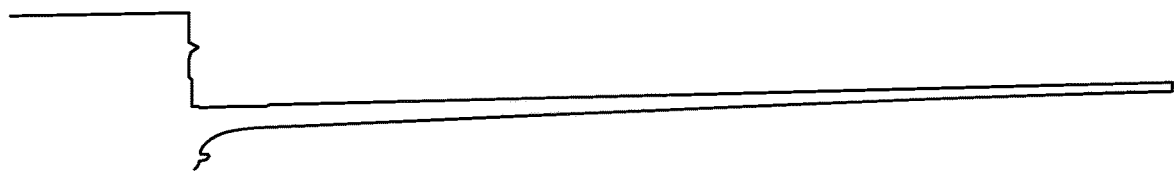
Figure 10E:
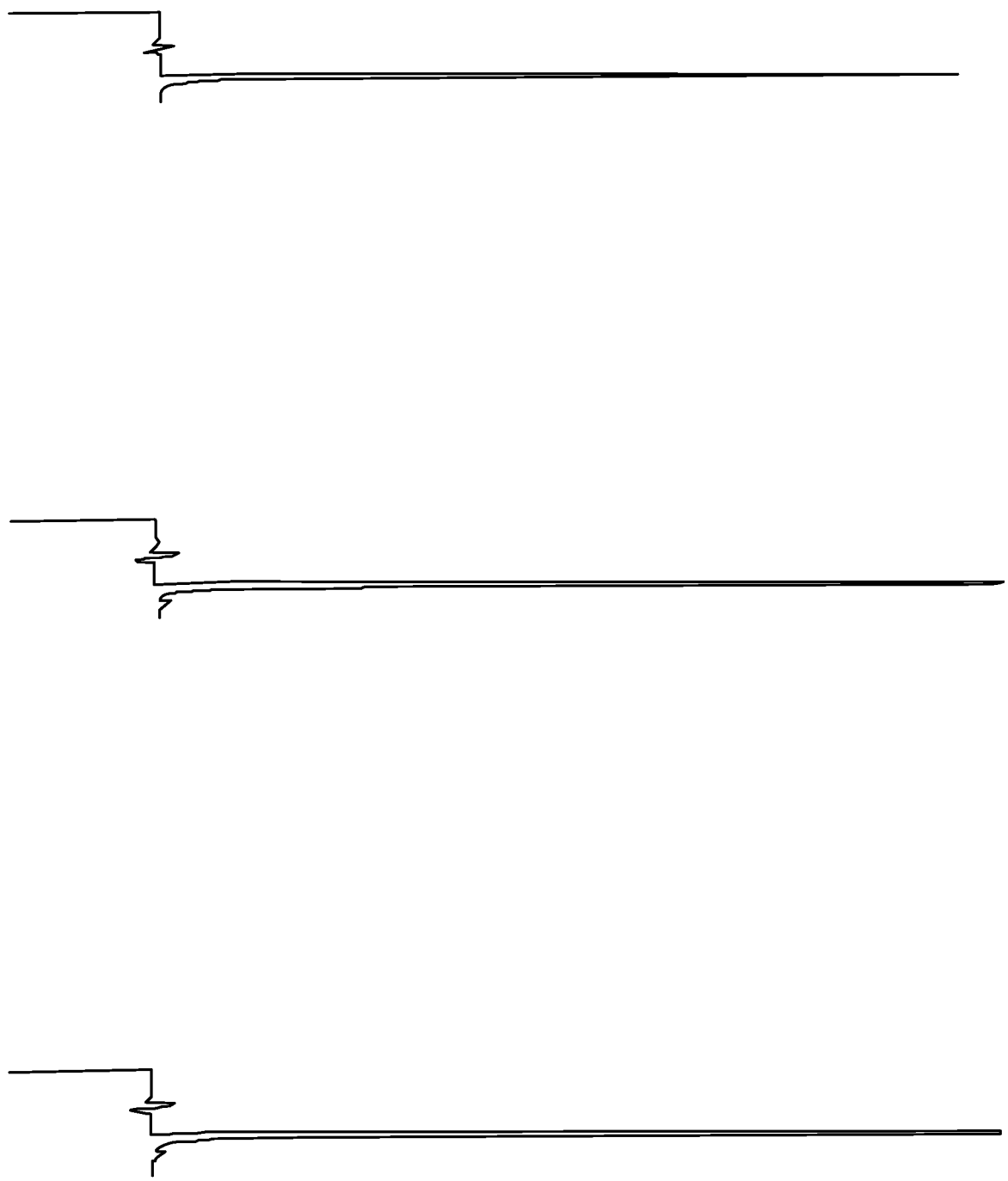
Figure 11:
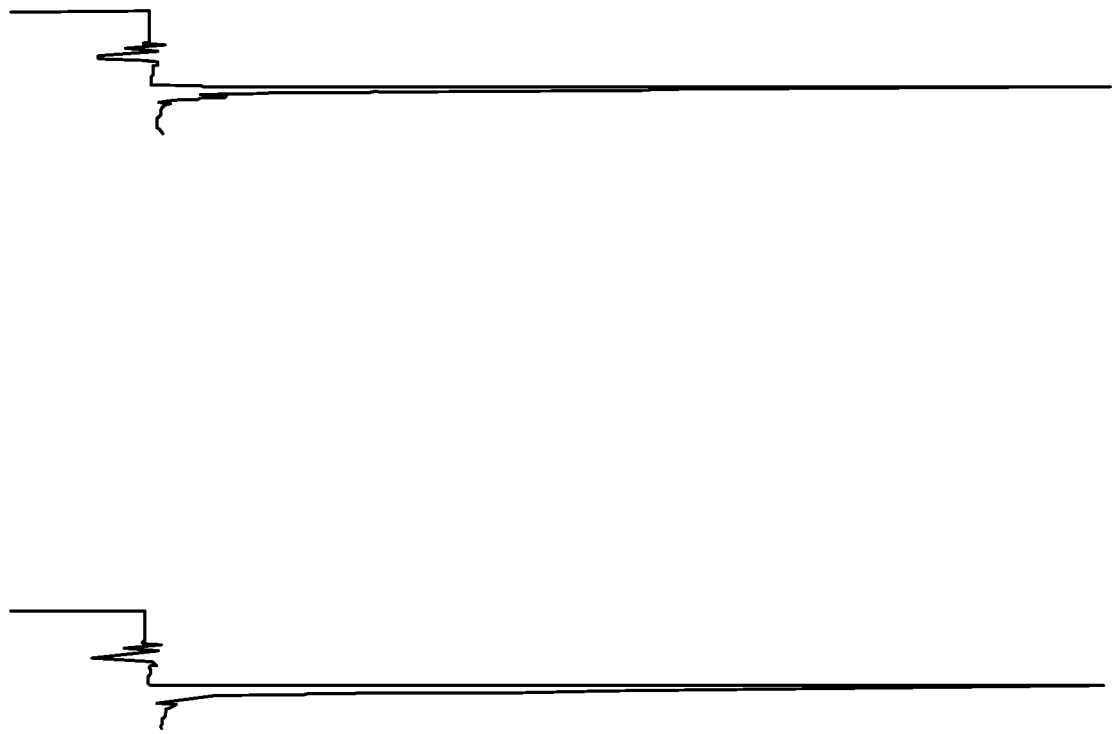
FIG. 11 Typical HPLC chromatograms of dissolution wafer Sample 51 at 45 seconds and 1 minute.
Figure 12:
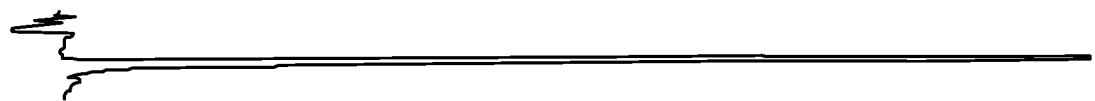
FIG. 12 Typical HPLC chromatogram of dissolution wafer Sample 51 at 10 minutes.
Figure 13:
FIG. 13 Typical HPLC chromatograms of dissolution wafer Sample S2 at 5 and 10 minutes.
Figure 13:
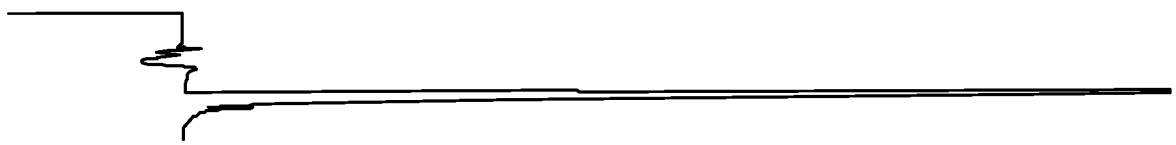
Figure 13:
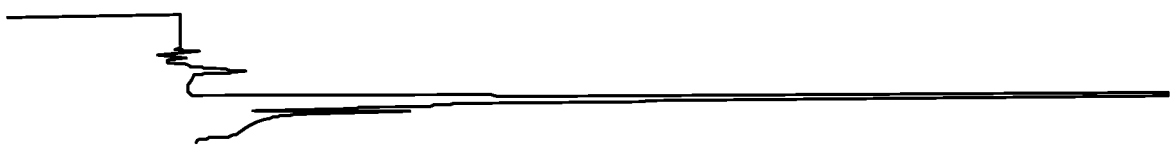
Figure 14:
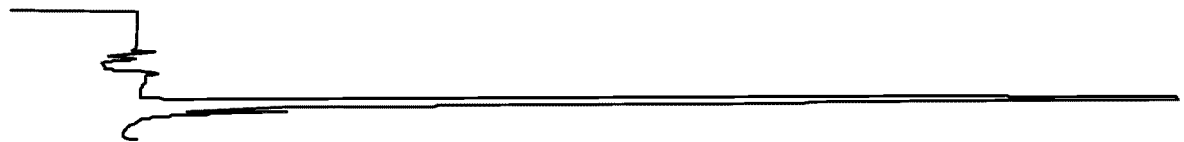
FIG. 14 Typical HPLC chromatograms of dissolution wafer Sample S2 at 30 seconds and 2 minutes.
Figure 14:
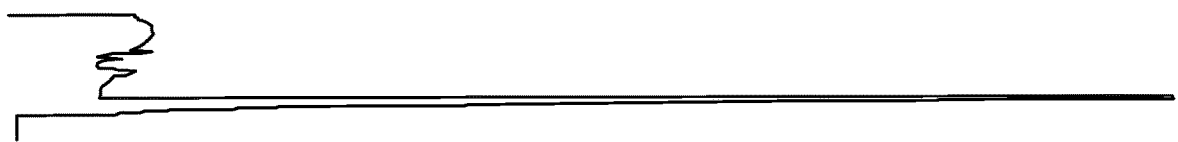
Figure 14:
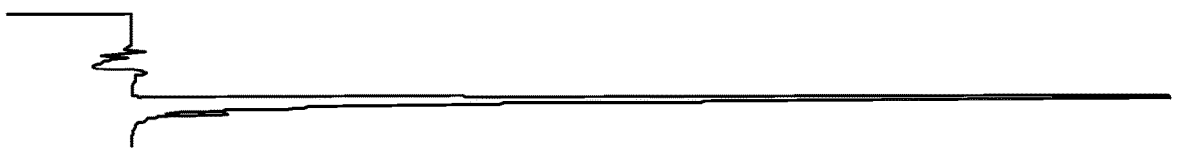
Figure 15:
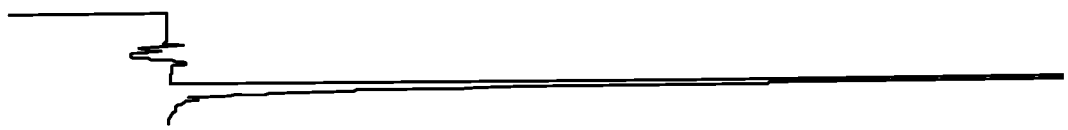
FIG. 15 Typical HPLC chromatograms of dissolution wafer Sample S3 at 20 seconds and at 1 minute.
Figure 15:
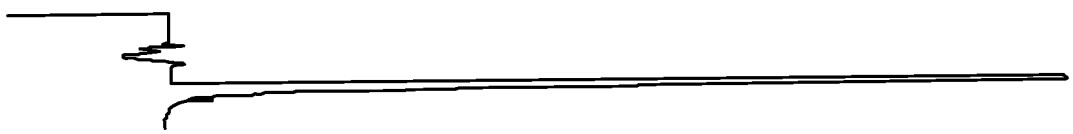
Figure 15:
Figure 16:
FIG. 16 Typical HPLC chromatograms of standard midazolam sample at 1.01 µg/mL.
Figure 16:
Figure 16:

The physical state of the materials in the wafer was evident in the X-ray diffraction spectra. Spectra for three different formulations as prepared in accordance with Table 2 are shown in FIGS. 7 to 9. It was observed that all the powder patterns of wafer prepared are dominated by intense scattering peaks approximately located at 2-theta of 9.58°, 19, 68° and 20.05°, which indicating a crystalline nature. This finding was also supported by the data generated from the SEM (see FIGS. 1-6). Indeed, the excipients used in the formulations, such as glycine, lactose, mannitol and microcrystalline cellulose are crystalline in nature. It was observed that there was minimal physical state change in the solid dispersion.

Disintegration and Dissolution Analysi

Disintegration and dissolution tests were carried out using Apparatus I (BP 2009, Basket apparatus). The Erweka dissolution apparatus (Hesenstamm, Germany) was used for both tests. The temperature of the medium was kept at 37±0.5° C.

For the disintegration test, a wafer was placed in the cylindrical basket and wetted on the underside by contact with distilled water in the cylindrical vessel. The time of total dissolution of each wafer was noted, and a mean value was calculated.

Figure 17:
FIG. 17 Typical HPLC chromatograms of Midazolam powder dissolution sample at 30 seconds.
Figure 17:
Figure 17:
Figure 18:
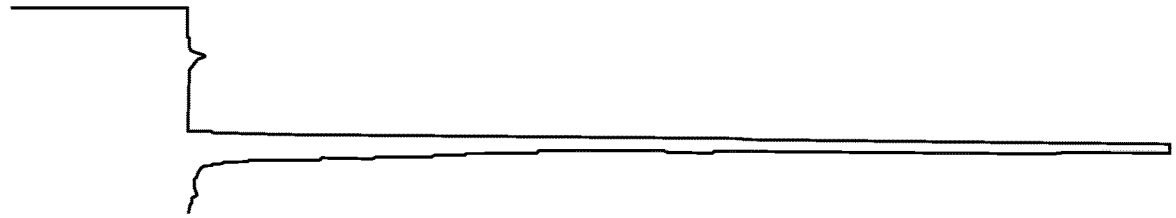
FIG. 18 Typical HPLC chromatograms of dissolution wafer 1 at 1 minute and 5 minutes.
Figure 18:
Figure 19:
FIG. 19 Typical HPLC chromatograms of dissolution wafer 1 at 5, 10 and 15 minutes.
Figure 19:
Figure 19:
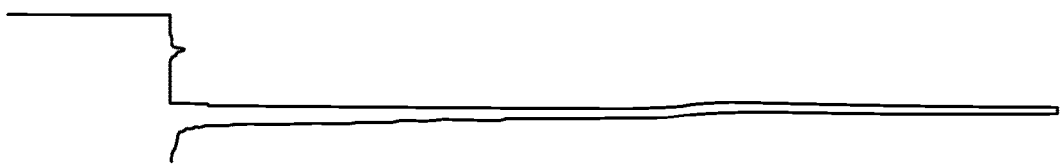
Figure 20:
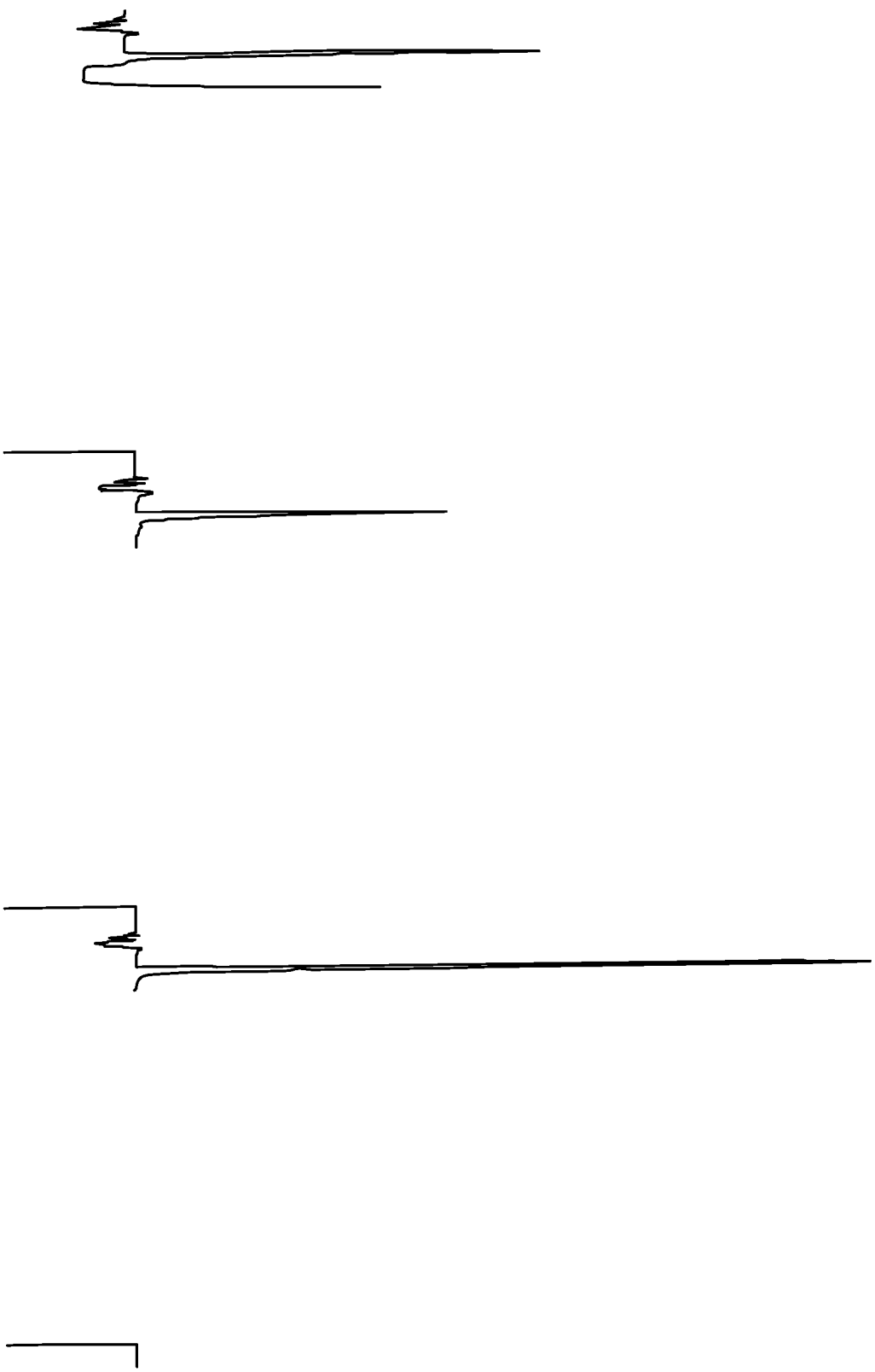
FIG. 20 Typical HPLC chromatogram of drug loading test wafer sample No. 1.
Figure 21:
FIG. 21 Typical HPLC chromatograms of dissolution wafer 2 at 30 seconds.
Figure 21:
Figure 22:
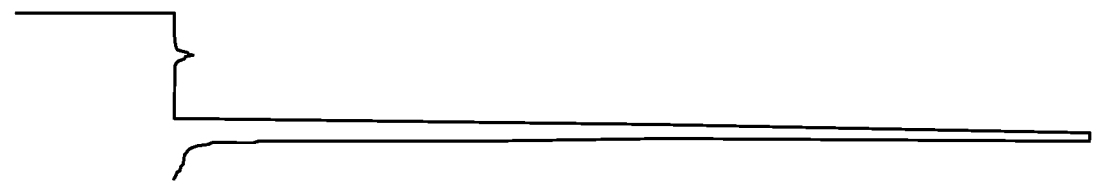
FIG. 22 Typical HPLC chromatograms of dissolution wafer 2 at 1 minute and 5 minutes.
Figure 22:
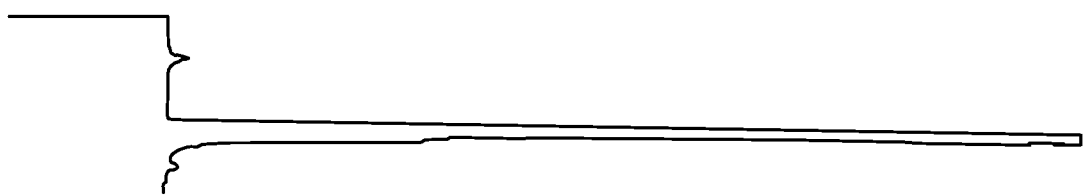
Figure 23:
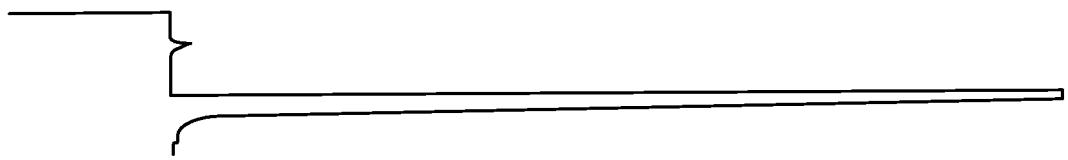
FIG. 23 Typical HPLC chromatograms of dissolution wafer 2 at 10, 15 and 30 minutes.
Figure 23:
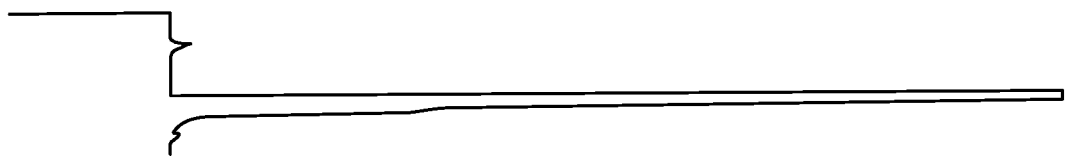
Figure 23:
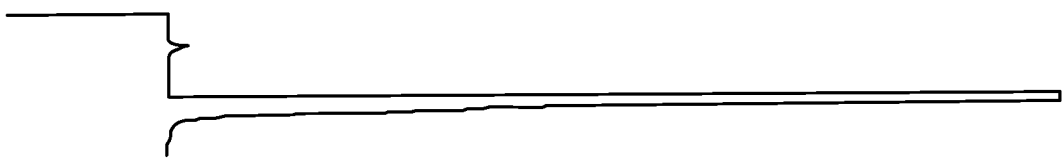
Figure 24:
FIG. 24 Typical HPLC chromatograms of drug loading test wafer sample No. 2.
Figure 24:
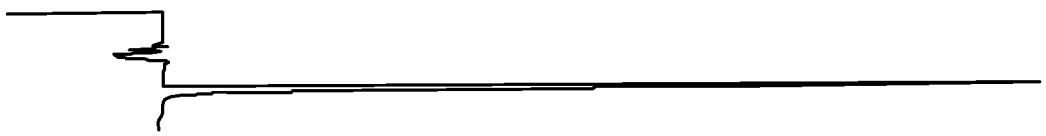
Figure 24:
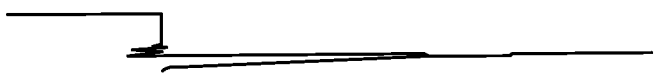
Figure 25:
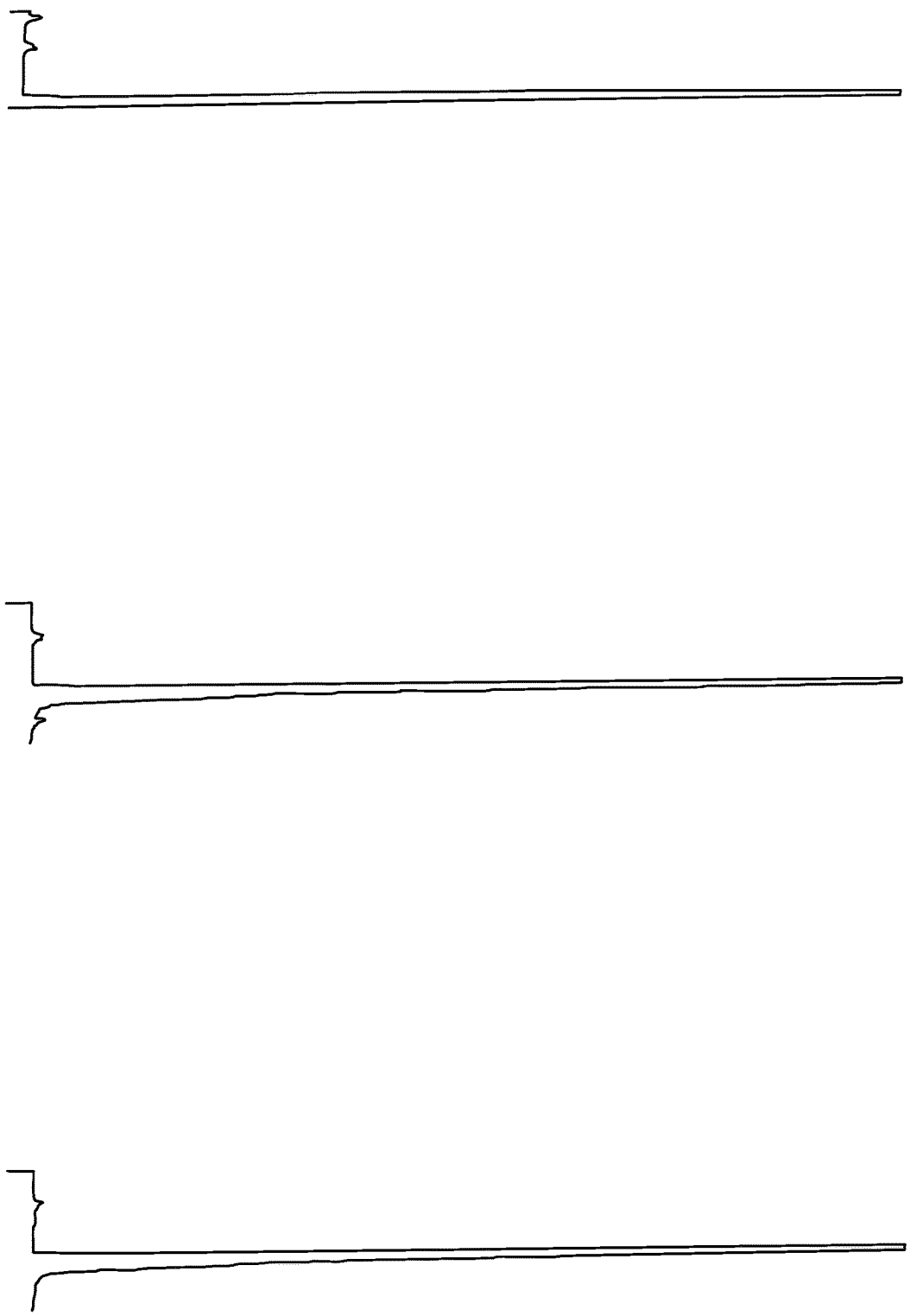
FIG. 25 Typical HPLC chromatograms of dissolution wafer 3 at 30 seconds.
Figure 26:
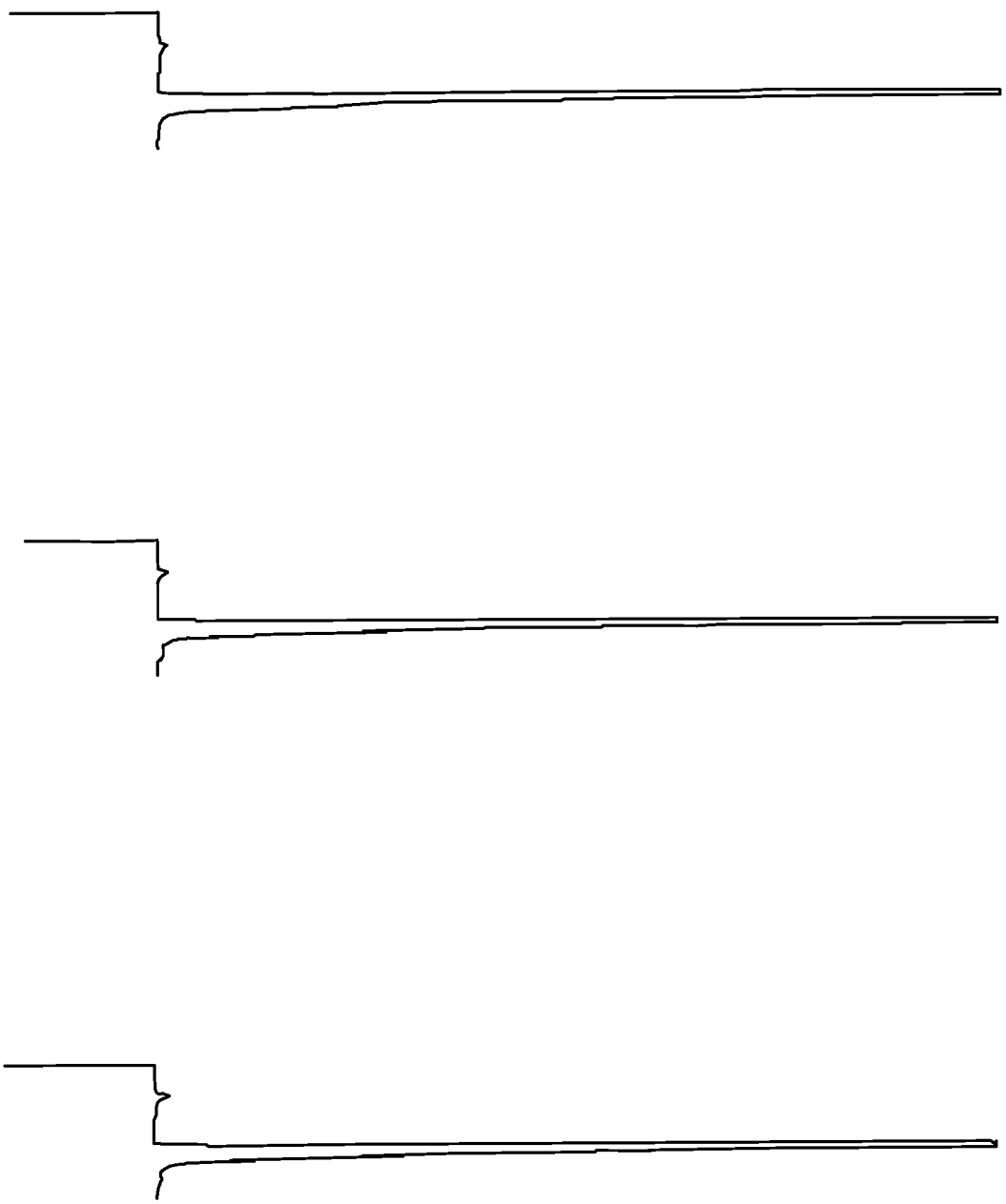
FIG. 26 Typical HPLC chromatograms of dissolution wafer 3 at 1 minute and 5 minutes.
Figure 27:
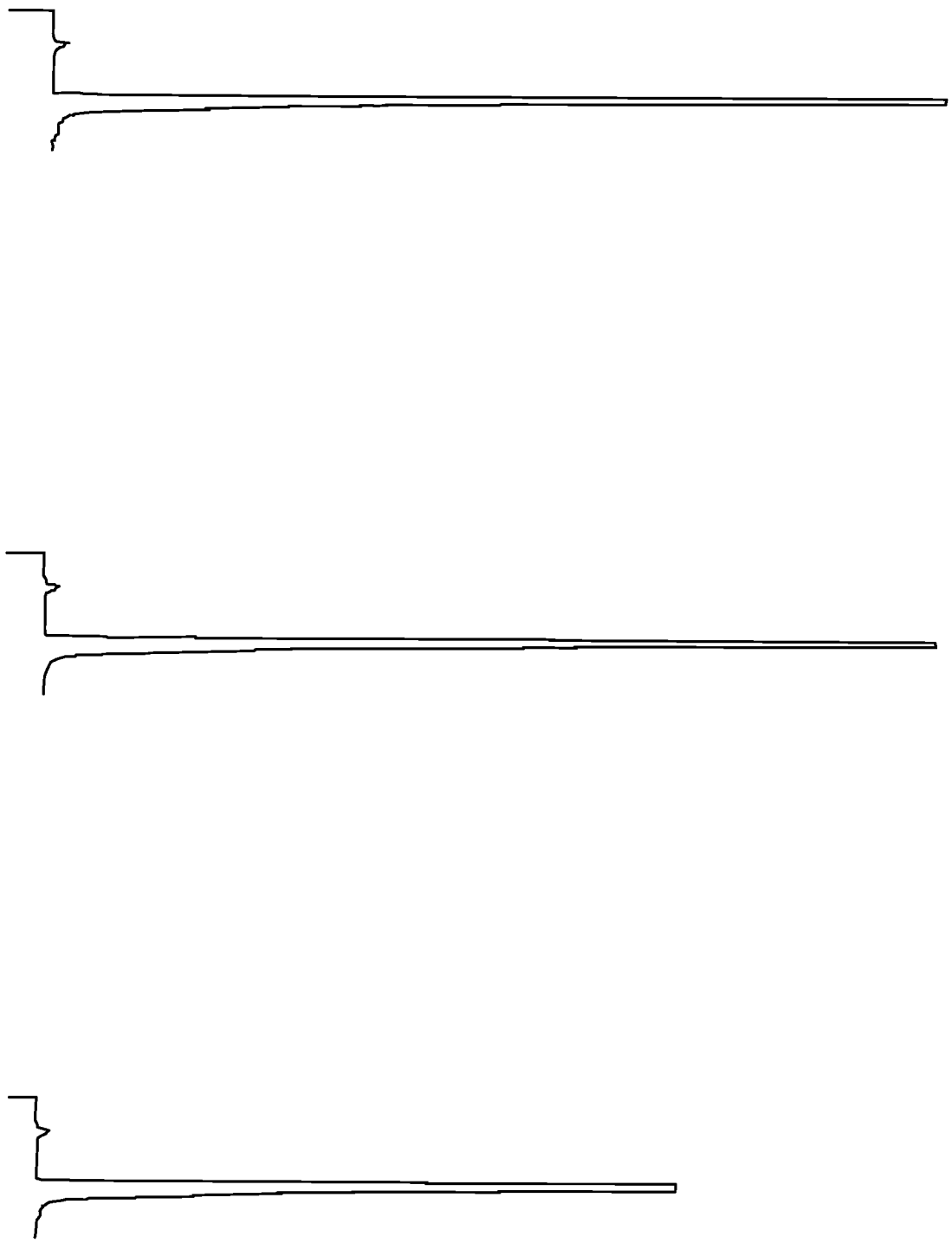
FIG. 27 Typical HPLC chromatograms of dissolution wafer 3 at 10 and 15 minutes.
Figure 28:
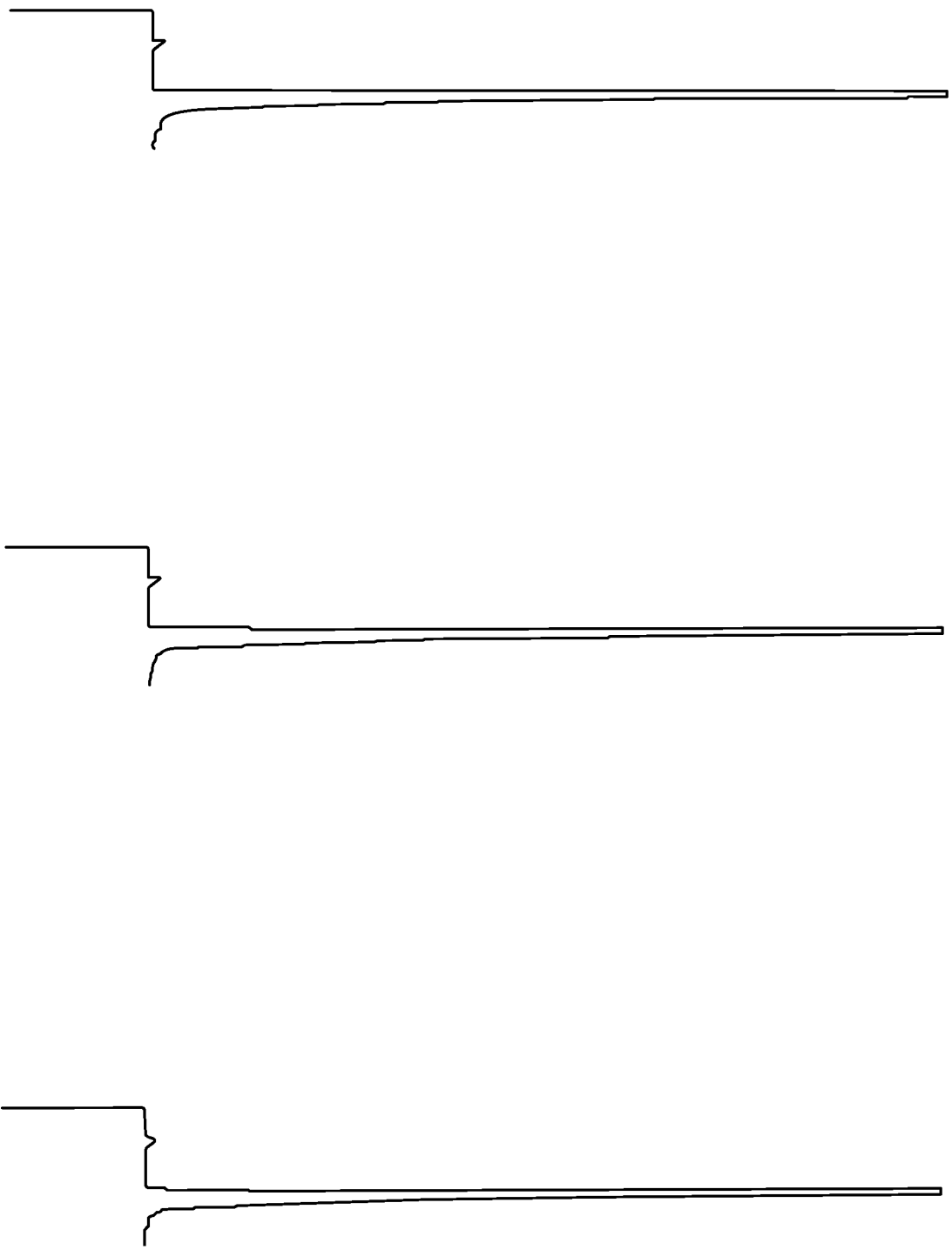
FIG. 28 Typical HPLC chromatograms of dissolution wafer 3 at 30, 45 and 60 minutes.
Figure 29:
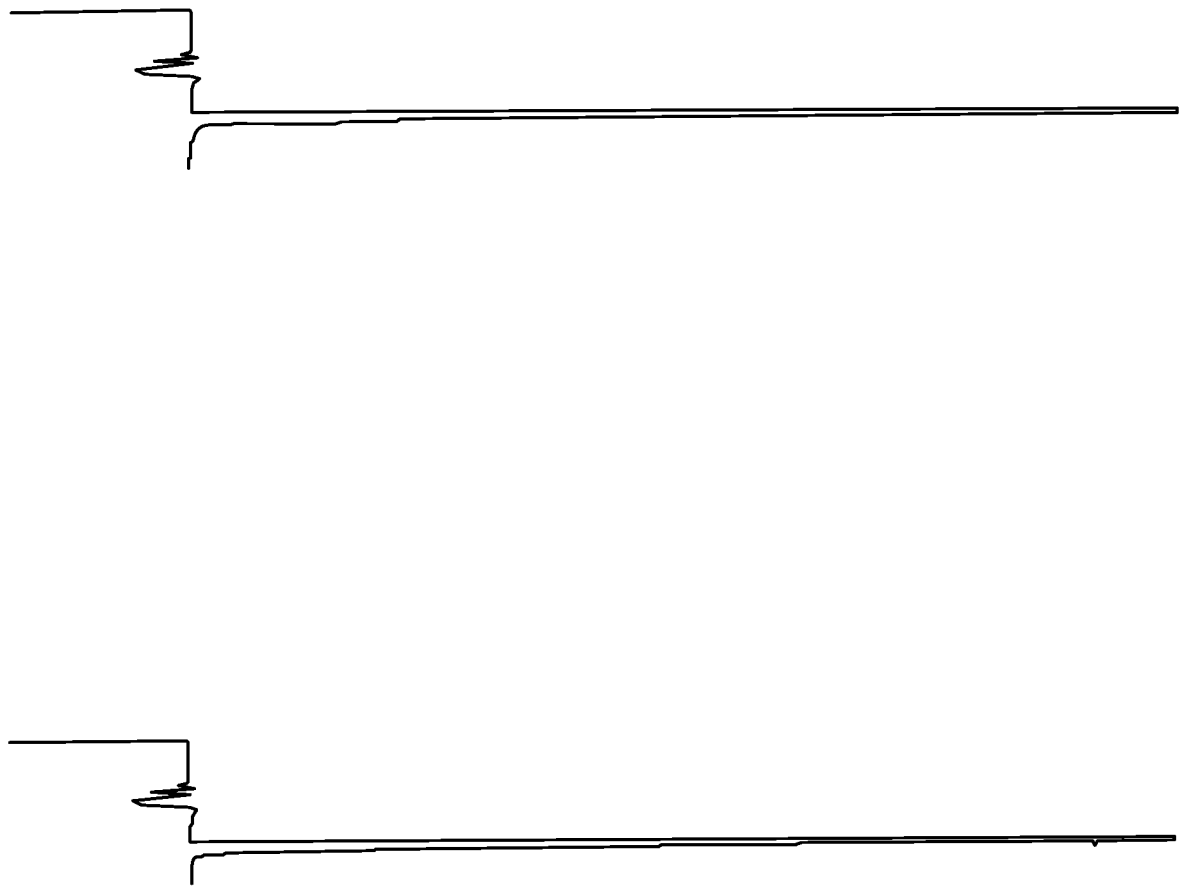
FIG. 29 Typical HPLC chromatograms of drug loading test wafer sample No. 3.

For the dissolution testing: a wafer (Batch 0905MD) containing midazolam as a model drug was used to determine the mechanism of drug release from the system following the both BP basket and USP paddle methods (see FIG. 17). Dissolution medium was 500 mL phosphate buffer solution (pH value is closed to saliva fluid at 6.8), with a paddle rotation speed at 75 rpm. At given interval (e.g., 0.5, 1, 2, 3, 5 10 15, 20 and 30 min), 2 mL of solution was sampled and replaced with an equal volume of fresh medium to maintain a constant total volume. Samples were filtered through a 0.2 µm Millipore filter. The drug released was measured by HPLC.

The HPLC system consisted of a Waters 1525 pump, a Waters Symmetry $C_{18}$ column (5 µm, 150×4.6 mm), and Waters UV 484 detector. The mobile phase was acetonitrile: 10 mM ammonium acetate buffer (40:60, v/v, pH 4.10) and the flow rate was 1.2 ml/min at ambient temperature. The peaks were recorded at 220 nm, and the limit of quantitation was approximately 1 ng/ml. The calibration curve for the concentrations 1-32.4 µg/mL (six-point calibration) was linear [y=870714x+52057 (r=0.9998), y representing the peak area of midazolam and x the concentration of the samples].

Figure 30:
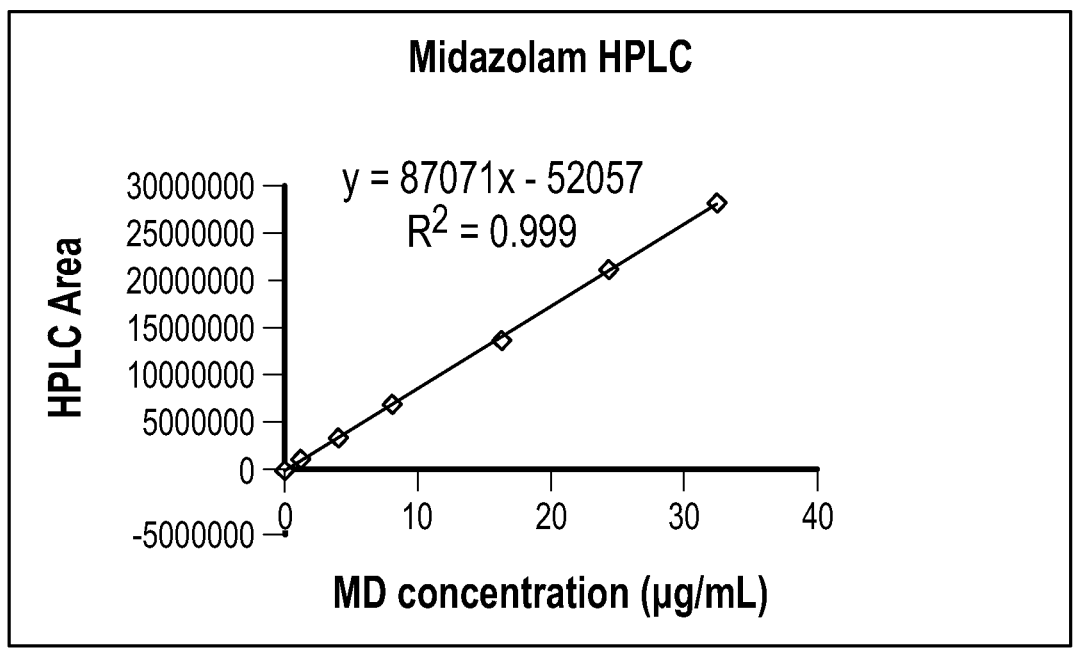
FIG. 30 Standard HPLC calibration curve of midazolam (1 to 32.4 µg/mL).
Figure 31:
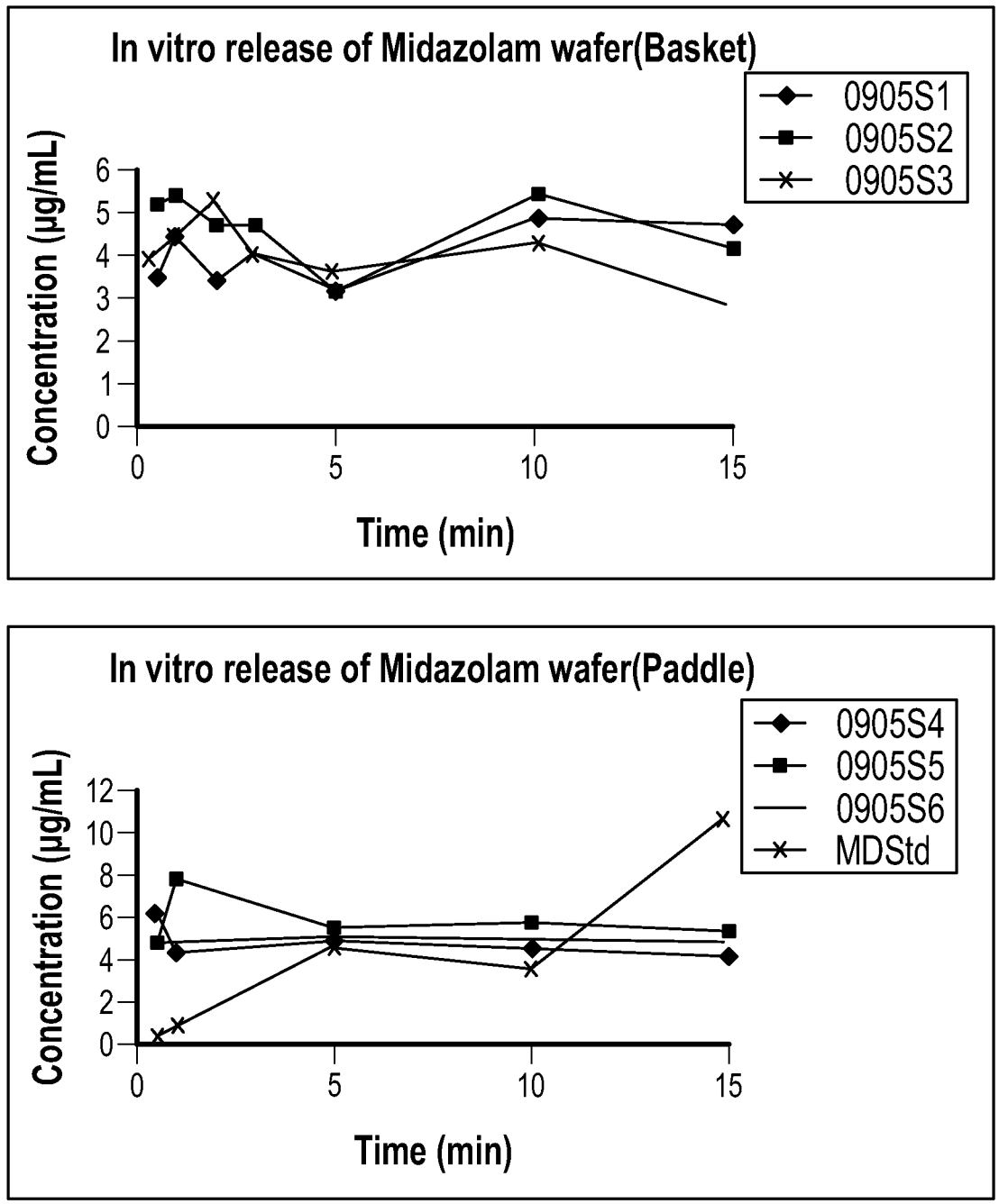
FIG. 31 Cumulative concentration of midazolam released from wafer and midazolam powder in phosphate buffer solution (pH 6.8) at 37° C.

A standard HPLC calibration curve for Midazolam is shown in FIG. 30. The results as shown in FIG. 31 demonstrate that the average disintegration times were less than 15 seconds; and the dissolution studies also indicated a fast release rate of midazolam, Almost 75% of midazolam had dissolved in one minute. The raw midazolam powder was considerably slower. This may indicate the changing of midazolam crystal form in the wafer, which was also evident in the X-ray. The X-ray spectrum pointed to an amorphization of midazolam during the freeze-drying process.

The results of the HPLC analysis on various samples of the formulation as prepared in accordance with Table 1 are shown in FIGS. 11 to 29. FIGS. 10 A to 10 E illustrate the HPLC of standard midazolam sample, and midazolam powder dissolution samples. FIGS. 11 to 16 are HPLC chromatograms of dissolution wafer samples 1 to 3 (S1, S2 and S3, BP basket method). Briefly, the samples 1, 2 and 3 were prepared according to Table 1 and are triplicate samples of the same formulation. FIG. 17 illustrates the HPLC chromatogram of Batch 0905MD, which contains midazolam as a model drug.

FIGS. 18 to 29 reflect the HPLC chromatograms of another three dissolution wafer samples (USP paddle methods). As discussed above, the dissolution rate of the wafer containing test drug midazolam was measured. Samples were taken at 0.5 minute, 1 minute, 5, minutes, 10 minutes and 15 minutes.

The results of wafers 1 to 3 (Batch 0905MD) are shown over these time limits in FIGS. 18 to 29. A drug loading test was also conducted for another three wafers (Batch 0905MD).

It was shown that the wafers of the present invention were able to completely dissolve in about 15 seconds and did not leave behind any residue.

A wafer (Batch 1003FEN) containing fentanyl as a model drug was used to determine the mechanism of drug release from the system following the BP basket method. The dissolution rates of the wafer were determined in a small volume (10 mL phosphate buffer solution, pH 6.8) with a basket rotation speed at 50 rpm. At given interval (e.g., 0.5, 1, 2, 3, 4, 5, 7, 10 and 15 min), 0.5 mL of solution was sampled and replaced with an equal volume of fresh medium. The drug released was measured by HPLC.

Figure 32:
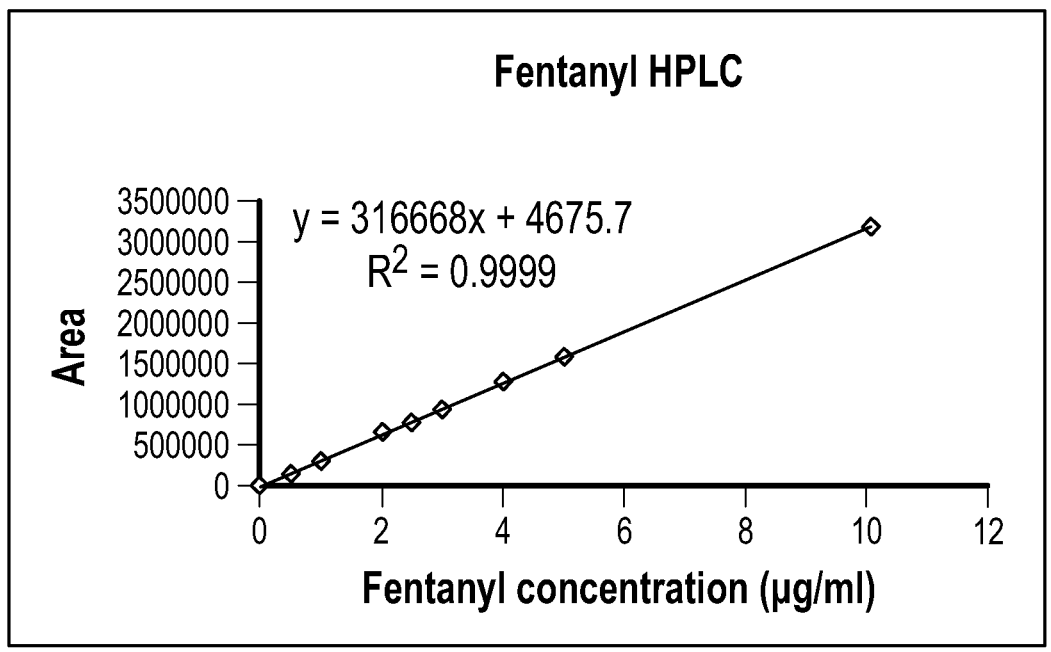
FIG. 32 Standard HPLC calibration curve of fentanyl (0.5 to 10 µg/mL).

The mobile phase was methanol: 0.4% phosphoric acid (50:50, v/v, pH 2.3) and the flow rate was 1.2 ml/min at ambient temperature. The monitoring wavelength was at 210 nm. The calibration curve for the concentrations 0.5-10 µg/mL (eight-point calibration) was linear [y=316668x+4675.7, (r=0.9999), y representing the peak area of fentanyl and x the concentration of the samples]. The assay standard curve is shown in FIG. 32.

Figure 33:
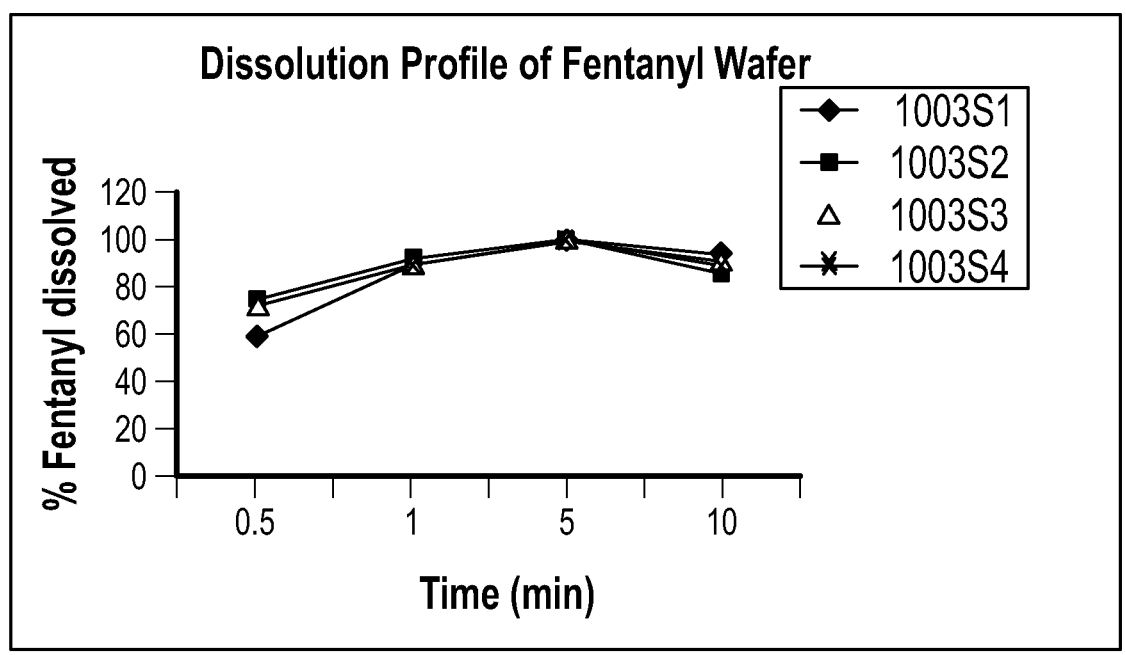
FIG. 33 Dissolution profiles of fentanyl wafer in phosphate buffer solution (pH 6.8) at 37° C., (n=4).
Figure 34A:
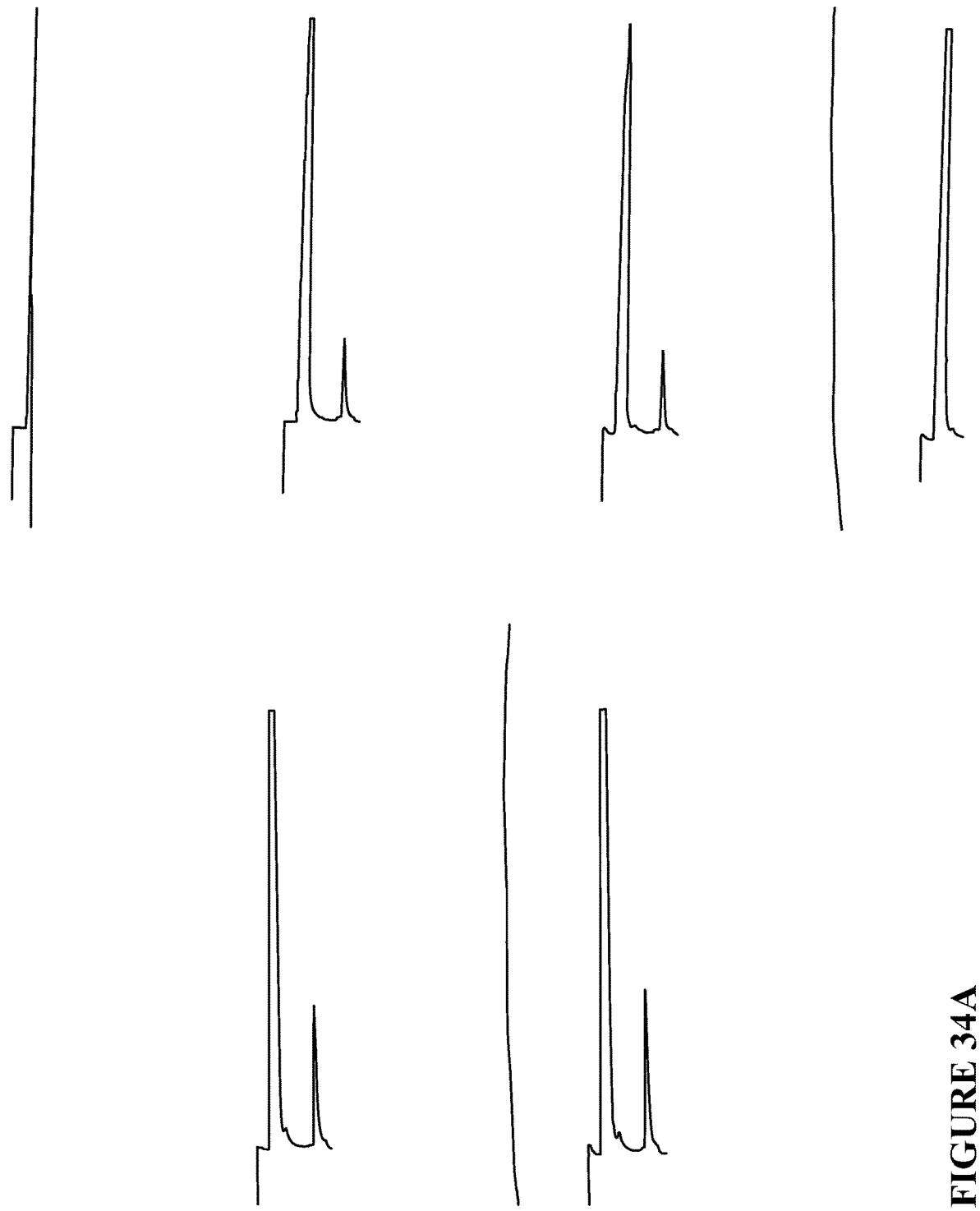
FIG. 34 A to E Typical HPLC chromatograms of dissolution samples 1 to 3 of fentanyl wafers at sampling times of 0.5, 1, 5, 10, 15 and 20 minutes.
Figure 34B:
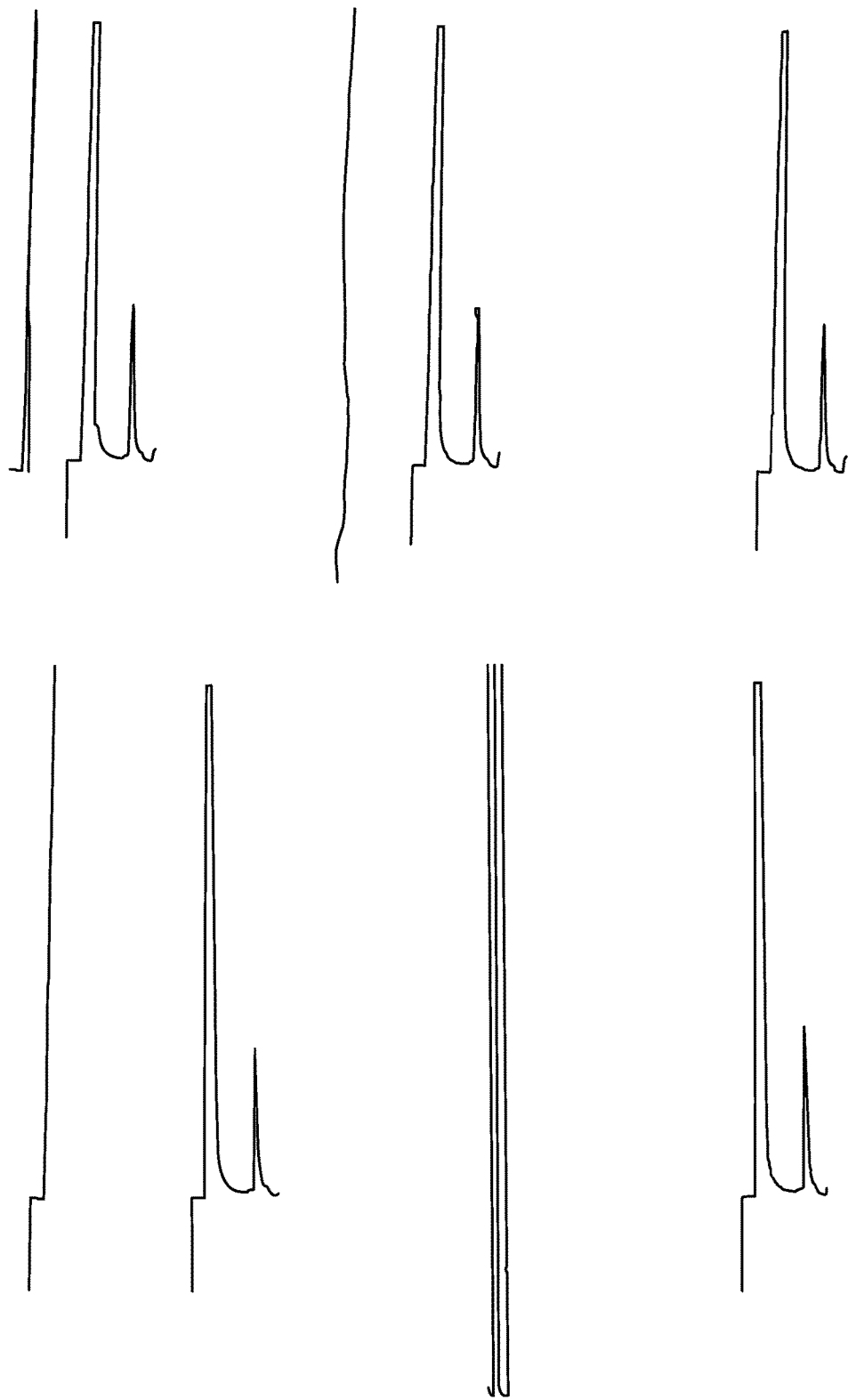
Figure 34C:
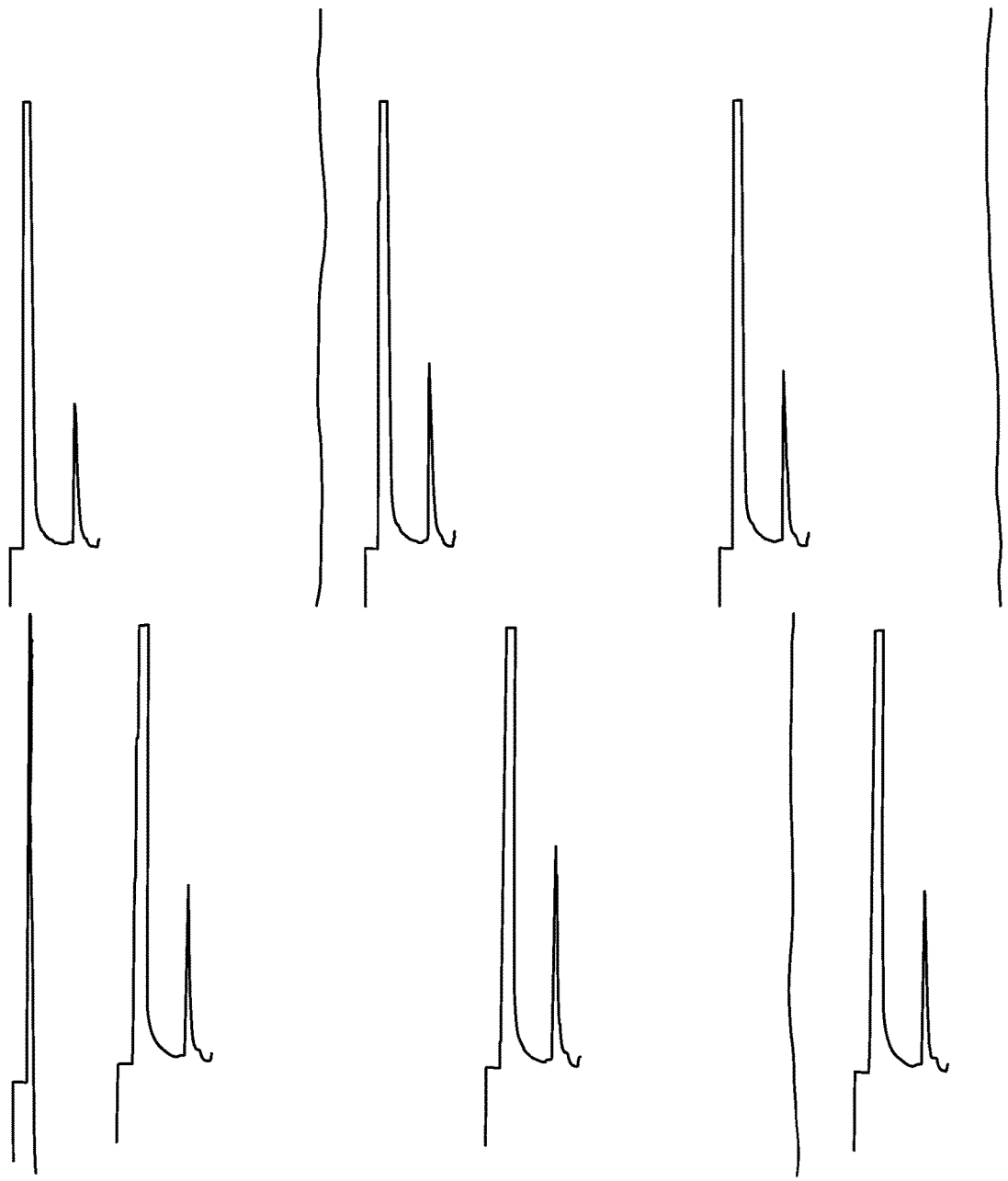
Figure 34D:
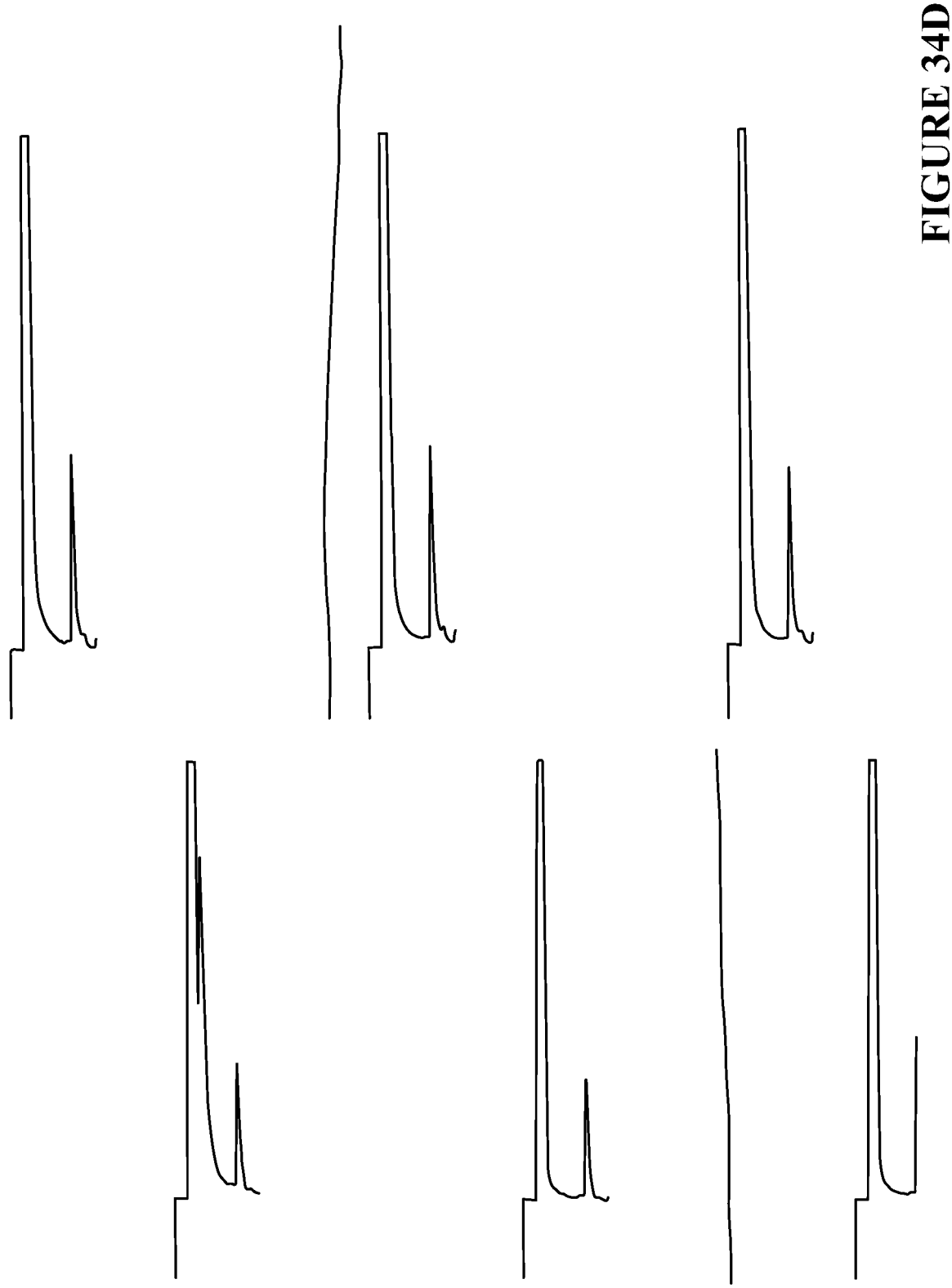
Figure 34E:
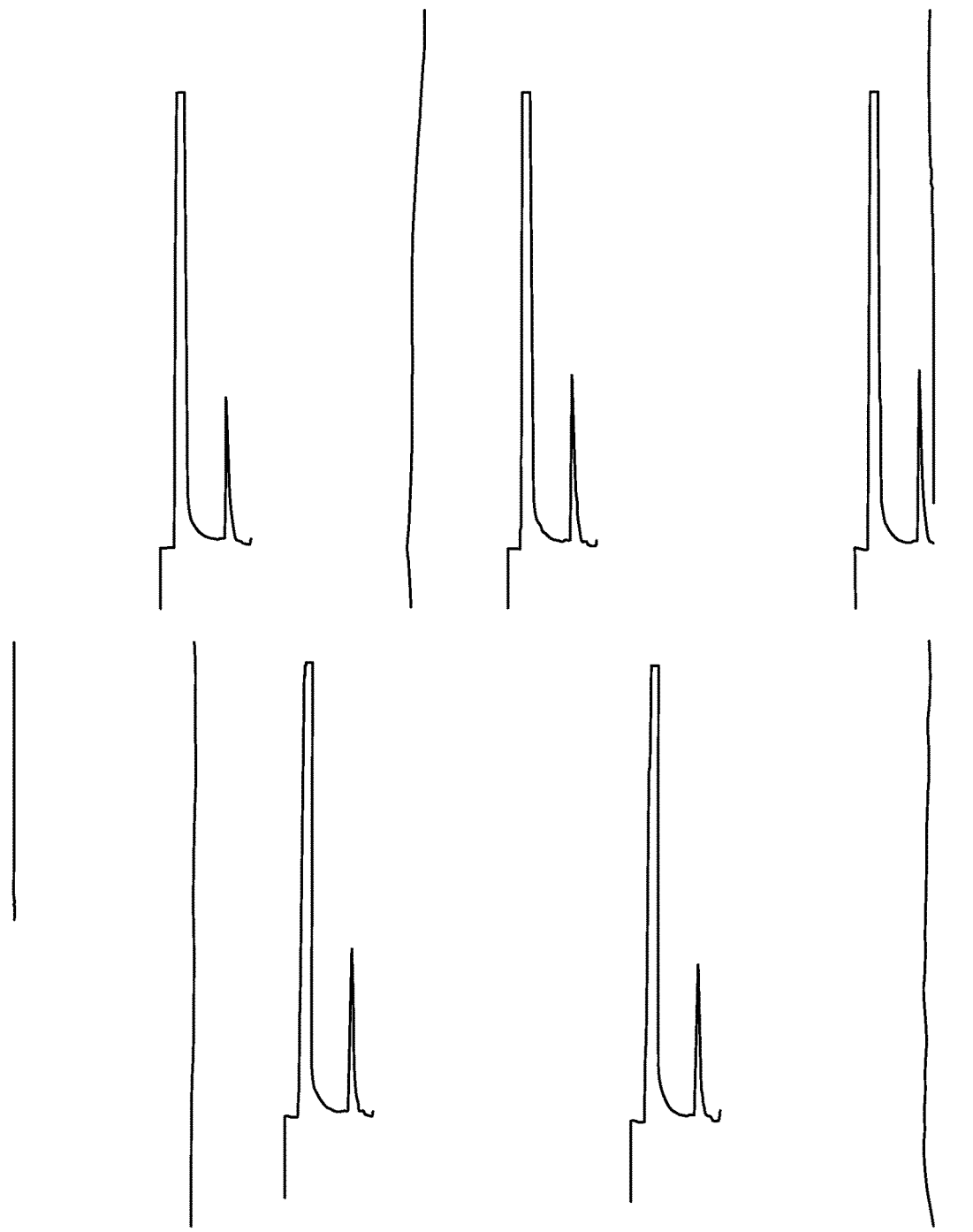
Figure 35A:
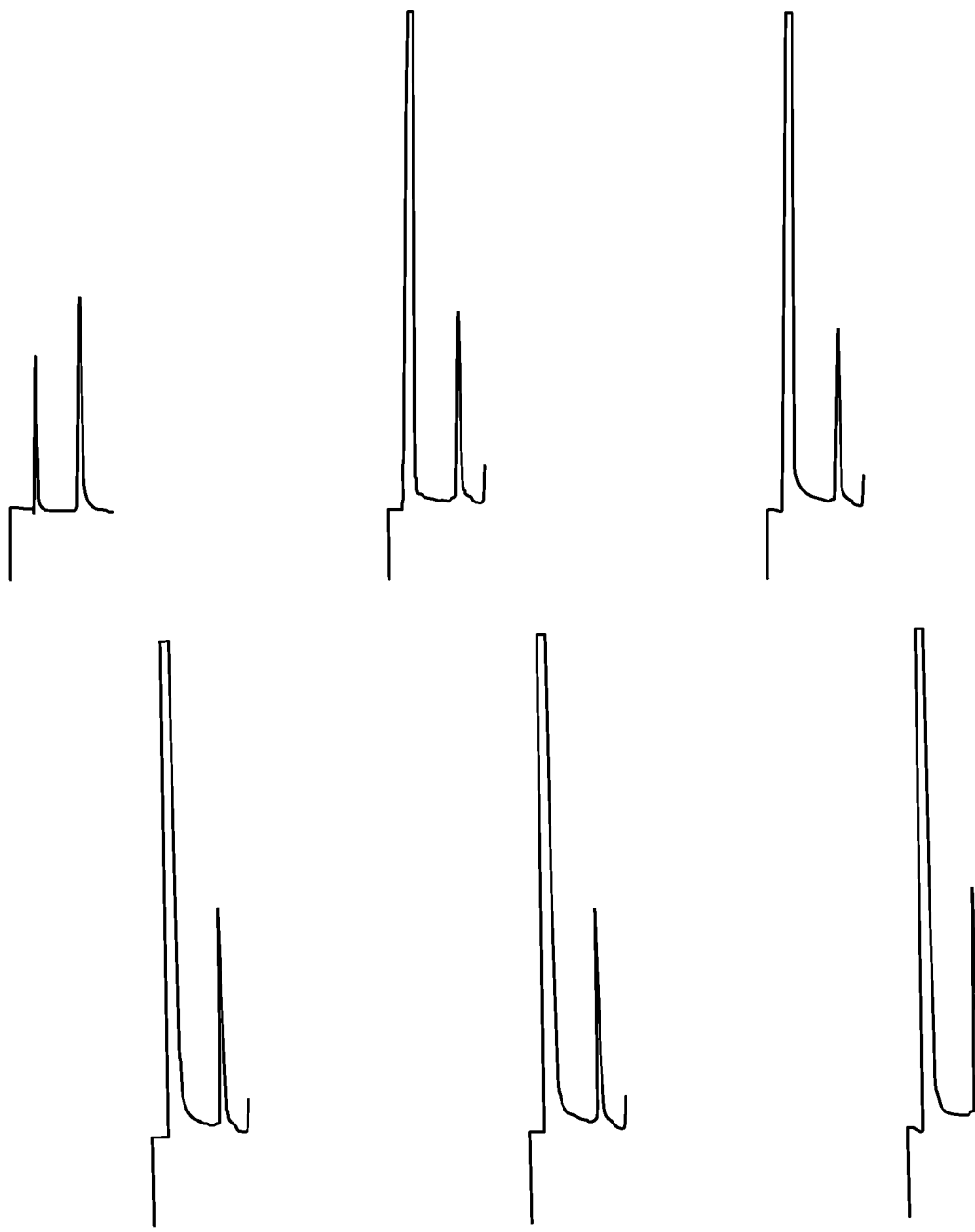
FIG. 35 A to J Typical HPLC chromatograms of dissolution samples 4 to 6 of fentanyl wafers at sampling times of 1, 2, 3, 4, 5, 7 and 10 minutes.
Figure 35B:
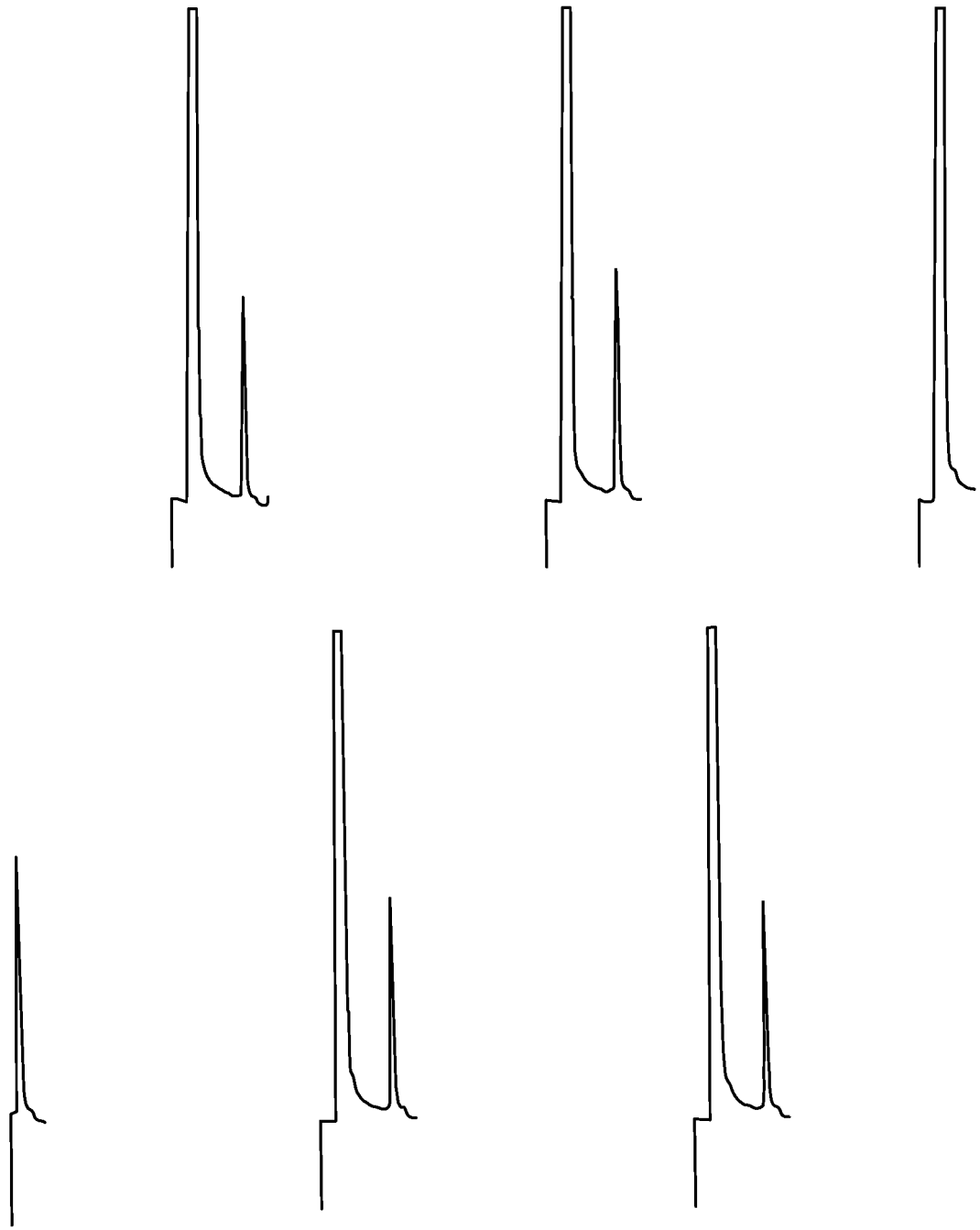
Figure 35C:
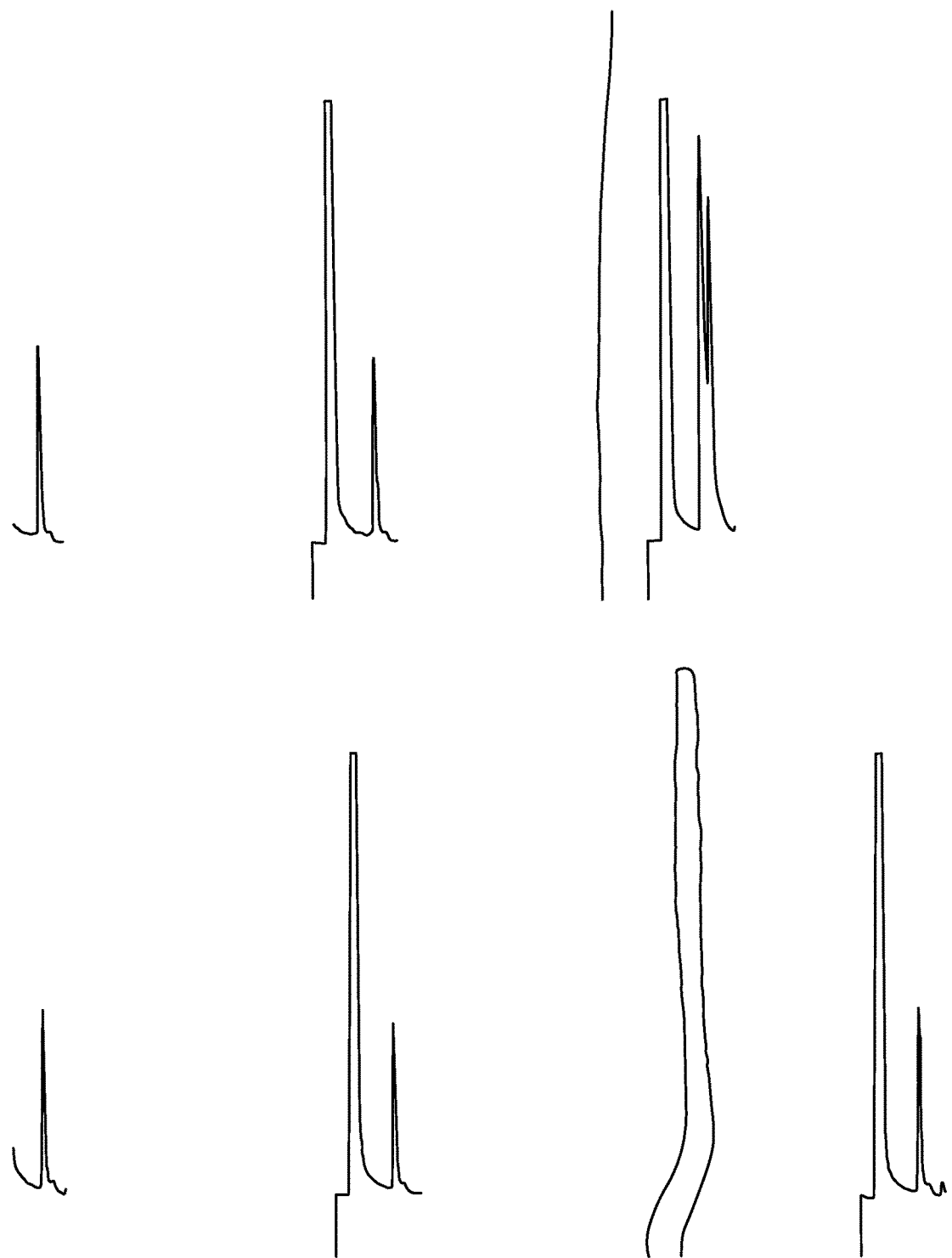
Figure 35D:
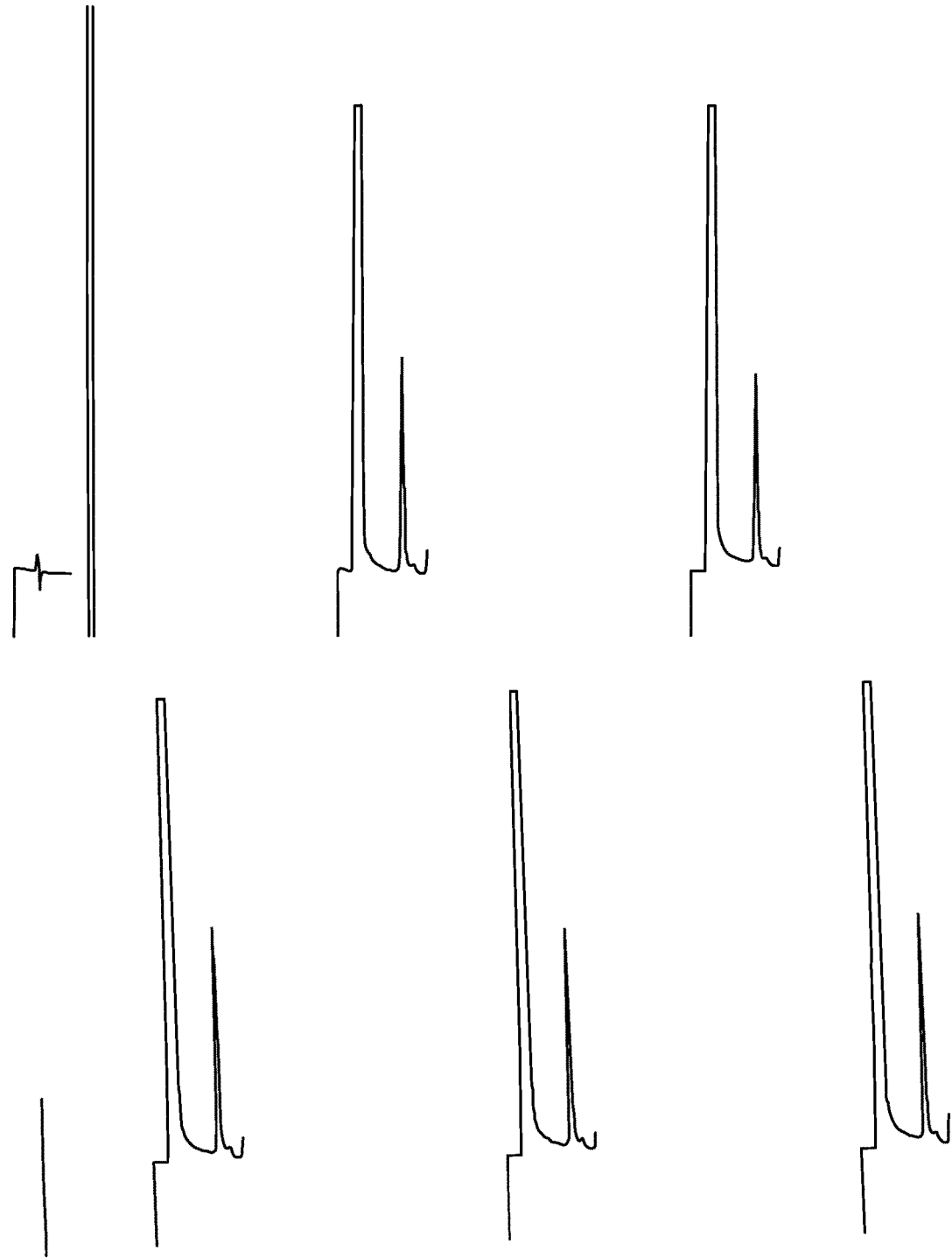
Figure 35E:
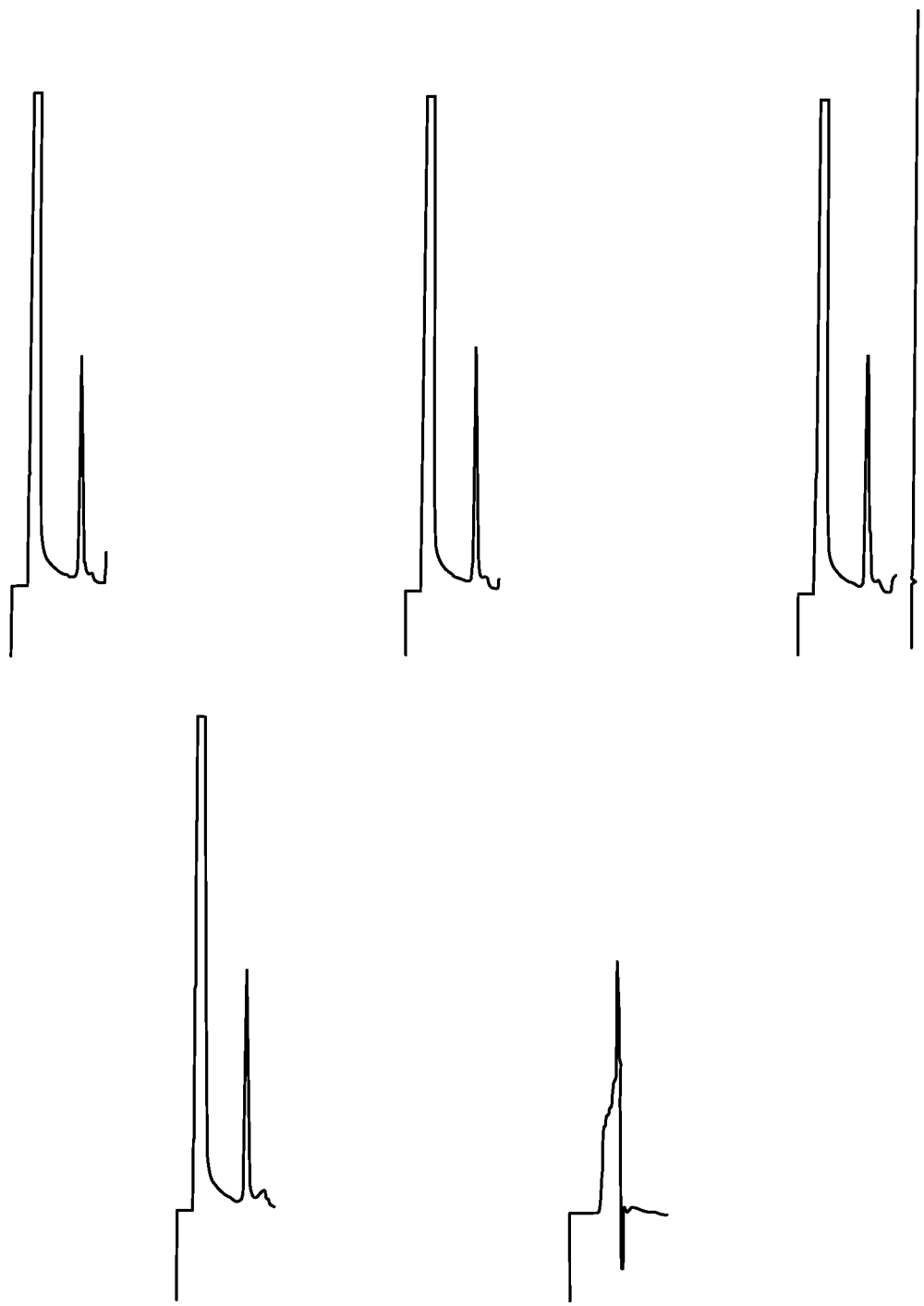
Figure 35F:
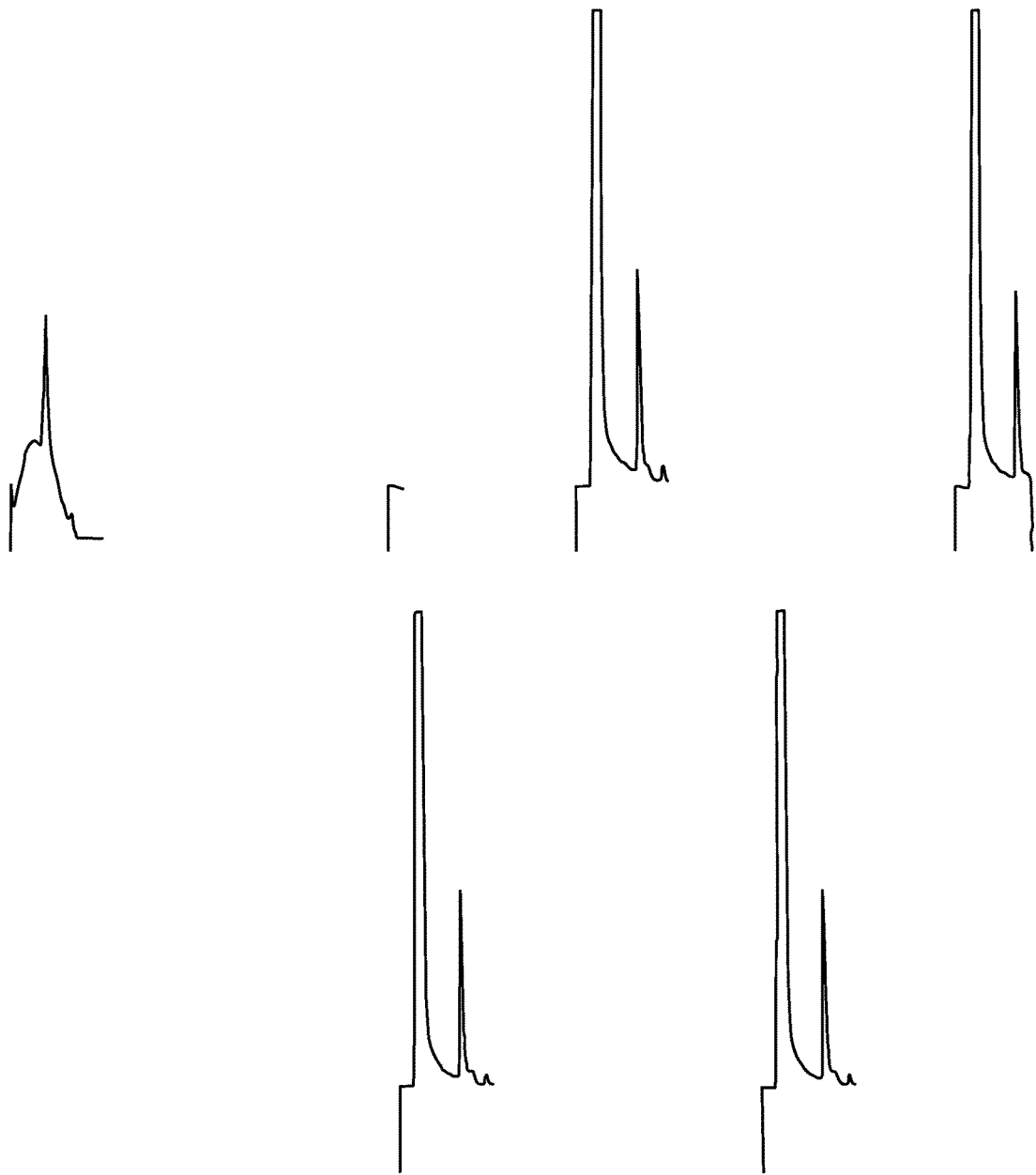
Figure 35G:
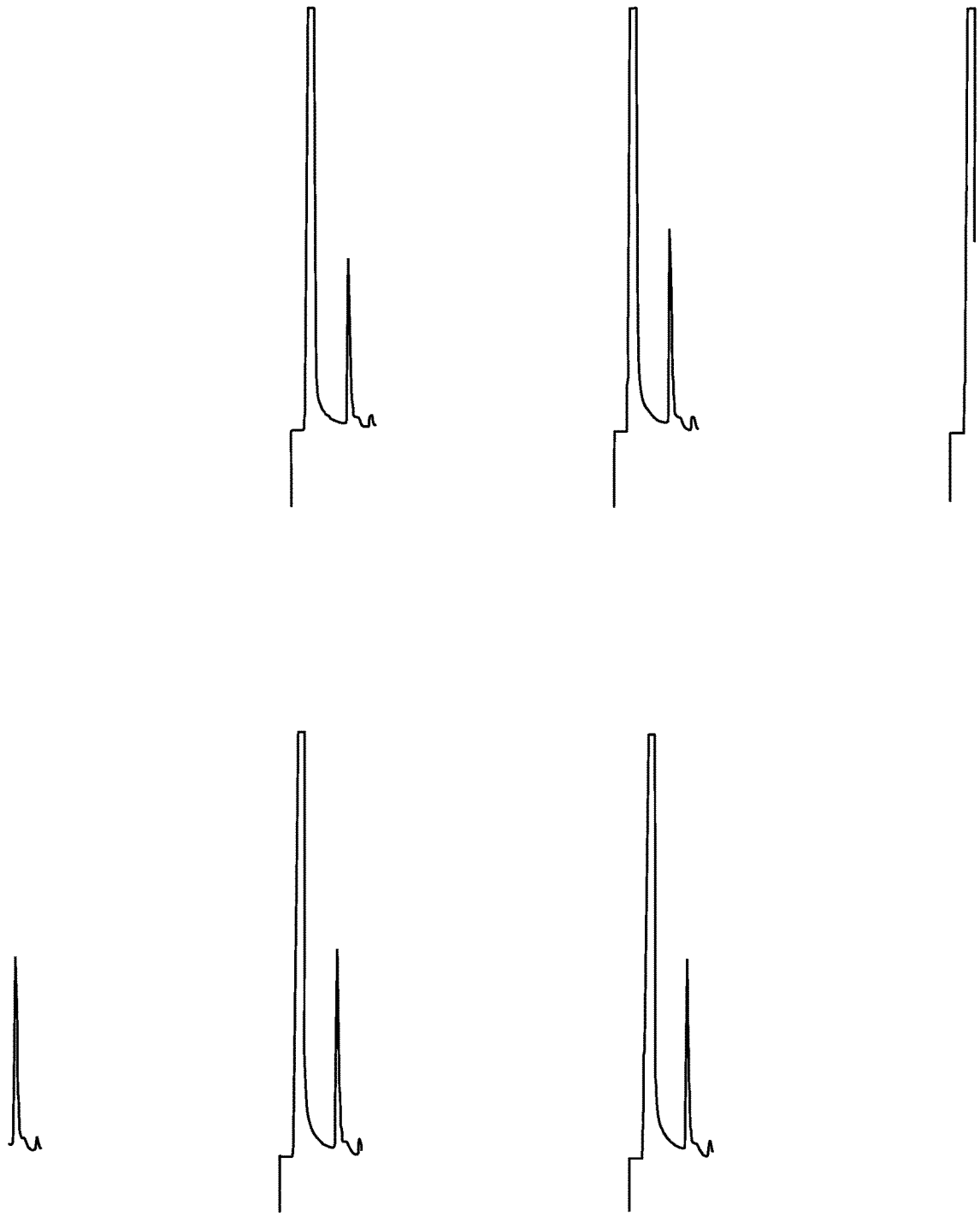
Figure 35H:
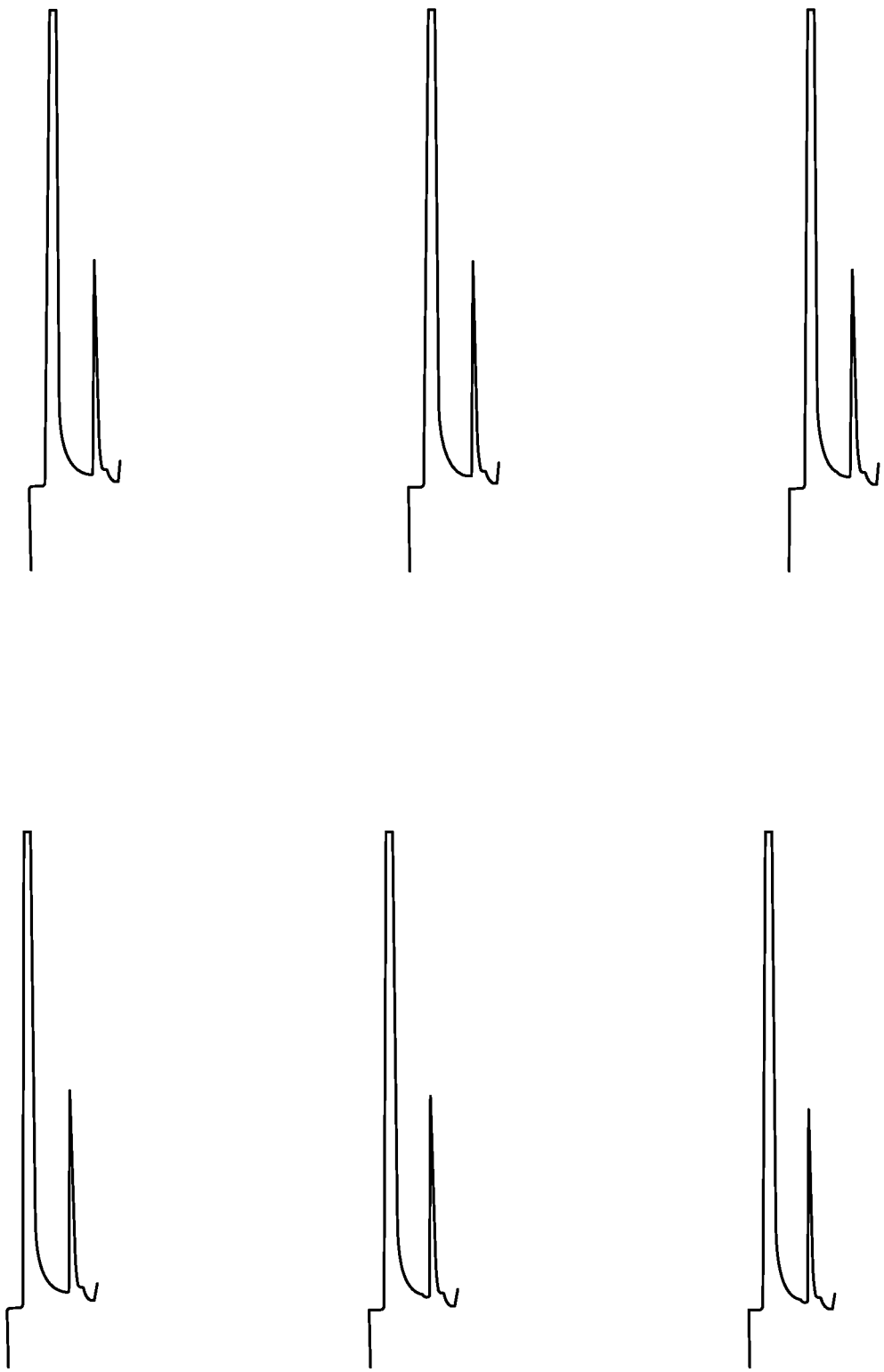
Figure 35I:
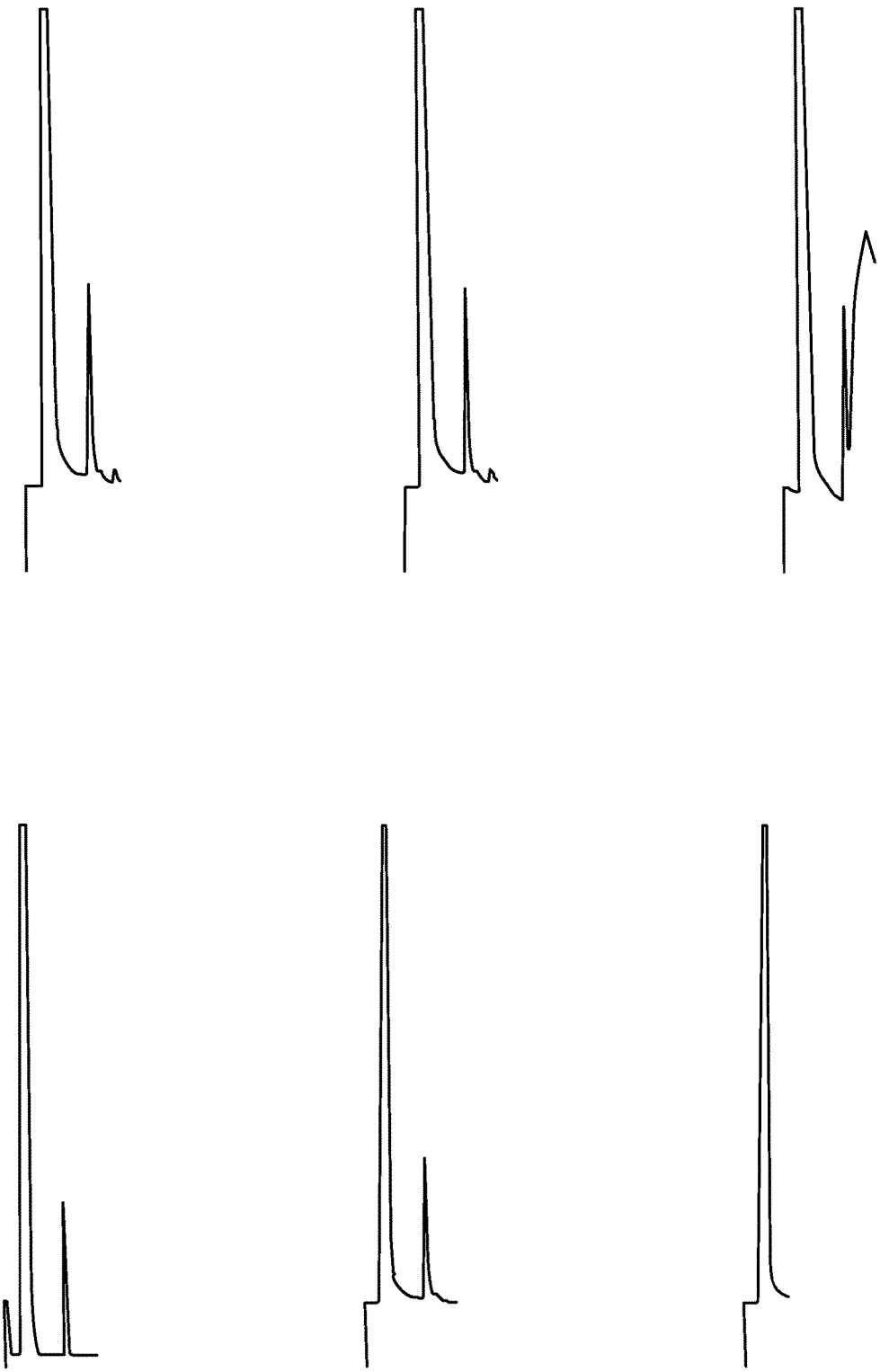
Figure 35J:
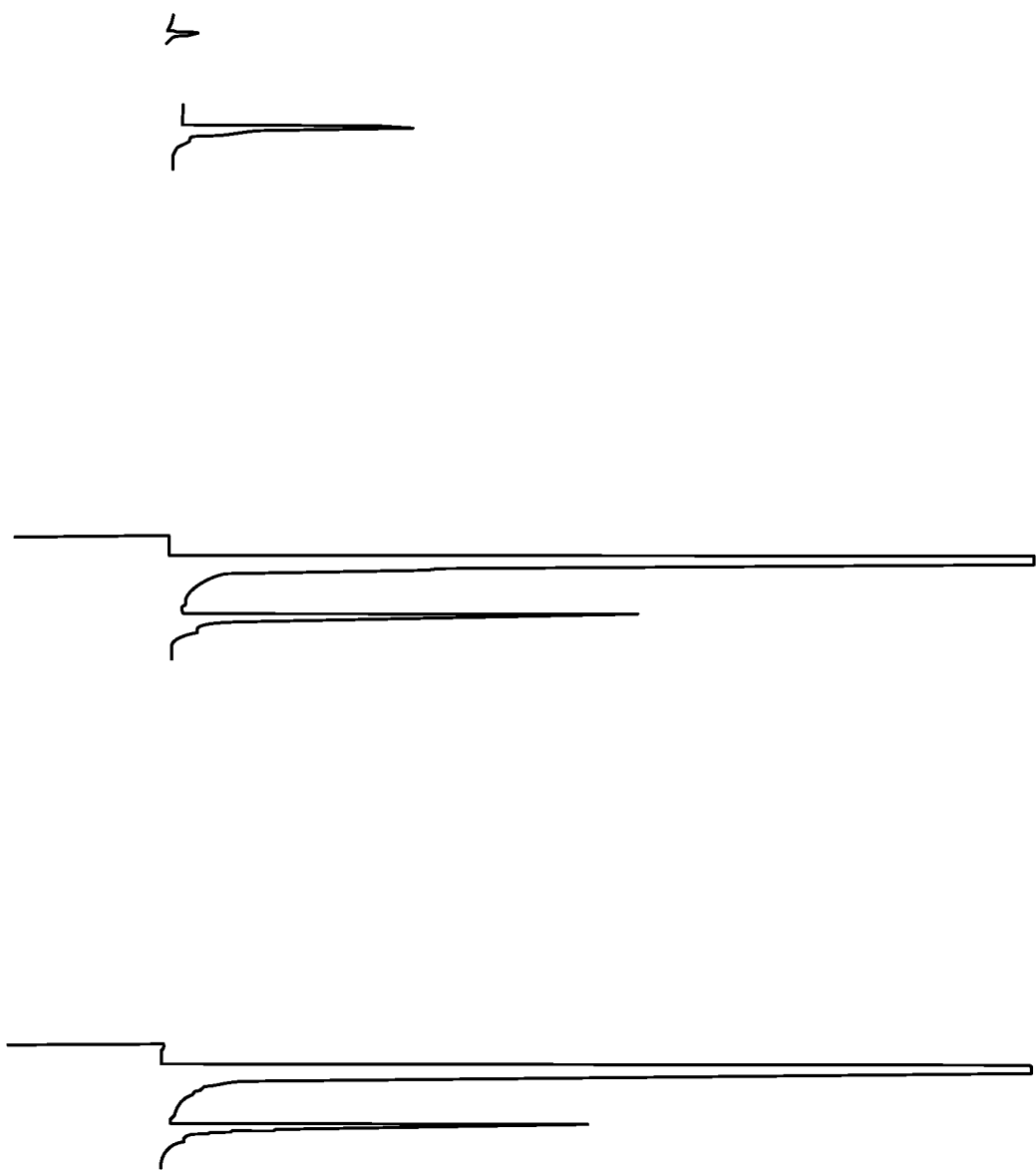

The prepared fentanyl wafer (batch 1003FEN) showed a weight variation of ±2.55%, and the mean percentage fentanyl content of the wafer was 91.32% (BP standard for uniformity content limits 85 to 115%). The average disintegration times were less than 15 seconds; and the dissolution studies also indicated a fast release rate of fentanyl. Almost 90% of fentanyl had dissolved in one minute. The dissolution profiles are presented in FIG. 33.

The HPLC chromatograms of six dissolution samples of fentanyl wafers were collected and is shown in FIGS. 34 A to E (samples 1 to 3) and FIGS. 35 A to J. (samples 4 to 6). The sampling of each test wafer was conducted at time of 0.5, 1, 5, 10, 15 and 20 minutes for dissolution samples 1 to 3, and at 1, 2, 3, 4, 5, 7 and 10 minutes for dissolution samples 4 to 6.

The fast dissolving dosage form is a solid dispersion of drug into a porous matrix. After administration, this dosage form quickly disintegrates in the oral cavity, and allows rapidly dissolving drug to be absorbed by diffusion directly into the systemic circulation, and the first-pass effect is avoided. This invention has the potential to provide an alternate route of drug administration and results in lower rates of side effect.

What is claimed is:

1. A fast disintegrating and dissolving freeze-dried wafer solid dosage form with a porous matrix for release of a biologically active material in an oral cavity wherein said dosage form comprises:
    (a) a biologically active material;
    (b) amylopectin at a concentration from 2% to 17% by dry weight of the dosage form;
    (c) sodium carboxymethyl cellulose (CMC) at a concentration from 0.1 to 15% dry weight of the dosage form; and
    (d) a carbohydrate chosen from a list consisting of: mannitol, dextrose, lactose, galactose and trehalose at a concentration from 5% to 80% by dry weight of the dosage form,
    wherein the powder x-ray diffraction (XRD) of the dosage form comprises peaks at 2-theta values at approximately 9.58 degrees, 19.68 degrees, and 20.05 degrees; and
wherein said dosage form disintegrates in the oral cavity in a time of less than 15 seconds and dissolves in the oral cavity in a time of less than 60 seconds without leaving a residue of said dosage form in the oral cavity that is detectable by a subject, thereby avoiding the urge for the subject to swallow the dosage form;
    wherein said biologically active material is absorbed by diffusion directly into the systemic circulation;
    wherein the amylopectin is not in the form of starch or modified starch.

2. The dosage form according to claim 1, wherein the biologically active material is present in an amount from 0.02 to 95 weight % by dry weight of the composition of the dosage form.

3. The dosage form according to claim 1, further comprising glycine.

4. The dosage form according to claim 3, wherein glycine is present in an amount from 0.5 to 5 weight % by dry weight of the dosage form.

5. The dosage form according to claim 1, comprising mannitol.

6. The dosage form according to claim 5, wherein mannitol is present in an amount from 5 to 80 weight % by dry weight of the dosage form.

7. The dosage form according to claim 1, further comprising a lubricant.

8. The dosage form according to claim 7, wherein the lubricant comprises polyethylene glycol (PEG) 2000.

9. The dosage form according to claim 8, wherein PEG 2000 is present in an amount from 0.05 to 5 weight % by dry weight of the dosage form.

10. The dosage form according to claim 1, further comprising a buffer reagent.

11. The dosage form according to claim 10, wherein the buffer reagent comprises sodium carbonate.

12. The dosage form according to claim 11, wherein sodium carbonate is present in an amount from 0.01 to 10 weight % by dry weight of the dosage form.

13. The dosage form according to claim 1, further comprising an absorption enhancer.

14. The dosage form according to claim 13, wherein the absorption enhancer comprises β-cyclodextrin.

15. The dosage form according to claim 14, wherein β-cyclodextrin is present in an amount from 0.01 to 10 weight % by dry weight of the dosage form.

16. The dosage form according to claim 1, further comprising a flocculating agent.

17. The dosage form according to claim 1, further comprising a surfactant.

18. The dosage form according to claim 1, further comprising an additive.

19. The dosage form according to claim 1, further comprising a coloring agent.

20. The dosage form according to claim 19, wherein the coloring agent is selected from the group consisting of FD&C dyes Blue No. 2, Red No. 40, and mixture therein.

21. The dosage form according to claim 1, further comprising a flavoring agent.

22. The dosage form according to claim 21, wherein the flavoring agent is selected from the group consisting of orange, mint, raspberry, caramel, aspartame, saccharin, and mixture therein.

23. The dosage form according to claim 1, wherein the dosage form dissolves once placed in the oral cavity in a time period selected from the group consisting of: less than 50 seconds, less than 40 seconds, less than 30 seconds, less than 20 seconds, less than 15 seconds, less than 10 seconds, less than 7.5 seconds, less than 5 seconds, less than 4 seconds, less than 3 seconds, and less than 2 seconds.

24. The dosage form according to claim 1, further comprising at least one pharmaceutically acceptable carrier.

25. A kit comprising a fast disintegrating and dissolving freeze-dried wafer solid dosage form with a porous matrix for release of a biologically active material in an oral cavity, wherein the dosage form comprises:
   (a) a biologically active material;
   (b) amylopectin at a concentration from 2% to 17% by dry weight of the dosage form;
   (c) sodium carboxymethyl cellulose (CMC) at a concentration from 0.1 to 15% dry weight of the dosage form; and
   (d) a carbohydrate chosen from a list consisting of: mannitol, dextrose, lactose, galactose and trehalose at a concentration from 5% to 80% by dry weight of the dosage form,
   wherein the powder x-ray diffraction (XRD) of the dosage form comprises peaks at 2-theta values at approximately 9.58 degrees, 19.68 degrees, and 20.05 degrees;
   wherein the dosage form dissolves in the oral cavity without leaving a residue of said dosage form in the oral cavity that is detectable by a subject, thereby avoiding the urge for the subject to swallow the dosage form;
   wherein said dosage form disintegrates in the oral cavity in a time of less than 15 seconds and dissolves in the oral cavity in a time of less than 60 seconds;
   wherein said dosage form is absorbed by diffusion directly into the systemic circulation;
   wherein the amylopectin is not in the form of starch or modified starch; and
   wherein the solid dosage form is not a film.

26. The kit according to claim 25, further comprising instructions for its use.

27. The dosage form of claim 1, wherein the dosage form does not contain modified starch.

28. The kit of claim 25, wherein the dosage form does not contain modified starch.

29. A freeze-dried wafer dosage form with a porous matrix for release of a biologically active material in an oral cavity wherein said dosage form comprises:
   (a) a biologically active material;
   (b) a matrix forming agent comprising amylopectin at a concentration from 2% to 17% by dry weight of the dosage form;
   (c) sodium carboxymethyl cellulose (CMC) at a concentration from 0.1 to 15% dry weight of the dosage form; and
   (d) a carbohydrate chosen from a list consisting of: mannitol, dextrose, lactose, galactose and trehalose at a concentration from 5% to 80% by dry weight of the dosage form,
   wherein the powder x-ray diffraction (XRD) of the dosage form comprises peaks at 2-theta values at approximately 9.58 degrees, 19.68 degrees, and 20.05 degrees;
   wherein said dosage form disintegrates in the oral cavity in a time of less than 15 seconds and dissolves in the oral cavity in a time of less than 60 seconds without leaving a residue of said dosage form in the oral cavity that is detectable by a subject;
   wherein said biologically active material is absorbed by diffusion directly into the systemic circulation;
   wherein the amylopectin is not in the form of starch or modified starch; and
   wherein the solid dosage form is not a film.

\* \* \* \* \*